(12) United States Patent
Francois et al.

(10) Patent No.: US 8,580,735 B2
(45) Date of Patent: Nov. 12, 2013

(54) LOCAL COMPLEMENT INHIBITION FOR TREATMENT OF COMPLEMENT-MEDIATED DISORDERS

(75) Inventors: Cedric Francois, Louisville, KY (US); Pascal Deschatelets, Louisville, KY (US); Paul Olson, Louisville, KY (US)

(73) Assignee: Apellis Pharmaceuticals, Inc., Crestwood, KY (US)

( * ) Notice: Subject to any disclaimer, the term of this patent is extended or adjusted under 35 U.S.C. 154(b) by 649 days.

(21) Appl. No.: 12/525,799

(22) PCT Filed: Feb. 5, 2008

(86) PCT No.: PCT/US2008/001483
§ 371 (c)(1),
(2), (4) Date: Mar. 8, 2010

(87) PCT Pub. No.: WO2008/097525
PCT Pub. Date: Aug. 14, 2008

(65) Prior Publication Data
US 2010/0166862 A1 Jul. 1, 2010

Related U.S. Application Data

(60) Provisional application No. 60/899,474, filed on Feb. 5, 2007.

(51) Int. Cl.
*A61K 38/00* (2006.01)
*A61K 38/10* (2006.01)

(52) U.S. Cl.
USPC ............................. 514/12.2; 514/21.5

(58) Field of Classification Search
None
See application file for complete search history.

(56) References Cited

U.S. PATENT DOCUMENTS

| | | | |
|---|---|---|---|
| 7,279,158 B2 * | 10/2007 | Wang et al. | 424/130.1 |
| 2002/0058614 A1 | 5/2002 | Filvaroff et al. | |
| 2005/0281861 A1 | 12/2005 | Hughes et al. | |
| 2007/0141573 A1 | 6/2007 | Nunn | |
| 2007/0178068 A1* | 8/2007 | Reich et al. | 424/93.2 |
| 2011/0311549 A1* | 12/2011 | Schwaeble et al. | 424/146.1 |
| 2012/0004393 A1* | 1/2012 | Lambris et al. | 530/324 |

FOREIGN PATENT DOCUMENTS

| | | |
|---|---|---|
| WO | 94/17822 | 8/1994 |
| WO | 97/33603 | 9/1997 |
| WO | 01/84149 A2 | 11/2001 |
| WO | 2004/022096 A1 | 3/2004 |
| WO | 2004/026328 A1 | 4/2004 |
| WO | 2006/042252 A2 | 4/2006 |
| WO | 2007/044668 A2 | 4/2007 |
| WO | 2007/062249 A2 | 5/2007 |
| WO | 2007/084765 A2 | 7/2007 |
| WO | 2007/138328 A2 | 12/2007 |

OTHER PUBLICATIONS

Chun He "Targeted delivery of complement inhibitors to the proximal tubule suppresses acute tubulointerstitial injury to experimental Nephrotic Syndrome" ProQeust Dissertations and Theses; 2004.*
Robert Langer "Drug delivery and targeting" Nature, 392(Supp), 1998, pp. 5-10.*
Song et al. "Complement receptor 2-mediated targeting of complement inhibitors to sites of complement activation" J. Clinical Invest. 111(12), 2003, pp. 1875-1885.*
Stahel et al. "The role of the complement system in CNS inflammatory diseases" Future Drugs Ltd, pp. 445-456.*
Marc et al. "Complement Factors C3a, C4a, and C5a in Chronic Obstructive Pulmonary Disease and Asthma" Am. J. Respir. Cell Mol. Biol., 31(2), 2004, pp. 216-219.*
Supplementary European Search Report for EP 08 72 5157, mailed Jun. 15, 2012.
Johnson et al., "Complement activation and inflammatory processes in Drusen formation and age related macular degeneration", Exp. Eye Res., 73(6):887-896 (2001).
Mallik et al., "Design and NMR characterization of active analogues of compstatin containing non-natural amino acids", J. Med. Chem., 48(1):274-286 (2005).
Morikis et al., "Solution structure of Compstatin, a potent complement inhibitor", Protein Sci., 7(3):619-627 (1998).
International Search Report for PCT/US2008/001483, mailed May 23, 2011.
Goodfellow, R.M. et al., Local therapy with soluble complement receptor 1 (sCR1) supresses inflammation in rat mono-articular arthritis, Clin. Exp. Immunol., 110:45-52 (1997).
Linton, S.M. et al., Complement activation and inhibition in experimental models of arthritis, Mol. Immunol., 36L905-914 (1999).
Peng, T. et al., Blocking Intrapulmonary Activation of Complement Cascade on the Development of Airway Hyperresponsiveness: Utility in Sight?, Late Breaking Abstracts: Basic Sciences, presented at Scientific Sessions AAAAI 62nd Annual Meeting, Mar. 3-7, Abstract LB2 (2006).
Wang, Y., Complementary therapies for inflammation, Nat. Biotechnol., 24(10):1224-1226 (2006).
Ali et al., Anaphylatoxin C3a Receptors in Asthma, Respiratory Res., 6:19 (2005).
Gauvreau et al., The Effect of C5 Inhibition by Eculizumab on Allergen-Induced Asthmatic Response in Patients, Mol. Immunol., 46:2818-2871, Abstract only (2009).

(Continued)

Primary Examiner — Daniel E Kolker
Assistant Examiner — James Rogers
(74) Attorney, Agent, or Firm — Choate Hall & Stewart, LLP; Brenda H. Jarrell; Justin P. Huddleson

(57) ABSTRACT

The present invention features the local administration of complement inhibitors for treatment of complement-mediated disorders. In certain embodiments the invention features inhibiting activation of one or more locally produced complement proteins. The invention provides sustained release formulations and devices comprising a complement inhibitor and methods of use thereof.

21 Claims, 1 Drawing Sheet

(56) References Cited

OTHER PUBLICATIONS

Lajoie et al., Complement-Mediated Regulation of the Interleukin 17A Axis is a Central Genetic Determinant of the Security of Exprerimental Allergic Asthma, Nat. Immunol., 11(10):928-935 (2010).

Marc et al., Complement Factors C3a, C4a, and C5a in Chronic Obstructive Pulmonary Disease and Asthma, Am. J. Respir. Cell Mol. Biol., 31:216-219 (2004).

Peng et al., Role of C5 in the Development of Airway Inflammation, Airway Hyperresponsiveness, and Ongoing Airway Response, J. Clin. Invest., 115(6):1590-1600 (2005).

Taube, Christian, Inhibition of Complement Activation Decreases Airway Inflammation and Hyperresponsiveness, Am. J. Resp. and Critical Care Med., 14 pages (2003).

Wust et al., Complement in Asthma: Sensitivity to Activation and Generation of C3a and C5a via the Different Complement Pathways, Translational Res., 148:157-163 (2006).

* cited by examiner

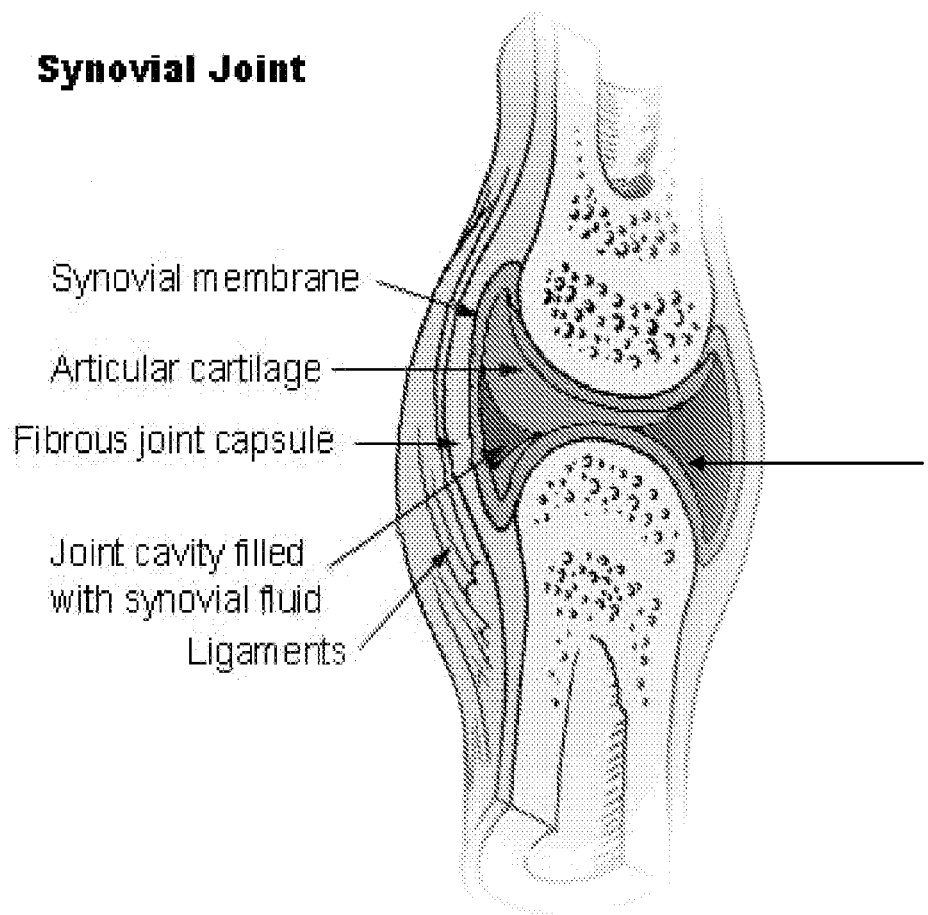

LOCAL COMPLEMENT INHIBITION FOR TREATMENT OF COMPLEMENT-MEDIATED DISORDERS

CROSS-REFERENCE TO RELATED APPLICATIONS

This application is a U.S. national phase application under 35 U.S.C. 371 of international PCT application no. PCT/US08/001,483, filed Feb. 5, 2008, which claims the benefit of priority to U.S. provisional patent application Ser. No. 60/899,474, filed Feb. 5, 2007, the entire contents of which are herein incorporated by reference.

SEQUENCE LISTING

In accordance with 37 C.F.R. §1.52(e)(5), a Sequence Listing in the form of a text file (entitled "SequenceListing.txt," created on Sep. 2, 2009 and 25 kb in size) is incorporated herein by reference in its entirety.

BACKGROUND OF THE INVENTION

The complement system comprises more than 30 soluble and cell-bound proteins and plays an important role in both innate and acquired immunity, particularly in the body's response to infection. In the absence of a triggering event, many complement proteins exist primarily in an inactive, proenzyme form. Following activation, often by proteolytic cleavage, they participate in an enzymatic cascade leading to a number of downstream events such as lysis of cells, bacteria and viruses, opsonization, and activation of immune responses such as inflammation and cytokine secretion.

Complement activation occurs via three main pathways, known as the classical, alternative, and lectin pathways (*Kuby Immunology*, 2000). The classical pathway is usually triggered by binding of a complex of antigen and IgM or IgG antibody to C1 (though certain other activators can also initiate the pathway). Activated C1 cleaves C4 and C2 to produce C4a and C4b, in addition to C2a and C2b. C4b and C2a combine to form C3 convertase, which cleaves C3 to form C3a and C3b. Binding of C3b to C3 convertase produces C5 convertase, which cleaves C5 into C5a and C5b. C3a, C4a, and C5a are anaphylotoxins and mediate multiple reactions in the acute inflammatory response. C3a and C5a are also chemotactic factors that attract immune system cells such as neutrophils.

The alternative pathway is initiated by microbial surfaces and various complex polysaccharides. In this pathway, C3b, resulting from cleavage of C3, which occurs spontaneously at a low level, binds to targets, e.g., on cell surfaces and forms a complex with factor B, which is later cleaved by factor D, resulting in a C3 convertase. Cleavage of C3 and binding of another molecule of C3b to the C3 convertase gives rise to a C5 convertase.

The C5 convertases produced in both pathways cleave C5 to produce C5a and C5b. C5b then binds to C6, C7, and C8 to form C5b-8, which catalyzes polymerization of C9 to form the C5b-9 membrane attack complex (MAC). The MAC inserts itself into target cell membranes and causes cell lysis. Small amounts of MAC on the membrane of cells may have a variety of consequences other than cell death.

A third complement pathway, the lectin complement pathway is initiated by binding of mannose-binding lectin (MBL) and MBL-associated serine protease (MASP) to carbohydrates. In the human lectin pathway, MASP-1 and MASP-2 are involved in the proteolysis of C4, C2 and C3, leading to a C3 convertase described above.

Complement activity is regulated by members of the endogenous "regulators of complement activation" (RCA) family, also called "complement control proteins" (CCPs), which include complement receptor type 1 (CR1; C3b:C4b receptor), complement receptor type 2 (CR2), membrane cofactor protein (MCP; CD46), decay-accelerating factor (DAF), complement factor H (fH), complement receptor-related protein y (CRRY), and C4b-binding protein (C4bp). CCPs are characterized by multiple (typically 4-56) homologous motifs known as short consensus repeats (SCR), complement control protein (CCP) modules, or SUSHI domains (Reid, K B M and Day, A J, *Immunol Today*, 10:177-80, 1989). Complement control proteins negatively regulate the complement system, e.g., by accelerating the normal decay of convertases and/or functioning as cofactors for factor I to enzymatically cleave C3b and/or C4b into smaller fragments.

While complement activation plays important roles in the innate and adaptive immune systems, the complement system is increasingly recognized to be involved in tissue injury during a variety of ischemic, inflammatory, and autoimmune diseases (Makrides, S C, *Pharm Rev.*, 50(1): 59-87, 1998; Lisczewski, M K and Atkinson, J P, in *The Human Complement System in Health and Disease*, Volanakis, J E and Frank, M M, eds., Dekker, New York, pp. 149-66, 1998). Complement inhibition has been proposed as a therapeutic strategy for many such diseases. Unfortunately, a number of complement inhibitors have been less successful in the clinic than had been hoped. Nonetheless, complement inhibition remains an attractive option. Thus there is a need in the art for new compositions and methods for productively harnessing complement inhibition as a therapeutic modality for a variety of complement-mediated disorders.

SUMMARY OF THE INVENTION

The present invention addresses the foregoing needs, among others. In one aspect, the invention provides a method of treating a complement-mediated disorder comprising the step of: administering a complement inhibitor directly to an extravascular location that is a site of local complement activation in said disorder. In certain embodiments the complement inhibitor inhibits an enzymatic activity or the activation of a soluble complement protein such as C3, factor B, or factor D. In certain embodiments the complement inhibitor is a compstatin analog. In certain embodiments the complement inhibitor is administered in a sustained release formulation or device. In certain embodiments the sustained release formulation comprises a plurality of microparticles or nanoparticles. In certain embodiments the sustained release formulation comprises a gel. In certain embodiments the sustained release formulation comprises a gel that forms in the body following administration of a liquid that contains the complement inhibitor.

In another aspect the invention provides a sustained release composition comprising a complement inhibitor and a compound selected from the group consisting of: steroidal or nonsteroidal anti-inflammatory agents, local anesthetic agents, leukotriene or leukotriene receptor antagonists, cytokine or cytokine receptor antagonists, matrix metalloprotease inhibitors, phosphodiesterase inhibitors, anti-histamines, anti-angiogenic, and anti-infective agents.

In another aspect the invention provides a method of treating inflammatory arthritis comprising administering a complement inhibitor directly to a joint or bursa, wherein said complement inhibitor is administered in an amount effective to substantially inhibit activation of a locally produced complement component or in an amount effective to substantially inhibit local activation of complement. In certain embodiments said inflammatory arthritis is rheumatoid arthritis, psoriatic arthritis, Reiter's syndrome, juvenile arthritis, or gout.

In another aspect the invention provides a method of treating an inflammatory condition of the respiratory system comprising administering a complement inhibitor directly to the respiratory tract, wherein said complement inhibitor is administered in an amount effective to substantially inhibit activation of a locally produced complement component or in an amount effective to substantially inhibit local activation of complement. The inflammatory condition of the respiratory system may be selected from the group consisting of: asthma, COPD, allergic rhinitis, and infection-associated inflammation.

In another aspect the invention provides a method of treating a complement-mediated disorder of the nervous system comprising administering a complement inhibitor to a region of the nervous system by a route selected from the group consisting of: intrathecal, intranasal, and by local injection into a nerve sheath wherein said complement inhibitor is administered in an amount effective to substantially inhibit activation of a locally produced complement component or in an amount effective to substantially inhibit local activation of complement. In certain embodiments the complement-mediated disorder is selected from the group consisting of: spinal cord injury, multiple sclerosis, Alzheimer's disease, Parkinson's disease, stroke, and chronic pain.

In another aspect the invention provides a method of treating a skin condition comprising administering a complement inhibitor directly to the skin, wherein said complement inhibitor is administered in an amount effective to inhibit activation of a locally produced soluble complement component or in an amount effective to substantially inhibit local activation of complement. The skin condition may be selected from the group consisting of: psoriasis, pemphigus, scleroderma, and lupus.

In another aspect the invention provides a method of treating a complement-mediated disorder comprising administering a sustained release formulation comprising an effective amount of a compstatin analog to an extravascular location where complement activation occurs, wherein said location is not the eye.

In another aspect the invention provides a method of treating a complement-mediated disorder comprising administering a sustained release formulation comprising an effective amount of a compstatin analog to an extravascular location where complement activation occurs, wherein said location is not the eye.

In certain embodiments of the afore-mentioned methods, local administration of the complement inhibitor does not substantially inhibit systemic complement activity.

In another aspect the invention provides a method of treating an ocular disorder characterized by macular degeneration and/or inflammation comprising administering an effective amount of an anti-TNFα agent to a subject in need thereof, optionally in combination with a complement inhibitor. In certain embodiments the anti-TNFα agent comprises an antibody or soluble TNFα receptor.

In another aspect, the invention provides a sustained release formulation or device comprising a biodegradable drug releasing material, a complement inhibitor, and a detectable moiety. In certain embodiments the detectable moiety is fluorescent or is an ultrasound or magnetic resonance contrast enhancer. The invention further provides a method of treating a subject comprising: (a) administering to the subject a first quantity of a first biodegradable sustained release formulation or device comprising a detectable moiety and therapeutic agent such as a complement inhibitor and (b) detecting the detectable moiety using a non-invasive detection method. In certain embodiments presence and/or amount of the moiety detected serves as an indication of the amount of the sustained release formulation or device that remains intact or has degraded and/or serves as an indication of the amount of the therapeutic agent remaining in the sustained release formulation or device; and the method optionally comprises (c) administering to the subject a second quantity of a second sustained release formulation or device based on the results of step (b). Steps (b) and (c) may be repeated one or more times.

In other aspects, the invention provides sustained release formulations and devices, wherein the improvement comprises use of a complement inhibitor as an active agent. The complement inhibitor is a compstatin analog in certain embodiments of the invention.

In another aspect, the invention comprises a method of administering a complement inhibitor to a subject, the method comprising administering a sustained release formulation comprising the complement inhibitor to an extravascular location in or on the body of the subject.

In another aspect, the invention provides methods of testing the compositions and methods of the invention, e.g., in vitro or in an animal model.

In another aspect, methods for making the compositions of the invention are also provided.

Unless otherwise stated, the invention makes use of standard methods of molecular biology, chemistry, cell culture, animal maintenance, medical and veterinary examination, and administration of therapeutic agents to subjects, etc., and uses art-accepted meanings of terms. This application refers to various patents and publications. The contents of all scientific articles, books, patents, patent applications, and other publications, mentioned in this application are incorporated herein by reference. In addition, the following publications are incorporated herein by reference: *Current Protocols in Molecular Biology, Current Protocols in Immunology, Current Protocols in Protein Science*, and *Current Protocols in Cell Biology*, all John Wiley & Sons, N.Y., edition as of July 2002; Sambrook, Russell, and Sambrook, *Molecular Cloning: A Laboratory Manual*, $3^{rd}$ ed., Cold Spring Harbor Laboratory Press, Cold Spring Harbor, 2001; *Kuby Immunology*, $4^{th}$ ed., Goldsby, R. A., Kindt, T. J., and Osborne, B. (eds.), W.H. Freeman, 2000, *Goodman and Gilman's The Pharmacological Basis of Therapeutics*, $10^{th}$ Ed., McGraw Hill, 2001, Katzung, B. (ed.) *Basic and Clinical Pharmacology*, McGraw-Hill/Appleton & Lange; 9th edition (December 2003); Goldman & Ausiello, *Cecil Textbook of Medicine*, $22^{nd}$ ed., W.B. Saunders, 2003. It will be appreciated that the state of the art may have progressed beyond that represented in certain of the references incorporated herein. In the event of a conflict or inconsistency between any of the incorporated references and the instant specification, the specification shall control unless modified by amendment, it being understood that the determination of whether a conflict or inconsistency exists is within the discretion of the inventors and can be made at any time. Art-accepted abbreviations for the amino acids are used herein unless otherwise indicated.

BRIEF DESCRIPTION OF THE DRAWING

FIG. 1 shows a schematic diagram of a synovial joint.

DEFINITIONS

The terms "angiogenesis inhibitor" and "antiangiogenic agent" are used interchangeably herein to refer to agents that are capable of inhibiting or reducing one or more processes associated with formation, growth, and/or development of new blood vessels including, but not limited to, endothelial cell proliferation, endothelial cell migration, and capillary tube formation. In addition, such agents may inhibit fluid exudation from blood vessels.

The term "antagonist" refers to a compound which inhibits (e.g., antagonizes, reduces, decreases, blocks, or reverses) the effect of a given protein. An antagonist is capable of acting in a manner relative to a particular protein's activity, such that the biological activity of the protein is decreased or blocked in a manner that is antagonistic (e.g., against, opposite to, contrary to) to one or more natural actions of the protein. Antagonists can include, but are not limited to, an antibody or antigen binding fragment thereof, a protein, peptide, nucleic acid (such as RNAi agents, ribozymes, and antisense), or a small molecule.

The term "antibody" refers to an immunoglobulin or a derivative thereof containing an immunoglobulin domain capable of binding to an antigen. The antibody can be of any species, e.g., human, rodent, rabbit, goat, chicken, etc. The antibody may be a member of any immunoglobulin class, including any of the human classes: IgG, IgM, IgA, IgD, and IgE, or subclasses thereof such as IgG1, IgG2, etc. In various embodiments of the invention the antibody is a fragment such as an Fab', F(ab')$_2$, scFv (single-chain variable) or other fragment that retains an antigen binding site, or a recombinantly produced scFv fragment, including recombinantly produced fragments. See, e.g., Allen, T., *Nature Reviews Cancer*, Vol. 2, 750-765, 2002, and references therein. The antibody can be monovalent, bivalent or multivalent. The antibody may be a chimeric or "humanized" antibody in which, for example, a variable domain of rodent origin is fused to a constant domain of human origin, thus retaining the specificity of the rodent antibody. The domain of human origin need not originate directly from a human in the sense that it is first synthesized in a human being. Instead, "human" domains may be generated in rodents whose genome incorporates human immunoglobulin genes. See, e.g., Vaughan, et al., (1998), *Nature Biotechnology*, 16: 535-539. The antibody may be partially or completely humanized. An antibody may be polyclonal or monoclonal, though for purposes of the present invention monoclonal antibodies are generally preferred. Methods for producing antibodies that specifically bind to virtually any molecule of interest are known in the art. For example, monoclonal or polyclonal antibodies can be purified from blood or ascites fluid of an animal that produces the antibody (e.g., following natural exposure to or immunization with the molecule or an antigenic fragment thereof), can be produced using recombinant techniques in cell culture or transgenic organisms, or can be made at least in part by chemical synthesis.

The terms "approximately" or "about" in reference to a number generally include numbers that fall within a range of 5% in either direction of the number (greater than or less than the number) unless otherwise stated or otherwise evident from the context (except where such number would impermissibly exceed 100% of a possible value).

"Biocompatible" is used consistently with its usage in the art and refers to a material that is substantially non-toxic to cells in vitro, e.g., in certain embodiments if its addition to cells in culture in amounts approximating that contemplated for in vivo use results in less than or equal to 20% cell death. A material is considered biocompatible with respect to a recipient if it is substantially nontoxic to the recipient's cells and tissues in the quantities and at the location used, and also does not elicit or cause a significant deleterious or untoward effect on the recipient's body, e.g., an immunological or inflammatory reaction, unacceptable scar tissue formation, etc.

"Biodegradable" means that a material is capable of being broken down physically and/or chemically within cells or within an extracellular location such as a compartment in the body of a subject, e.g., by hydrolysis under physiological conditions, by natural biological processes such as the action of enzymes present within cells or within the body, etc., to form smaller chemical species which can be metabolized and, optionally, reused, and/or excreted or otherwise disposed of. Materials that erode, disintegrate or deteriorate to smaller fragments, e.g., soluble molecules or supramolecular complexes, under physiological conditions are included within the scope of "biodegradable" materials. Preferably a biodegradable material is biocompatible.

A "biological macromolecule" is a large molecule composed of smaller subunits of a type that are found in biological systems. Examples of biological macromolecules include polypeptides, nucleic acids, and polysaccharides. Typically a biological macromolecule contains at least 3 subunits (e.g., amino acids, nucleosides, monosaccharides, etc.). The biological macromolecule may, but need not be, a naturally occurring polypeptide, nucleic acid, or polysaccharide. The biological macromolecule may be modified, e.g., it may be conjugated to a nonbiological molecule such as synthetic polymer, etc.

A "complement component" or "complement protein" is a molecule that is involved in activation of the complement system or participates in one or more complement-mediated activities. Components of the classical complement pathway include, e.g., C1q, C1r, C1s, C2, C3, C4, C5, C6, C7, C8, C9, and the C5b-9 complex, also referred to as the membrane attack complex (MAC) and active fragments or enzymatic cleavage products of any of the foregoing (e.g., C3a, C3b, C4a, C4b, C5a, etc.). Components of the alternative pathway include, e.g., factors B, D, H, and I, and properdin, with factor H being a negative regulator of the pathway. Components of the lectin pathway include, e.g., MBL2, MASP-1, and MASP-2. Complement components also include cell-bound receptors for soluble complement components. Such receptors include, e.g., C5a receptor (C5aR), C3a receptor (C3aR), Complement Receptor 1 (CR1), Complement Receptor 2 (CR2), Complement Receptor 3 (CR3), etc. It will be appreciated that the term "complement component" is not intended to include those molecules and molecular structures that serve as "triggers" for complement activation, e.g., antigen-antibody complexes, foreign structures found on microbial or artificial surfaces, etc.

"Concurrent administration" as used herein with respect to two or more agents, e.g., therapeutic agents, is administration performed using doses and time intervals such that the administered agents are present together within the body, e.g., at one or more sites of action in the body, over a time interval in non-negligible quantities. The time interval can be minutes (e.g., at least 1 minute, 1-30 minutes, 30-60 minutes), hours (e.g., at least 1 hour, 1-2 hours, 2-6 hours, 6-12 hours, 12-24 hours), days (e.g., at least 1 day, 1-2 days, 2-4 days, 4-7 days, etc.), weeks (e.g., at least 1, 2, or 3 weeks, etc. Accordingly, the agents may, but need not be, administered together as part of a single composition. In addition, the agents may, but need not be, administered essentially simultaneously (e.g., within less than 5 minutes, or within less than 1 minute apart) or within a short time of one another (e.g., less than 1 hour, less than 30 minutes, less than 10 minutes, approximately 5 minutes apart). According to various embodiments of the invention agents administered within such time intervals may be considered to be administered at substantially the same time. In certain embodiments of the invention concurrently administered agents are present at effective concentrations within the body (e.g., in the blood and/or at a site of local complement activation) over the time interval. When administered concurrently, the effective concentration of each of the agents needed to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. The non-negligible concentration of an agent may be, for example, less than approximately 5% of the concentration that would be required to elicit a particular biological response, e.g., a desired biological response.

An "effective amount" of an active agent such as a complement inhibitor refers to the amount of the active agent sufficient to elicit a desired biological response (or, equivalently, to inhibit an undesired biological response). As will be appreciated by those of ordinary skill in this art, the absolute amount of a particular agent that is effective may vary depending on such factors as the desired biological endpoint, the agent to be delivered, the target tissue, etc. Those of ordinary skill in the art will further understand that an "effective amount" may be administered in a single dose, or may be achieved by administration of multiple doses. For example, an effective amount may be an amount sufficient to relieve at least one symptom of a disorder. Depending on the particular disorder the symptom may be, e.g., pain, swelling, limitation of motion, cough, shortness of breath, hyperproliferation, itchiness, etc. An effective amount may be an amount sufficient to slow the progression of a chronic and progressive disorder, e.g., to increase the time before one or more symptoms or signs of the disorder manifests itself or to increase the time before the individual suffering from the disorder reaches a certain level of impairment. An effective amount may be an amount sufficient to allow faster or greater recovery from an injury than would occur in the absence of the agent.

"Fibrillar collagen solids" means the dry collagen solid content of fibrillar collagen. Fibrillar collagen is an insoluble collagen material wherein the collagen molecules interact to form microfibrils which themselves aggregate by side-to-side and end-to-end association to form stabilized collagen fibrils.

"Fusion protein" is used herein as in the art to refer to a polypeptide that contains two or more different polypeptides or portions thereof joined together to form a single polypeptide chain. A recombinant polynucleotide that encodes a fusion protein may be created by removing the stop codon from the polynucleotide that encodes the first polypeptide and appending a polynucleotide that encodes the second polypeptide in frame, so that the resulting recombinant polynucleotide encodes a single polypeptide comprising the two polypeptides.

"Identity" refers to the extent to which the sequence of two or more nucleic acids or polypeptides is the same. The percent identity between a sequence of interest and a second sequence over a window of evaluation, e.g., over the length of the sequence of interest, may be computed by aligning the sequences, determining the number of residues (nucleotides or amino acids) within the window of evaluation that are opposite an identical residue allowing the introduction of gaps to maximize identity, dividing by the total number of residues of the sequence of interest or the second sequence (whichever is greater) that fall within the window, and multiplying by 100. By gap is meant a portion of a sequence that is not occupied by a residue. For example, the sequence A K L - - - S I G (SEQ ID NO: 1) contains a gap of three residues. When computing the number of identical residues needed to achieve a particular percent identity, fractions are to be rounded to the nearest whole number. Percent identity can be calculated with the use of a variety of computer programs known in the art. For example, computer programs such as BLAST2, BLASTN, BLASTP, Gapped BLAST, etc., generate alignments and provide percent identity between a sequence of interest and sequences in any of a variety of public databases. The algorithm of Karlin and Altschul (Karlin and Altschul, *Proc. Natl. Acad. Sci. USA* 87:22264-2268, 1990) modified as in Karlin and Altschul, *Proc. Natl. Acad. Sci. USA* 90:5873-5877, 1993 is incorporated into the NBLAST and XBLAST programs of Altschul et al. (Altschul, et al., *J. Mol. Biol.* 215:403-410, 1990). To obtain gapped alignments for comparison purposes, Gapped BLAST is utilized as described in Altschul et al. (Altschul, et al. *Nucleic Acids Res.* 25: 3389-3402, 1997). When utilizing BLAST and Gapped BLAST programs, the default parameters of the respective programs may be used. A PAM250 or BLOSUM62 matrix may be used. See the Web site having URL www.ncbi.nlm.nih.gov for these programs. In a specific embodiment, percent identity of a sequence of interest and a second sequence is calculated using BLAST2 with default parameters.

The term "isolated" means 1) separated from at least some of the components with which it is usually associated in nature; 2) prepared or purified by a process that involves the hand of man; and/or 3) not occurring in nature. For example, a molecule that is removed from a cell that produces it is "isolated". A chemically synthesized molecule is "isolated".

The term "linked", when used with respect to two or more moieties, means that the moieties are physically associated or connected with one another to form a molecular structure that is sufficiently stable so that the moieties remain associated under the conditions in which the linkage is formed and, preferably, under the conditions in which the new molecular structure is used, e.g., physiological conditions. In certain preferred embodiments of the invention the linkage is a covalent linkage. In other embodiments the linkage is noncovalent. Moieties may be linked either directly or indirectly. When two moieties are directly linked, they are either covalently bonded to one another or are in sufficiently close proximity such that intermolecular forces between the two moieties maintain their association. When two moieties are indirectly linked, they are each linked either covalently or noncovalently to a third moiety, which maintains the association between the two moieties. In general, when two moieties are referred to as being linked by a "linker" or "linking moiety" or "linking portion", the linkage between the two linked moieties is indirect, and typically each of the linked moieties is covalently bonded to the linker. The linker can be any suitable moiety that reacts with the two moieties to be linked within a reasonable period of time, under conditions consistent with stability of the moieties (which may be protected as appropriate, depending upon the conditions), and in sufficient amount, to produce a reasonable yield.

"Liposomes" are artificial microscopic spherical particles formed by a lipid bilayer (or multilayers) enclosing an aqueous compartment. Liposomes can be used for delivering certain of the compositions of the invention.

"Local administration" or "local delivery", in reference to delivery of a composition or agent, refers to delivery that does not rely upon transport of the composition or agent to its intended target tissue or site via the vascular system. The composition or agent may be delivered directly to its intended target tissue or site, or in the vicinity thereof, e.g., in close proximity to the intended target tissue or site. For example, the composition may be delivered by injection or implantation of the composition or agent or by injection or implantation of a device containing the composition or agent. Following local administration in the vicinity of a target tissue or site, the composition or agent, or one or more components thereof, may diffuse to the intended target tissue or site. It will be understood that once having been locally delivered a fraction of a therapeutic agent (typically only a minor fraction of the administered dose) may enter the vascular system and be transported to another location, including back to its intended target tissue or site.

"Local complement activation" refers to complement activation that occurs outside the vascular system.

"Marker", for the purpose of the description of the invention, may refer to any molecular moiety (e.g., protein, peptide, mRNA or other RNA species, DNA, lipid, carbohydrate) that characterizes, indicates, or identifies a particular diseased or physiological state (e.g., apoptotic, cancerous, normal) or characterizes, indicates, or identifies one or more cell type(s), tissue type(s), or embryological origin. The presence or absence of certain marker(s), or the amount of certain marker(s), may indicate a particular physiological or diseased state of a patient, organ, tissue, or cell. A cellular marker is a marker found in or on a cell. A cellular marker may, but need not be, cell type specific. For example, a cell type specific marker is generally a protein, peptide, mRNA, lipid, or carbohydrate that is present at a higher level on or in a particular cell type or cell types of interest than on or in many other cell types. In some instances a cell type specific marker is present at detectable levels only on or in a particular cell type of interest. However, it will be appreciated that useful markers need not be absolutely specific for the cell type of interest. In general, a cell type specific marker for a particular cell type is expressed at levels at least 3 fold greater in that cell type than in a reference population of cells which may consist, for example, of a mixture containing cells from a plurality (e.g., 5-10 or more) of different tissues or organs in approximately equal amounts. The cell type specific marker may be present at levels at least 4-5 fold, between 5-10 fold, or more than 10-fold greater than its average expression in a reference population. Preferably detection or measurement of a cell type specific marker makes it possible to distinguish the cell type or types of interest from cells of many, most, or all other types. In general, the presence and/or abundance of most markers may be determined using standard techniques such as Northern blotting, in situ hybridization, RT-PCR, sequencing, immunological methods such as immunoblotting, immunodetection, or fluorescence detection following staining with fluorescently labeled antibodies, oligonucleotide or cDNA microarray or membrane array, protein microarray analysis, mass spectrometry, etc.

"Plurality" means more than one.

"Polypeptide", as used herein, refers to a polymer of amino acids, optionally including one or more amino acid analogs. A protein is a molecule composed of one or more polypeptides. A peptide is a relatively short polypeptide, typically between about 2 and 60 amino acids in length, e.g., between 8 and 40 amino acids in length. The terms "protein", "polypeptide", and "peptide" may be used interchangeably. Polypeptides used herein may contain amino acids such as those that are naturally found in proteins, amino acids that are not naturally found in proteins, and/or amino acid analogs that are not amino acids. As used herein, an "analog" of an amino acid may be a different amino acid that structurally resembles the amino acid or a compound other than an amino acid that structurally resembles the amino acid. A large number of art-recognized analogs of the 20 amino acids commonly found in proteins (the "standard" amino acids) are known. One or more of the amino acids in a polypeptide may be modified, for example, by the addition of a chemical entity such as a carbohydrate group, a phosphate group, a farnesyl group, an isofarnesyl group, a fatty acid group, a linker for conjugation, functionalization, or other modification, etc. Certain non-limiting suitable analogs and modifications are described in WO2004026328. The polypeptide may be acetylated, e.g., at the N-terminus and/or amidated, e.g., at the C-terminus.

The natural or other chemical modifications such as those described above can occur anywhere in a polypeptide, including the peptide backbone, the amino acid side-chains and the amino or carboxyl termini. A given polypeptide may contain many types of modifications. Polypeptides may be branched, for example, as a result of ubiquitination, and they may be cyclic, with or without branching. Polypeptides may be conjugated with, encapsulated by, or embedded within a polymer or polymeric matrix, dendrimer, nanoparticle, microparticle, liposome, or the like.

Polypeptides may, for example, be purified from natural sources, produced in vitro or in vivo in suitable expression systems using recombinant DNA technology in suitable expression systems (e.g., by recombinant host cells or in transgenic animals or plants), synthesized through chemical means such as conventional solid phase peptide synthesis and/or methods involving chemical ligation of synthesized peptides (see, e.g., Kent, S., *J Pept Sci.*, 9(9):574-93, 2003), or any combination of the foregoing. These methods are well known, and one of skill in the art will be able to select and implement an appropriate method for synthesizing the peptides and polypeptides described herein. A polypeptide may comprise one or more chemical ligation sites as described, for example, in U.S. Pub. No. 20040115774. In certain embodiments a polypeptide of the invention is modified with a polymer using one or more of the methods described or referenced therein.

The term "polypeptide sequence" or "amino acid sequence" as used herein can refer to the polypeptide material itself and is not restricted to the sequence information (i.e. the succession of letters or three letter codes chosen among the letters and codes used as abbreviations for amino acid names) that biochemically characterizes a polypeptide. A polypeptide sequence presented herein is presented in an N-terminal to C-terminal direction unless otherwise indicated.

"Pulmonary delivery", as used herein, refers to delivery to the respiratory tract. The "respiratory tract" encompasses the upper airways, including the oropharynx and larynx, followed by the lower airways, which include the trachea followed by bifurcations into the bronchi and bronchioli (e.g., terminal and respiratory). The terminal bronchioli divide into respiratory bronchioli which then lead to the alveoli.

"Purified", as used herein, means that an entity or substance is separated from one or more other entities or substances with which it was previously found before being purified. An entity or substance may be partially purified, substantially purified, or pure. A substance or entity such as a nucleic acid or polypeptide is considered pure when it is removed from substantially all other compounds or entities other than a solvent and any ions contained in the solvent, i.e., it constitutes at least about 90%, more preferably at least about 91%, 92%, 93%, 94%, 95%, 96%, 97%, 98%, 99%, or greater than 99% of the dry weight of the composition. A partially or substantially purified compound or entity such as a nucleic acid or polypeptide may be removed from at least 50%, at least 60%, at least 70%, or at least 80% by weight of the material with which it is naturally found, e.g., cellular material such as cellular proteins and/or nucleic acids. In certain embodiments the of a purified nucleic acid or polypeptide constitutes at least 10%, 20%, 30%, 40%, 50%, 60%, 70%, 80%, 90%, 95%, 99% or even more, by dry weight, of the total nucleic acid or polypeptide, respectively, in a composition. Methods for assessing purity are known in the art and include chromatographic methods, immunological methods, electrophoretic methods, etc. Any of the polynucleotides or polypeptides described herein may be purified.

"Reactive functional groups" as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those frequently used to prepare bioconjugates, e.g., N-hydroxysuccinimide esters, maleimides, sulfhydryls, and the like (see, for example, Hermanson, G., *Bioconjugate Techniques*, Academic press, San Diego, 1996). Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

The term "RNA interference" or "RNAi" is used herein as understood in the art, e.g., it refers to any method by which expression of a gene or gene product is decreased by introducing into a target cell or organism a double-stranded RNAs (dsRNA), referred to as an "RNAi agent" which corresponds in sequence to the gene of interest, particularly double-stranded RNAs containing a strand that is complementary to messenger RNA of the gene of interest. It will be appreciated that the RNAi agent may comprise one or more single-stranded portions, need not be 100% complementary to the target mRNA, and may comprise deoxyribonucleotides, non-naturally occurring or modified nucleotides, and modified backbone structures. Short interfering RNA (siRNA) are RNAi agents that typically comprise two separate RNA strands hybridized to form a duplex structure between 17-29 nt in length (usually about 19 nt in length), optionally with 3' overhangs of between 1-5 nt, typically 2 nt. Short hairpin RNAs are typically a single strand of RNA containing self-complementary regions that hybridize to form a duplex between 17-29 nt in length, e.g., about 19 nt long, connected by a single-stranded loop typically between 4-15 nt long, e.g., 6-9 nt long. "Introducing" may comprise exogenous administration of a dsRNA, e.g. siRNA, or may comprise causing the cell to either transiently or stably express an RNA that is processed intracellularly to yield an interfering RNA species such as an shRNA. For example, a vector comprising an expression cassette that encodes a short hairpin RNA (shRNA) may be introduced into cells. Optionally the vector is stably maintained in the cells. Virus vectors and plasmids are of use. Optionally the expression cassette integrates into the cellular genome. Design and synthesis of effective RNAi agents to inhibit expression of most genes is straightforward. Candidates can readily be tested to identify an agent with desired silencing efficiency.

"Sequential administration" of two or more agents refers to administration of two or more agents to a subject such that the agents are not present together in the subject's body, or at a relevant site of activity in the body, at greater than non-negligible concentrations. Administration of the agents may, but need not, alternate. Each agent may be administered multiple times.

"Specific binding" generally refers to a physical association between a target polypeptide (or, more generally, a target molecule) and a binding molecule such as an antibody or ligand. The association is typically dependent upon the presence of a particular structural feature of the target such as an antigenic determinant, epitope, binding pocket or cleft, recognized by the binding molecule. For example, if an antibody is specific for epitope A, the presence of a polypeptide containing epitope A or the presence of free unlabeled A in a reaction containing both free labeled A and the binding molecule that binds thereto, will reduce the amount of labeled A that binds to the binding molecule. It is to be understood that specificity need not be absolute but generally refers to the context in which the binding occurs. For example, it is well known in the art that numerous antibodies cross-react with other epitopes in addition to those present in the target molecule. Such cross-reactivity may be acceptable depending upon the application for which the antibody is to be used. One of ordinary skill in the art will be able to select antibodies or ligands having a sufficient degree of specificity to perform appropriately in any given application (e.g., for detection of a target molecule, for therapeutic purposes, etc). It is also to be understood that specificity may be evaluated in the context of additional factors such as the affinity of the binding molecule for the target versus the affinity of the binding molecule for other targets, e.g., competitors. If a binding molecule exhibits a high affinity for a target molecule that it is desired to detect and low affinity for nontarget molecules, the antibody will likely be an acceptable reagent. Once the specificity of a binding molecule is established in one or more contexts, it may be employed in other, preferably similar, contexts without necessarily re-evaluating its specificity. Binding of two or more molecules may be considered specific if the affinity (as measured by the equilibrium dissociation constant, Kd) is $10^{-3}$ M or less, preferably $10^{-4}$ M or less, more preferably $10^{-5}$ M or less, e.g., $10^{-6}$M or less, $10^{-7}$M or less, $10^{-8}$M or less, or $10^{-9}$M or less under the conditions tested, e.g., under physiological conditions.

"Significant sequence identity" as applied to an amino acid sequence means that the sequence is at least approximately 20%, 30%, 40%, 50%, 60%, 70%, 80%, 90%, or 95% identical to a reference sequence. In specific embodiments to an amino acid sequence means that the sequence is at least approximately 70%, 80%, 85%, 90%, 95%, 98%, or 99% identical to a reference sequence. In specific embodiments at least 20%, 30%, 40%, 50%, 60%, 70%, 80%, 90%, or 95% of the nonidentical amino acids are conservatively replaced relative to the reference sequence. Conservative replacements may be defined in accordance with Stryer, L., *Biochemistry*, 3rd ed., 1988, according to which amino acids in the following groups possess similar features with respect to side chain properties such as charge, hydrophobicity, aromaticity, etc. (1) Aliphatic side chains: G, A, V, L, I; (2) Aromatic side chains: F, Y, W; (3) Sulfur-containing side chains: C, M; (4) Aliphatic hydroxyl side chains: S, T; (5) Basic side chains: K, R, H; (6) Acidic amino acids: D, E, N, Q; (7) Cyclic aliphatic side chain: P, which may be considered to fall within group (1). In another accepted classification, conservative substitutions occur within the following groups: (1) Non-polar: A, L, I, V, G, P, F, W, M; (2) Polar: S, T, C, Y, N, Q. (3) Basic: K, R, H; (4) Acidic: D, E. Amino acids with a small side chain (G, A, S, T, M) also form a group from among which conservative substitutions can be made. Other classification methods known in the art can be used. Furthermore, amino acid analogs and unnatural amino acids can be classified in accordance with these schemes.

"Subject", as used herein, refers to an individual to whom an agent is to be delivered, e.g., for experimental, diagnostic, and/or therapeutic purposes. Preferred subjects are mammals, particularly domesticated mammals (e.g., dogs, cats, etc.), non-human primates, or humans.

"Supramolecular complex" refers to an assembly comprising at least two entities that are physically associated with one another, in which one or more entities is not covalently linked to another entity but is instead associated with that entity by through one or more noncovalent interactions mechanisms such as ionic interactions, hydrogen bonds, hydrophobic interactions, π-stacking, dative bonds, etc. For example, one or more entities may be entrapped, embedded, enclosed, or encapsulated within another entity, or entangled with another entity, or dissolved in another entity, or impregnated with another entity, or adsorbed to another entity, or bound to another entity, so as to maintain a physical association between the entities. The entities may be naturally occurring or synthetic. They may be, for example, polypeptides, non-polypeptide polymers, nucleic acids, lipids, small molecules, carbohydrates, etc. One or more of the entities may be a rigid or flexible polymer scaffold, a three-dimensional structure such as a microparticle, nanoparticle, liposome, noisome, dendrimer, etc. The supramolecular complex can contain any number or combination of molecules and/or other entities.

"Sustained release", also referred to "extended release" or "controlled release" formulation is used herein in a broad sense to mean a formulation of a biologically active agent, e.g., a therapeutic agent, resulting in the release or delivery of the agent for a sustained or extended period of time, or at least for a period of time which is longer than if the agent was made available in vivo in its native or unformulated state. Optionally, release or delivery of the agent occurs either continuously or intermittently so as to provide an effective amount of the agent to the subject, e.g., to provide an effective concentration at an extravascular location in the body, over a prolonged period of time e.g., at least 4, 8, 12, or 18 hours, at least 1, 2, 4, or 6 weeks, at least 1, 2, 3, 4, 6, 8, 10, 12, 15, 18, or 24 months, or longer. The formulation may comprise an active agent and one or more additional substances, wherein the active agent and the other component(s) are formulated such that the composition provides sustained release of the active agent. In some embodiments, a sustained release formulation comprises a physical form of the active agent such as a crystalline form, conformer, aggregate, gel, or precipitate form, etc., whereby release or delivery of the agent occurs for a longer period of time than if the agent was made available in vivo in an alternate form, e.g., in an amorphous state, as a powder, etc. In some embodiments, the rate of release varies depending on the concentration at which the active agent is administered or depending on the amount administered. For example, administering a higher amount or concentration may cause formation of a precipitate that dissolves over time, thereby providing sustained release.

"Sustained release device" is used herein as in the art to refer to a device capable of containing and releasing an active agent or a composition comprising an active agent so as to provide sustained release of the active agent. The term "sustained release device" encompasses solid articles of manufacture that consist of or comprise a sustained release formulation, electrical and/or mechanical devices such as pumps, etc. The device may be implantable at an extravascular location in the body. A device may release the agent using means that rely on a power source, e.g., a battery or external power source, or without use of a power source. One of skill in the art will appreciate that "sustained release device" does not refer to means of providing prolonged delivery of the agent from a supply of the agent located outside the body such as by prolonged injection or infusion.

"Systemic", as used herein in reference to complement components, refers to complement proteins that are synthesized by liver hepatocytes and enter the bloodstream, or are synthesized by circulating macrophages or monocytes and secreted into the bloodstream.

"Systemic complement activation" is complement activation that occurs in the blood, plasma, or serum and/or involves activation of systemic complement proteins at many locations throughout the body, affecting many body tissues, systems, or organs.

"Systemic administration" and like terms are used herein consistently with their usage in the art to refer to administration of an agent such that the agent becomes widely distributed in the body in significant amounts and has a biological effect, e.g., its desired effect, in the blood and/or reaches its desired site of action via the vascular system. Typical systemic routes of administration include administration by (i) introducing the agent directly into the vascular system or (ii) oral, pulmonary, or intramuscular administration wherein the agent is absorbed, enters the vascular system, and is carried to one or more desired site(s) of action via the blood.

"Therapeutic agent" is used herein to refer to any pharmacologically active agent useful for treating a disorder. The term includes any pharmaceutically acceptable salt, prodrug, salt of a prodrug, and such derivatives of such an agent as are known in the art or readily produced using standard methods known in the art. "Prodrug" refers to a precursor of an agent, wherein the prodrug is not itself pharmacologically active (or has a lesser or different activity than the desired activity of the drug) but is converted, following administration (e.g., by metabolism) into the pharmaceutically active drug. A therapeutic agent can be, without limitation, a small molecule or a biological macromolecule such as a polypeptide, antibody, or nucleic acid such as an aptamer, RNAi agent such as a small interfering RNA (siRNA), etc. A therapeutic agent is sometimes referred to as an "active agent" or "drug" herein.

"Treating", as used herein, refers to providing treatment, i.e., providing any type of medical or surgical management of a subject. The treatment can be provided in order to reverse, alleviate, inhibit the progression of, prevent or reduce the likelihood of a disease, disorder, or condition, or in order to reverse, alleviate, inhibit or prevent the progression of, prevent or reduce the likelihood of one or more symptoms or manifestations of a disease, disorder or condition. "Prevent" refers to causing a disease, disorder, condition, or symptom or manifestation of such not to occur for at least a period of time in at least some individuals. Treating can include administering an agent to the subject following the development of one or more symptoms or manifestations indicative of a complement-mediated condition, e.g., in order to reverse, alleviate, reduce the severity of, and/or inhibit or prevent the progression of the condition and/or to reverse, alleviate, reduce the severity of, and/or inhibit or one or more symptoms or manifestations of the condition. A composition of this invention can be administered to a subject who has developed a complement-mediated disorder or is at increased risk of developing such a disorder relative to a member of the general population. A composition of this invention can be administered prophylactically, i.e., before development of any symptom or manifestation of the condition. Typically in this case the subject will be at risk of developing the condition.

A "variant" of a particular polypeptide or polynucleotide has one or more alterations (e.g., additions, substitutions, and/or deletions, which may be referred to collectively as "mutations") with respect to the polypeptide or nucleic acid, which may be referred to as the "original polypeptide or polynucleotide". Thus a variant can be shorter or longer than the polypeptide or polynucleotide of which it is a variant. The terms "variant" encompasses "fragments". A "fragment" is a continuous portion of a polypeptide that is shorter than the original polypeptide. In certain embodiments of the invention a variant polypeptide has significant sequence identity to the original polypeptide over a continuous portion of the variant that comprises at least 50%, preferably at least 60%, at least 70%, at least 80%, at least 90%, at least 95%, or more, of the length of the variant or the length of the polypeptide, (whichever is shorter). In certain embodiments of the invention a variant polypeptide has substantial sequence identity to the original polypeptide over a continuous portion of the variant that comprises at least 50%, preferably at least 60%, at least 70%, at least 80%, at least 90%, at least 95%, or more, of the length of the variant or the length of the polypeptide, (whichever is shorter). In a non-limiting embodiment a variant has at least 80% identity to the original sequence over a continuous portion of the variant that comprises between 90% and 100% of the variant, e.g., over 100% of the length of the variant or the length of the polypeptide, (whichever is shorter). In another non-limiting embodiment a variant has at least 80% identity to the original sequence over a continuous portion of the variant that comprises between 90% and 100% of the variant, e.g., over 100% of the length of the variant or the length of the polypeptide, (whichever is shorter). In specific embodiments the sequence of a variant polypeptide has N amino acid differences with respect to an original sequence, wherein N is any integer between 1 and 10. In other specific embodiments the sequence of a variant polypeptide has N amino acid differences with respect to an original sequence, wherein N is any integer between 1 and 20. An amino acid "difference" refers to a substitution, insertion, or deletion of an amino acid.

In certain embodiments of the invention a fragment or variant possesses sufficient structural similarity to the original polypeptide so that when its 3-dimensional structure (either actual or predicted structure) is superimposed on the structure of the original polypeptide, the volume of overlap is at least 70%, preferably at least 80%, more preferably at least 90% of the total volume of the structure of the original polypeptide. A partial or complete 3-dimensional structure of the fragment or variant may be determined by crystallizing the protein, which can be done using standard methods. Alternately, an NMR solution structure can be generated, also using standard methods. A modeling program such as MODELER (Sali, A. and Blundell, T L, *J. Mol. Biol.*, 234, 779-815, 1993), or any other modeling program, can be used to generate a predicted structure. If a structure or predicted structure of a related polypeptide is available, the model can be based on that structure. The PROSPECT-PSPP suite of programs can be used (Guo, J T, et al., *Nucleic Acids Res.* 32 (Web Server issue):W522-5, Jul. 1, 2004).

Preferably one, more than one, or all biological functions or activities of a variant or fragment is substantially similar to that of the corresponding biological function or activity of the original molecule. In certain embodiments the activity of a variant or fragment may be at least 20%, at least 50%, at least 60%, at least 70%, at least 80%, or at least 90% of the activity of the original molecule, up to approximately 100%, approximately 125%, or approximately 150% of the activity of the original molecule. In certain embodiments an activity of a variant or fragment is such that the amount or concentration of the variant needed to produce an effect is within 0.5 to 5-fold of the amount or concentration of the original molecule needed to produce that effect.

As used herein, "alkyl" refers to a saturated straight, branched, or cyclic hydrocarbon having from about 1 to about 22 carbon atoms (and all combinations and subcombinations of ranges and specific numbers of carbon atoms therein), with from about 1 to about 12, or about 1 to about 7 carbon atoms being preferred in certain embodiments of the invention. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl.

As used herein, "halo" refers to F, Cl, Br or I.

As used herein, "aryl" refers to an optionally substituted, mono- or bicyclic aromatic ring system having from about 5 to about 14 carbon atoms (and all combinations and subcombinations of ranges and specific numbers of carbon atoms therein), with from about 6 to about 10 carbons being preferred. Non-limiting examples include, for example, phenyl and naphthyl.

As used herein, "aralkyl" refers to alkyl radicals bearing an aryl substituent and have from about 6 to about 22 carbon atoms (and all combinations and subcombinations of ranges and specific numbers of carbon atoms therein), with from about 6 to about 12 carbon atoms being preferred in certain embodiments. Aralkyl groups can be optionally substituted. Non-limiting examples include, for example, benzyl, naphthylmethyl, diphenylmethyl, triphenylmethyl, phenylethyl, and diphenylethyl.

As used herein, the terms "alkoxy" and "alkoxyl" refer to an optionally substituted alkyl-O-group wherein alkyl is as previously defined. Exemplary alkoxy and alkoxyl groups include methoxy, ethoxy, n-propoxy, i-propoxy, n-butoxy, and heptoxy.

As used herein, "carboxy" refers to a —C(=O)OH group.

As used herein, "alkoxycarbonyl" refers to a —C(=O)O-alkyl group, where alkyl is as previously defined.

As used herein, "aroyl" refers to a —C(=O)-aryl group, wherein aryl is as previously defined. Exemplary aroyl groups include benzoyl and naphthoyl.

Typically, substituted chemical moieties include one or more substituents that replace hydrogen. Exemplary substituents include, for example, halo, alkyl, cycloalkyl, aralkyl, aryl, sulfhydryl, hydroxyl (—OH), alkoxyl, cyano (—CN), carboxyl (—COOH), —C(=O)O-alkyl, aminocarbonyl (—C(=O)NH$_2$), —N-substituted aminocarbonyl (—C(=O)NHR"), CF$_3$, CF$_2$CF$_3$, and the like. In relation to the aforementioned substituents, each moiety R" can be, independently, any of H, alkyl, cycloalkyl, aryl, or aralkyl, for example.

As used herein, "L-amino acid" refers to any of the naturally occurring levorotatory alpha-amino acids normally present in proteins or the alkyl esters of those alpha-amino acids. The term D-amino acid" refers to dextrorotatory alpha-amino acids. Unless specified otherwise, all amino acids referred to herein are L-amino acids.

As used herein, an "aromatic amino acid" is an amino acid that comprises at least one aromatic ring, e.g., it comprises an aryl group.

As used herein, an "aromatic amino acid analog" is an amino acid analog that comprises at least one aromatic ring, e.g., it comprises an aryl group.

DETAILED DESCRIPTION OF CERTAIN EMBODIMENTS OF THE INVENTION

Inhibiting Local Complement Activation

The present invention relates to improved approaches for the use of complement inhibitors to treat a variety of disorders. "Complement inhibitor" is used herein as in the art to refer to a compound that inhibits expression or one or more biological activities of a complement component. As is known in the art, the soluble proteins of the complement system are synthesized primarily by liver hepatocytes and are present in large amounts in the blood, constituting collectively about 5% of total serum globulin. The invention encompasses the recognition that systemic complement inhibition, which has been tested or suggested as a therapeutic strategy in a number of complement-mediated disorders, has certain drawbacks that limit its usefulness in a clinical setting in at least some of these disorders. Indeed the failure to translate systemic complement inhibition strategies to effective use in the clinic in certain chronic disorders has been a source of frustration and disappointment to the biomedical research and medical communities.

The present invention is based in part on the inventors' recognition that (i) soluble complement proteins are produced locally in a variety of disorders; (ii) most or all systemic complement proteins do not readily extravasate and participate in complement activation outside of the vasculature unless there has been damage to the vasculature, and (iii) activation of locally produced complement proteins, including locally produced soluble complement proteins, plays a significant role in disease pathology and symptoms, often exceeding the role played by activation of systemic complement. Without wishing to be bound by any theory, the inventors propose that attempts to inhibit complement activation systemically, e.g., by intravascular administration of a complement inhibitor, have the following drawbacks: (i) The presence of large amounts of soluble complement proteins in the blood makes it difficult to achieve an effective serum concentration of complement inhibitors that act on those proteins, especially in the face of their ongoing synthesis by the liver, unless the complement inhibitor is administered by continuous or frequently repeated intravascular delivery. Such routes are often simply not practical for many chronic conditions in which complement activation plays a role, especially if managed primarily in an outpatient setting. (ii) Certain complement inhibitors, while effective in vitro, are rapidly cleared from the vascular system when administered systemically. (iii) Local complement activation involving locally produced soluble complement proteins frequently takes place in bodily compartments that are not accessible to large therapeutic agents such as antibodies and polypeptides unless the condition is so severe that the integrity of vessel walls and/or other barriers is disrupted. Hence even if systemic complement is effectively inhibited, such inhibition may not be sufficient to alleviate disease pathology or symptoms. As a result, improvement in the disorder may paradoxically lead to reduced effectiveness of systemically administered complement inhibitors. Based in part on the recognition of the afore-mentioned reasons for the limited success enjoyed by complement inhibition to date in certain conditions, the present invention provides compositions and methods that effectively harness the potential of complement inhibition as a strategy for treating a variety of complement-mediated disorders, particularly disorders that persist intermittently or continuously for months or years.

The invention provides novel and non-obvious formulations of complement inhibitors, and methods for their use. Certain of the methods comprise local administration of a complement inhibitor to an extravascular location in the body where complement activation occurs. Certain of the methods comprise administration of a sustained release formulation comprising a complement inhibitor to an extravascular location in the body where complement activation occurs. In some embodiments of the invention, the extravascular location is a discrete chamber, cavity, or compartment, such as a joint space, or joint cavity, of a synovial joint. The chamber, cavity, or compartment may be at least in part lined with, or may contain, a tissue on which complement exerts undesirable effects in a complement-mediated disorder. In some embodiments, the tissue does not directly contact the interior of the space but is sufficiently close to it that the complement inhibitor can readily diffuse into the extracellular fluid bathing the tissue. For example, the tissue may be located within 10-20 mm, in some embodiments within 5 mm-10 mm, within 1 mm-5 mm, within 0.5 mm-1 mm, within 0.1 mm-0.5 mm, or within less than 0.1 mm from the lining of the compartment, and not separated from it by a barrier that would substantially inhibit diffusion of the complement inhibitor to the tissue. The tissue may be one where complement activation exerts pathogenic effects in a complement-mediated disorder. For example, and without limitation, the tissue may be retinal tissue or synovial membrane. In some embodiments of the invention the extravascular location is more diffuse, e.g., the skin.

While local production of complement proteins has been observed in various disorders such as arthritis, and sporadic or single dose local administration of certain complement inhibiting agents has been explored (Williams, A S et al, *Br. J. Rheumatol.*, 35: 719-724; Linton, S and Morgan, B P, *Mol. Immunol.*, 36:905-914, 1999; Neumann, E., et al., *Arthritis & Rheumatism*, 46(4): 934-945, 2002), the present disclosure is believed to be the first to focus squarely on, and accord appropriate recognition to, the important role played by local complement activation in a wide variety of different diseases and on the therapeutic potential of sustained local complement inhibition for treating these disorders and at the same time provide a wide variety of compositions and methods for use in these disorders. The present disclosure is also believed to be the first to focus squarely on, and accord appropriate recognition to, the important role played by locally produced soluble complement proteins and/or cell surface receptors in a wide variety of different diseases and on the therapeutic potential for sustained local inhibition of these locally produced complement components for treating complement-mediated disorders and at the same time provide a wide variety of compositions and methods for use in these disorders.

The inventors propose that local inhibition of complement activation at or in an extravascular location over a prolonged period of time (e.g., about 1-4 weeks, 1-3 months, 3-6 months, 6-12 months, 12-24 months) will offer opportunities to alleviate and even inhibit progression of and/or symptom recurrence in chronic inflammatory diseases. Of course the invention is not limited to chronic diseases and may find use in a variety of acute settings such as infections in which excessive complement activation has pathogenic consequences. In some embodiments of the invention a complement inhibitor is delivered in a sustained manner such that complement activation is continuously inhibited over a prolonged period of time at or in an extravascular location. Thus in certain embodiments the local administration provides sustained local inhibition of complement activation. For example, local complement activation may be inhibited for a period of between 1 week and 1 year by a single administration of a sustained release formulation of the invention. In certain embodiments local complement activation is inhibited by at least 25%, 50%, 75%, 90%, 95%, or more for a period of between 2 weeks and 3 months by a single administration of a sustained release formulation of the invention. In certain embodiments local complement activation is inhibited by at least 25%, 50%, 75%, 90%, 95%, or more for a period of between 3 and 6 months by a single administration of a sustained release formulation of the invention. In certain embodiments local complement activation is inhibited by at least 25%, 50%, 75%, 90%, 95%, or more for a period of between 6 and 12 months by a single administration of a sustained release formulation of the invention. Multiple administrations can be performed. Individual administrations may occur on a regular schedule or as symptoms arise or recur. In certain embodiments administration occurs on average once every 4 weeks for at least a year. In certain embodiments administration occurs on average once every 3 months for at least a year. For example, an appropriate dose of a compstatin analog may be selected to achieve an average or steady state concentration in the extravascular location at least sufficient to bind to 50%, 60%, 70%, 80%, 90%, 95%, or more of the C3 present.

In certain embodiments of the invention a composition is administered multiple times, e.g. at least two times, separated by a time period, wherein said period is longer than the time at which the complement inhibitor is present at a concentration at least half its peak concentration in said extravascular location. In certain embodiments of the invention a composition is administered multiple times, e.g. at least two times, separated by a time period, wherein said period is longer than the half-life of the complement inhibitor at said extravascular location, or longer than the half-life of the complement inhibitor in vitro in a fluid of the type present at said extravascular location. The pattern of administration may be followed for as long as necessary to achieve a beneficial effect. The time period may be, e.g., about equal to the half-life, about 2, 5, 10, or 20 times the half-life, etc. The aforesaid patterns of administration may be followed for as long as necessary to achieve a beneficial effect.

Certain compositions and methods of the invention are based in part on the inventors' insight that it may not be necessary, or even desirable, to fully inhibit complement activation in an extravascular location afflicted by a complement-mediated disorder. In certain embodiments of the invention the level of complement activation in an extravascular location of interest is reduced to a level within a factor of about 2 times the average level present in that location in individuals not suffering from or at increased risk of developing the disorder, over any of the afore-mentioned time periods. In certain embodiments the level of complement activation in an extravascular location of interest is reduced to a level no more than 10% greater, no more than 25% greater, or no more than 50% greater than the average level present in that location in individuals not suffering from or at increased risk of developing the disorder, over any of the afore-mentioned time periods. In some embodiments of the invention, the relevant levels are measured in the fluid contained in a membrane-bound compartment (e.g., synovial fluid found in a joint cavity). In some embodiments of the invention, the relevant levels are measured in the tissue lining of a compartment (e.g., the synovial membrane).

Certain methods of the invention involve administering a complement inhibitor directly to an extravascular location that is a site of local complement activation in a complement-mediated disorder. In certain embodiments the methods involve inhibiting local formation of the MAC. In certain embodiments the methods involve inhibiting local activation of C3, C5, or factor B. In certain embodiments the methods involve inhibiting local complement activation mediated by the classical pathway. In certain embodiments the methods involve inhibiting local complement activation mediated by the alternative pathway. In certain embodiments the methods involve inhibiting local complement activation mediated by the lectin pathway. In certain embodiments the methods involve inhibiting local complement activation mediated by at least two pathways, e.g. the classical and alternative pathways.

The compositions and methods of the present invention are of use for treating a variety of complement-mediated disorders in which local complement activation and/or activity of one or more locally produced complement proteins plays a role. A wide variety of disorders having an inflammatory component may be treated according to the present invention. Exemplary disorders include disorders of the respiratory system, nervous system (which term as used herein excludes the eye), musculoskeletal system, and integumentary system. In certain embodiments the disorder of the musculoskeletal system is a disorder affecting cartilage. Disorders affecting cartilage typically result in symptoms of pain, stiffness and/or limitation of motion of the affected body parts. Examples include inflammatory joint conditions (e.g., arthritis such as rheumatoid arthritis or psoriatic arthritis, juvenile chronic arthritis, spondyloarthropathies Reiter's syndrome, gout). Inflammatory myopathies including dermatomyositis, polymyositis and others are disorders of chronic muscle inflammation of unknown etiology resulting in muscle weakness. Muscle injury/inflammation is often symmetric and progressive. Other conditions treated according to the present invention include disorders of the respiratory system such as chronic obstructive pulmonary disease (COPD, such as chronic bronchitis and emphysema), asthma, adult respiratory distress syndrome, sarcoid, allergic bronchopulmonary aspergillosis, hypersensitivity pneumonia, eosinophilic pneumonia, allergic bronchitis, sarcoid, infections such as influenza virus infection, respiratory syncytial virus (RSV) infection, parainfluenza virus (PIV) infection, rhinovirus (RV) infection and adenovirus infection; conditions affecting the skin such as psoriasis, pemphigus, systemic lupus erythematosus, scleroderma, allergic dermatitis, eczema; conditions affecting the central nervous system (CNS) and/or peripheral nervous system (PNS) such as spinal cord injury, trauma, multiple sclerosis or other demyelinating diseases, chronic pain, stroke, allergic neuritis, and Parkinson's and Alzheimer's diseases. The invention encompasses treatment of thyroiditis, which may occur due to a variety of causes. Thyroiditis includes post-partum thyroiditis, Hashimoto's thyroiditis, and Graves' disease. It will be appreciated that many of these conditions affect multiple organ systems, and the classification herein is in no way limiting.

The extravascular location is selected as appropriate for the disorder being treated. For example, if the condition is arthritis the complement inhibitor may be administered directly to a joint (e.g., into a joint space) or in the vicinity of a joint. See, e.g., FIG. 1 where the arrow indicates the interior of the synovial cavity of a typical synovial joint. Examples of intraarticular joints where the formulations of the invention can be administered include hip, knee, elbow, wrist, sternoclavicular, temperomandibular, carpal, tarsal, ankle, and any other joint subject to arthritic conditions. The formulations of the invention are also suitable for administration to bursae. Examples of bursae to which the formulations of the invention can be administered include acromial, bicipitoradial, cubitoradial, deltoid, infrapatellar, ischial, and other bursae known to those skilled in the art.

If the condition is asthma the complement inhibitor may be administered directly to the respiratory tract. If the condition is spinal cord injury the complement inhibitor may be administered intrathecally. If the condition affects the skin the complement inhibitor may be applied topically to the surface of the skin or injected, e.g., intradermally into or near a lesion. In some embodiments a composition of the invention is administered to the eye and a composition of the invention, which may be the same or different, is administered to at least one other extravascular location. In some embodiments a composition of the invention is not administered to the eye. It is noted that a location such as the respiratory system, skin, etc., is considered an "extravascular location" even though it contains blood vessels, provided that the complement inhibitor is not delivered directly into a vessel. "In the vicinity of" typically refers to a location no more than 10 cm away from at least a portion of the desired site of activity of the complement inhibitor.

In certain embodiments of the invention a complement inhibitor is formulated using methods and delivery systems conventionally used in the art to administer therapeutic agents to extravascular locations. In certain embodiments of the invention the method and delivery system is one that has been used previously to deliver a therapeutic agent other than a complement inhibitor to an extravascular location contemplated by the present invention. In certain embodiments of the invention the method and/or delivery system have been known or used previously in the art for sustained release of a therapeutic agent other than a complement inhibitor. In certain embodiments of the invention the method and/or delivery system have been known or used previously in the art for sustained release of a therapeutic agent other than a complement inhibitor to an extravascular location contemplated by the present invention. In certain embodiments of the invention the method and/or delivery system have been known or used previously in the art for sustained release of a therapeutic agent to an extravascular location, and the present contemplates sustained release at a different extravascular location. Thus certain embodiments of the present invention relate to novel and nonobvious uses for existing delivery methods and systems and/or to novel sustained release formulations comprising a complement inhibitor and, optionally, one or more additional active agents. In certain embodiments the methods and delivery systems are specifically adapted for delivery of a complement inhibitor as described elsewhere herein.

In certain embodiments of the invention the methods involve inhibiting activation of at least one locally produced soluble complement protein. The protein may be, e.g., C1, C3, C5, factor B, or factor D. In certain embodiments of the invention the methods involve inhibiting activation of at least one locally produced complement receptor protein. In certain embodiments of the invention the locally produced complement receptor protein is a receptor for C3a. In certain embodiments of the invention the locally produced complement receptor protein is a receptor for C5a.

In some embodiments of the invention the locally produced soluble complement protein is produced by synoviocytes. In some embodiments the locally produced soluble complement protein or receptor is produced by fibroblasts. In some embodiments the locally produced soluble complement protein or receptor is produced by chondrocytes. In some embodiments the locally produced soluble complement protein or receptor is produced by alveolar type II cells. In some embodiments the locally produced soluble complement protein or receptor is produced by keratinocytes. In some embodiments the locally produced soluble complement protein or receptor is produced by neurons. In some embodiments the locally produced soluble complement protein or receptor is produced by glial cells. In some embodiments the locally produced soluble complement protein or receptor is produced by tissue macrophages or monocytes. These cells may be normally resident at the location or may be recruited there in subjects suffering from the disorder. In certain embodiments the locally produced soluble complement protein or receptor is produced by other immune system cells such as activated T cells.

One aspect of the invention is novel sustained release formulations and devices for local administration of a therapeutic agent to the eye, and methods of use thereof to treat a variety of disorders that affect the eye. In some embodiments the subject has a disorder that affects the eye and at least one other body system or organ such as a joint. In some embodiments the disorder is an inflammatory eye disorder. In some embodiments the disorder is characterized by macular degeneration, e.g., the disorder is age-related macular degeneration (AMD). In some embodiments the disorder is wet type AMD. In some embodiments the disorder is dry type AMD. In some embodiments a composition of the invention is administered to an eye that exhibits geographic atrophy. In some embodiments the eye exhibits choroidal neovascularization. In some embodiments the disorder is diabetic retinopathy. In some embodiments the eye disorder is anterior or posterior uveitis or keratitis. Further information about these and other eye disorders treatable using compositions and methods of the invention is found in copending patent applications U.S. Ser. No. 60/760,974, U.S. Ser. No. 11/247,886, U.S. Ser. No. 11/544,389, and U.S. Ser. No. 11/612,751. In some embodiments the composition is administered to the posterior chamber. In some embodiments the composition is administered intravitreally. In some embodiments the composition is administered transsclerally. Further information about these and other delivery methods suitable for administered composition of the invention are found in the afore-mentioned patent applications.

In some embodiments a sustained release formulation of this invention and an angiogenesis inhibitor are administered to an eye that exhibits choroidal neovascularization (CNV) and/or retinal neovascularization (RNV). For example, the subject to whom the composition is administered may suffer from wet (exudative) AMD. The sustained release formulation may be administered prior to, at essentially the same time as, or following administration of the angiogenesis inhibitor. In some embodiments the angiogenesis inhibitor is administered, and a sustained release formulation or device comprising a complement inhibitor is administered after a time interval. The time interval may be, e.g., up to 1, 2, or 4 weeks after administration of the angiogenesis inhibitor, or up to 2 or 3 months after administration of the angiogenesis inhibitor. In some embodiments a sustained release formulation or device comprising a complement inhibitor is administered after the subject experiences an improvement in visual acuity and/or exhibits reduced retinal thickness and/or reduced blood vessel leakage in the eye (e.g., as measured using optical coherence tomography or fluorescein angiography).

A variety of angiogenesis inhibitors are of use. In certain embodiments of the invention the angiogenesis inhibitor binds to one or more vascular endothelial growth factor (VEGF) isoforms or receptors. The angiogenesis inhibitor may be one that is recognized in the art as useful for treating AMD and/or CNV or RNV due to other causes). The angiogenesis inhibit is an antibody or antibody fragment such as Avastin® or Lucentis®, or an aptamer such as Macugen® in various embodiments of the invention. The angiogenesis inhibitor can be used in standard doses and routes of administration for such agents (e.g., intravitreal administration). In some embodiments an angiogenesis inhibitor and a complement inhibitor are administered in the same or different sustained release formulations or devices.

In certain embodiments of the present invention a complement-mediated disorder is treated without significantly inhibiting activation of systemic complement. In some embodiments "without significantly inhibiting activation of systemic complement" means that systemic complement activation (e.g., as measured in the blood) is maximally inhibited by less than 20% on average as assessed, for example, using an art-accepted assay such as those described herein, e.g., a clinically accepted assay for complement activation during the course of therapy. In some embodiments local administration of a complement inhibitor has essentially no detectable effect on systemic complement activation as assessed, for example, using an art-accepted assay such as those described herein, e.g., a clinically accepted assay for complement activation. In some embodiments local administration of a complement inhibitor transiently inhibits systemic complement activation. For example in some embodiments local administration of a complement inhibitor reduces systemic complement activation by no more than 1%, 2%, 5%, 10%, or 20% for no more than 1, 2, 6, 12, 24, or 48 hours. In exemplary embodiments local administration of a complement inhibitor reduces systemic complement activation by no more than 10% for no more than 24 or 48 hours. In exemplary embodiments local administration of a complement inhibitor reduces systemic complement activation by no more than 20% for no more than 24 or no more than 48 hours. In some embodiments local administration of a complement inhibitor does not result in a statistically significant alteration in the incidence and/or severity of an adverse effect attributable to systemic complement inhibition (e.g., susceptibility to infection or severity of infection).

In exemplary embodiments, the complement inhibitor is released from a sustained release formulation or device in an amount sufficient to produce a clinically significant reduction in severity at least one symptom of the disorder being treated for a desired average time, wherein said amount is not sufficient to significantly inhibit systemic complement activity of at least one complement activation pathway during at least 50% of said time. In some embodiments, said time is at least 1 week. In some embodiments, said time is at least 2, 4, 6, or 8 weeks. In some embodiments, said amount is not sufficient to significantly inhibit systemic complement activity of at least one complement activation pathway during at least 60%, 70%, 80%, 90%, or 95% of said time. In some embodiments, said amount is not sufficient to significantly inhibit systemic complement activity of at least one complement activation pathway (e.g., in various embodiments the classical, alternative, lectin pathway, or any combination thereof) during all or essentially all (e.g., at least 99%) of said time.

It should be noted that the invention does not exclude systemic complement inhibition and, in some embodiments, specifically includes systemic complement inhibition. For example, in some embodiments systemic complement activation is initially inhibited on a relatively short term basis while local complement activation is inhibited over a longer time period by local administration of a complement inhibitor once or on a repeated basis. In representative embodiments a complement inhibitor is administered systemically either once or multiple times such that systemic complement activation is inhibited by at least 25%, 50%, 75%, 90%, 95%, or more for a period of up to 24, 48, or 72 hours, or for a period of between 72 hours and 1 week, or for a period of between 1-4 weeks. Either the same or a different complement inhibitor is administered locally to one or more extravascular sites of local complement activation. Local administration may take place prior to, during, and/or following the time period during which systemic inhibition occurs. Suitable time frames for local complement inhibition are described above and elsewhere herein.

A variety of different complement inhibitors are of use in the present invention. Complement inhibitors of use in this invention fall into a number of compound classes including peptides, polypeptides, antibodies, small molecules, and nucleic acids (e.g., aptamers, RNAi agents such as short interfering RNAs). Complement inhibitors include antagonists of one or more proteins in the classical, alternative, and/or lectin pathway. In certain embodiments of the invention the complement inhibitor inhibits an enzymatic activity of a complement protein. The enzymatic activity may be proteolytic activity, such as ability to cleave another complement protein. In certain embodiments of the invention the complement inhibitor inhibits cleavage of C3, C5, or factor B.

One aspect of the present invention is selection of complement inhibitors having suitable molecular weight and other characteristics so as to allow release of the agent in an extravascular location, e.g., in a compartment such as a joint space, or the spinal canal, in amounts sufficient to effectively inhibit local complement activation. In certain embodiments the agent has a molecular weight no more than 2, 5, or 10 kilodaltons in order to permit a high molar concentration of the agent in a suitable volume of a sustained release formulation. In certain embodiments the complement inhibitor does not comprise an antibody or fragment thereof. In certain embodiments of the invention the complement inhibitor does not comprise a soluble complement receptor. For example, in certain embodiments the complement inhibitor does not consist of or comprises a soluble C1 receptor or a portion thereof capable of binding to C1.

In certain embodiments the complement inhibitor is selected to be stable in the extravascular location, e.g., extravascular compartment such as a joint space, to which it is delivered. For example in certain embodiments the inhibitor is selected to be stable in synovial fluid. In certain embodiments the inhibitor is selected to be stable in cerebrospinal fluid. In certain embodiments a compound is "stable" if it has a half-life of at least 12, 24, 48, 60, 72, 96 hours or one that falls within in any intervening subrange or has specific value between 12 and 96 hours. In certain embodiments "half-life" refers to half-life in vitro, which reflects degradation rate. In certain embodiments "half-life" refers to half-life in vivo, which reflects rates of both degradation and clearance from the relevant extravascular location. Stability can be measured in vitro using a suitable biological assay or detection means such as an HPLC assay.

One important aspect of the present invention is the recognition that effective local complement inhibiting strategies benefit from, and may in some instances even require, the use of sustained release to achieve therapeutic effects sufficient to warrant their adoption in clinical practice. Accordingly, in certain embodiments of the invention the complement inhibitor is selected to be stable in a sustained release formulation or device and under conditions compatible with preparation of a sustained release formulation or device. Selection of suitable complement inhibitors for sustained release formulation and delivery is one aspect of this invention.

In certain embodiments the methods comprise locally administering a complement inhibitor that binds to and directly inhibits a locally produced soluble complement protein. In certain embodiments the methods comprise locally administering a complement inhibitor that indirectly inhibits a locally produced soluble complement protein, i.e., the complement inhibitor inhibits the protein by a mechanism other than binding to it. For example, the complement inhibitor may enzymatic activity of an upstream component of the complement cascade that would otherwise activate the locally produced soluble complement protein.

Suitable amounts of the complement inhibitor can be selected by determining the level of complement proteins and/or complement activation in an extravascular compartment of interest, e.g. a symptomatic joint in a subject with arthritis, or other extravascular location. The determination could be made on the basis of measurements made in multiple subjects or measurements made in an individual subject to be treated. In some embodiments a sample is obtained from the extravascular compartment of interest of a subject to be treated, e.g., a sample of fluid from a joint space, and the concentration of one or more complement protein(s) or degree of complement activation determined. Intact complement protein(s) and/or fragments thereof could be measured.

In certain embodiments of the invention an appropriate dosage of a complement inhibitor or sustained release formulation or device comprising a complement inhibitor is selected based at least in part on this information and, optionally by estimating a total amount of complement protein using the approximate volume of the compartment. For example, in one embodiment the concentration of a locally produced soluble complement protein is determined in a fluid sample obtained from an extravascular location. An appropriate dose of a complement inhibitor that binds to the complement protein is selected to achieve an average or steady state concentration of the inhibitor in the compartment at least sufficient to bind to 50%, 60%, 70%, 80%, 90%, 95%, or more of the protein present in excess of that found in the extravascular location in the absence of the disorder. In certain embodiments the dose is selected to achieve an average or steady state concentration of the inhibitor in the compartment at least sufficient to bind to 50%, 60%, 70%, 80%, 90%, 95%, or more of the protein present in the compartment. In certain embodiments the dose is selected to achieve an average or steady state concentration equal to 1, 2, 5, 10, 20, 50, or any intervening subrange between 1 and 50, times as great as that of the complement protein. In certain embodiments of the invention an average or steady state concentration of the inhibitor is present for a prolonged period of time, e.g., 1-4 weeks, 4-6 weeks, 1-3 months, 3-6 months, 6-12 months, 12-24 months. In certain embodiments of the invention the dose is adjusted to account for the fact that prior to administering the complement inhibitor, the target complement protein was being consumed, resulting in a lower measured level than would be the case once the complement cascade is inhibited. The sustained release formulation or device can be selected to provide an appropriate release rate to achieve the desired average or steady state concentration.

The invention provides a unit dosage of the sustained release formulations and devices described herein comprising, typically in a container, a sufficient amount of the formulation or device to produce a desired therapeutic effect in a patient, i.e., a sufficient amount for a single administration to a patient in need thereof. In one embodiment, the unit dosage is sterile and lyophilized. In another embodiment the unit dosage is sterile and prepared as a solution acceptable for administration to a patient, e.g., by injection, perfusion, or infiltration. In another embodiment the unit dosage is a suspension or dispersion in a liquid suitable for administration to a patient, e.g., by injection, infiltration, etc. In another embodiment the unit dosage form is a selected mass or volume of nanoparticles or microparticles comprising a complement inhibitor, optionally in a liquid carrier. In another embodiment the unit dosage form is a macroscopic article of manufacture suitable for insertion or implantation into a patient and containing a selected amount of a complement inhibitor.

The following sections discuss certain exemplary complement inhibitors of use in the present invention. The invention may be practiced with other complement inhibitors known in the art.

Compounds that Inhibit C3 Activation or Activity

In certain embodiments of the invention the complement inhibitor inhibits activation of C3. Exemplary compounds include compounds, e.g., peptides, that bind to C3 and inhibit its cleavage. In embodiments of particular interest the compound is a compstatin analog. Compstatin is a 13 amino acid cyclic peptide whose sequence was derived from that of a longer peptide identified using phage display that binds to complement component C3 and inhibits complement activation. Compstatin inhibits cleavage of C3 to C3a and C3b by convertase. Since C3 is a central component of all three pathways of complement activation, compstatin and analogs thereof are able to inhibit activation of the converging protein of all three pathways. Without wishing to be bound by any theory, the ability of compstatin and analogs thereof to inhibit the alternative pathway of complement activation may contribute significantly to efficacy in certain of the disorders described herein.

The invention encompasses the recognition that compstatin and analogs thereof possess unique and unexpected advantages as compared with other complement inhibitors, particularly for sustained release, in a variety of disorders. The relatively low molecular weight (~1.6 kD), stability, and various other properties of compstatin analogs facilitate their incorporation into sustained delivery formulations and devices suitable for providing therapeutic concentrations to a variety of extravascular tissues. Furthermore, compstatin analogs are highly specific. The invention encompasses the recognition that, for this and other reasons, compstatin analogs are expected to have a number of significant advantages for use in chronic disorders in which patients may typically be exposed to a therapeutic agent over a prolonged period of time and/or in which therapeutic preparations may need to be stored for extended periods of time. In certain embodiments a compstatin analog is delivered in a sustained manner over a prolonged period of time such as 1-2 weeks, 2-4 weeks, 4-6 weeks, 1-3 months, 3-6 months, 6-12 months, 1-2 years, 2-5 years, or 5-10 years.

The invention provides a method of inhibiting complement activation in an extravascular location of a subject comprising administering a compstatin analog to the subject in an amount effective to detectably inhibit complement activation in the extravascular location of the subject over a period of at least 1-2 weeks, 2-4 weeks, 4-6 weeks, e.g., 1-3 months, 3-6 months, 6-12 months, 12-24 months, 24-36 months, etc. In certain embodiments of the invention the compstatin analog is administered by one or more injections into an extravascular location. In certain embodiments of the invention the compstatin analog is administered by release from a sustained release formulation such as microparticles, nanoparticles, or a gel. The compstatin analog may be released by diffusion out of the formulation or may be released as the formulation degrades. The treatment may be repeated multiple times. In certain embodiments the administration is performed at intervals of, on average, every 2 weeks, every month, every 1-3 months, every 3-6 months, every 6-12 months, or every 12-24 months. In certain embodiments the sustained release formulation is biodegradable. In certain embodiments the effective concentration is between 10% and 250% of the average concentration of C3 in a fluid in the extravascular location of subjects suffering from the disorder.

Compstatin's amino acid sequence is described in U.S. Pat. No. 6,319,897, which is incorporated herein by reference (see SEQ ID NO: 2 in U.S. Pat. No. 6,319,897). The sequence, Ile-[Cys-Val-Val-Gln-Asp-Trp-Gly-His-His-Arg-Cys]-Thr (SEQ ID NO: 43), with the disulfide bond between the two cysteines denoted by brackets is an N-terminal cyclic region of a larger peptide (SEQ ID NO: 1 in U.S. Pat. No. 6,319,897) that also shows complement inhibiting activity. A number of fragments and variants of this peptide inhibit complement, some of them having a higher inhibitory activity than compstatin itself, and are of use in the compositions and methods of the present invention. See, e.g. SEQ ID NOs: 13, 15, 20, 21, and 22 in U.S. Pat. No. 6,319,897. It will be understood that the name "compstatin" was not used in U.S. Pat. No. 6,319,897 but was subsequently adopted in the scientific and patent literature (see, e.g., Morikis, et al., *Protein Sci.*, 7(3):619-27, 1998) to refer to a peptide having the same sequence as SEQ ID NO: 2 disclosed in U.S. Pat. No. 6,319,897, but amidated at the C terminus as shown in Table 1 (SEQ ID NO: 8). The term "compstatin" is used herein consistently with such usage (i.e., to refer to the cyclic peptide of SEQ ID NO: 8). In certain embodiments of the invention a peptide having higher complement inhibiting activity than compstatin, e.g., at least 5-fold higher activity, at least 10-fold higher activity, etc., is used.

A variety of compstatin analogs that have higher complement inhibiting activity than compstatin have been synthesized. Certain of these are described in WO2004/026328 (PCT/US2003/029653), Morikis, D., et al., *Biochem Soc Trans.* 32(Pt 1):28-32, 2004, Mallik, B., et al., *J. Med. Chem.*, 274-286, 2005, and/or in Katragadda, M., et al. *J. Med. Chem.*, 49: 4616-4622, 2006, all of which are incorporated herein by reference. Complement inhibiting peptides and peptidomimetics described therein can be used in the present invention. For example, SEQ ID NOs: 4-13 as described in WO2004/026328 can be used in the present invention.

Compstatin analogs may be acetylated or amidated, e.g., at the N-terminus and/or C-terminus. For example, compstatin analogs may be acetylated at the N-terminus and amidated at the C-terminus. Consistent with usage in the art, "compstatin" as used herein, and the activities of compstatin analogs described herein relative to that of compstatin, refer to compstatin amidated at the C-terminus (Mallik, 2005, supra).

Concatamers or multimers of compstatin or a complement inhibiting analog thereof (with appropriate modification of the N- and/or C-termini) are also of use in the present invention.

A supramolecular complex comprising compstatin and/or one or more complement inhibiting analogs thereof is of use in the methods of the invention.

As used herein, the term "compstatin analog" includes compstatin and any complement inhibiting analog thereof. The term "compstatin analog" encompasses compstatin and other compounds designed or identified based on compstatin and whose complement inhibiting activity is at least 50% as great as that of compstatin as measured, e.g., using any complement activation assay accepted in the art or substantially similar or equivalent assays. Certain compstatin analogs and suitable assays are described in U.S. Pat. No. 6,319,897, WO2004/026328, Morikis, supra, Mallik, supra, and/or Katragadda 2006, supra. The assay may, for example, measure alternative pathway-mediated erythrocyte lysis or be an ELISA assay (see Examples 5 and 6). WO2004/026328, Morikis, supra, Mallik, supra, Katragadda 2006, supra, among other references, describe compstatin analogs having higher activity than compstatin and methods for determining their ability to inhibit complement activation. The invention includes embodiments in which any one or more of the compstatin analogs or compositions described herein is used in any the methods of treatment described herein.

The activity of a compstatin analog may be expressed in terms of its $IC_{50}$ (the concentration of the compound that inhibits complement activation by 50%), e.g., at a particular plasma concentration, with a lower $IC_{50}$ indicating a higher activity as recognized in the art. The activity of a preferred compstatin analog for use in the present invention is at least as great as that of compstatin. Certain modifications are known to reduce or eliminate complement inhibiting activity and may be explicitly excluded from any embodiment of the invention. It will be appreciated that the precise $IC_{50}$ value measured for a given compstatin analog will vary with experimental conditions. Comparative values, in which $IC_{50}$ is determined for multiple compounds under substantially identical conditions, are of use.

In one embodiment, the $IC_{50}$ of the compstatin analog is no more than the $IC_{50}$ of compstatin. In certain embodiments of the invention the activity of the compstatin analog is between 2 and 99 times that of compstatin (i.e., the analog has an $IC_{50}$ that is less than the $IC_{50}$ of compstatin by a factor of between 2 and 99). For example, the activity may be between 10 and 50 times as great as that of compstatin, or between 50 and 99 times as great as that of compstatin. In certain embodiments of the invention the activity of the compstatin analog is between 99 and 264 times that of compstatin. For example, the activity may be 100, 110, 120, 130, 140, 150, 160, 170, 180, 190, 200, 210, 220, 230, 240, 250, 260, or 264 times as great as that of compstatin. In certain embodiments the activity is between 264 and 300, 300 and 350, 350 and 400, or 400 and 500 times as great as that of compstatin. The invention further contemplates compstatin analogs having activities between 500 and 1000 times that of compstatin.

The $K_d$ of compstatin binding to C3 has been measured as 1.3 µM using isothermal titration calorimetry (Katragadda, et al., *J. Biol. Chem.*, 279(53), 54987-54995, 2004). (It will be appreciated that in this paper and certain other papers in the scientific literature, the term "compstatin" was used to refer to compstatin and various analogs generally or to compstatin acetylated at the N terminus. The value of 1.3 µM was obtained for the acetylated version of SEQ ID NO: 8, i.e., SEQ ID NO: 9). Binding affinity of a variety of compstatin analogs for C3 has been correlated with their activity, with a lower $K_d$ indicating a higher binding affinity, as recognized in the art. A linear correlation between binding affinity and activity was shown for certain analogs tested (Katragadda, 2004, supra; Katragadda 2006, supra). In certain embodiments of the invention the compstatin analog binds to C3 with a $K_d$ of between 0.1 µM and 1.0 µM, between 0.05 µmM and 0.1 µM, between 0.025 µM and 0.05 µM, between 0.015 µM and 0.025 µM, between 0.01 µM and 0.015 µM, or between 0.001 µM and 0.01 µM. In certain embodiments the $IC_{50}$ of the compstatin analog is between about 0.2 µM and about 0.5 µM. In certain embodiments the $IC_{50}$ of the compstatin analog is between about 0.1 µM and about 0.2 µM. In certain embodiments the $IC_{50}$ of the compstatin analog is between about 0.05 µM and about 0.1 µM. In certain embodiments the $IC_{50}$ of the compstatin analog is between about 0.001 µM and about 0.05 µM.

Compounds "designed or identified based on compstatin" include, but are not limited to, compounds that comprise an amino acid chain whose sequence is obtained by (i) modifying the sequence of compstatin (e.g., replacing one or more amino acids of the sequence of compstatin with a different amino acid or amino acid analog, inserting one or more amino acids or amino acid analogs into the sequence of compstatin, or deleting one or more amino acids from the sequence of compstatin); (ii) selection from a phage display peptide library in which one or more amino acids of compstatin is randomized, and optionally further modified according to method (i); or (iii) identified by screening for compounds that compete with compstatin or any analog thereof obtained by methods (i) or (ii) for binding to C3 or a fragment thereof. Many useful compstatin analogs comprise a hydrophobic cluster, a β-turn, and a disulfide bridge.

In certain embodiments of the invention the sequence of the compstatin analog comprises or consists essentially of a sequence that is obtained by making 1, 2, 3, or 4 substitutions in the sequence of compstatin, i.e., 1, 2, 3, or 4 amino acids in the sequence of compstatin is replaced by a different standard amino acid or by a non-standard amino acid. In certain embodiments of the invention the amino acid at position 4 is altered. In certain embodiments of the invention the amino acid at position 9 is altered. In certain embodiments of the invention the amino acids at positions 4 and 9 are altered. In certain embodiments of the invention only the amino acids at positions 4 and 9 are altered. In certain embodiments of the invention the amino acid at position 4 or 9 is altered, or in certain embodiments both amino acids 4 and 9 are altered, and in addition up to 2 amino acids located at positions selected from 1, 7, 10, 11, and 13 are altered. In certain embodiments of the invention the amino acids at positions 4, 7, and 9 are altered. In certain embodiments of the invention amino acids at position 2, 12, or both are altered, provided that the alteration preserves the ability of the compound to be cyclized. Such alteration(s) at positions 2 and/or 12 may be in addition to the alteration(s) at position 1, 4, 7, 9, 10, 11, and/or 13. Optionally the sequence of any of the compstatin analogs whose sequence is obtained by replacing one or more amino acids of compstatin sequence further includes up to 1, 2, or 3 additional amino acids at the C-terminus. In one embodiment, the additional amino acid is Gly. Optionally the sequence of any of the compstatin analogs whose sequence is obtained by replacing one or more amino acids of compstatin sequence further includes up to 5, or up to 10 additional amino acids at the C-terminus. It should be understood that compstatin analogs may have any one or more of the characteristics or features of the various embodiments described herein, and characteristics or features of any embodiment may additionally characterize any other embodiment described herein, unless otherwise stated or evident from the context. In certain embodiments of the invention the sequence of the compstatin analog comprises or consists essentially of a sequence identical to that of compstatin except at positions corresponding to positions 4 and 9 in the sequence of compstatin.

Compstatin and certain compstatin analogs having somewhat greater activity than compstatin contain only standard amino acids ("standard amino acids" are glycine, leucine, isoleucine, valine, alanine, phenylalanine, tyrosine, tryptophan, aspartic acid, asparagine, glutamic acid, glutamine, cysteine, methionine, arginine, lysine, proline, serine, threonine and histidine). Certain compstatin analogs having improved activity incorporate one or more non-standard amino acids. Useful non-standard amino acids include singly and multiply halogenated (e.g., fluorinated) amino acids, D-amino acids, homo-amino acids, N-alkyl amino acids, dehydroamino acids, aromatic amino acids (other than phenylalanine, tyrosine and tryptophan), ortho-, meta- or para-aminobenzoic acid, phospho-amino acids, methoxylated amino acids, and α,α-disubstituted amino acids. In certain embodiments of the invention, a compstatin analog is designed by replacing one or more L-amino acids in a compstatin analog described elsewhere herein with the corresponding D-amino acid. Such compounds and methods of use thereof are an aspect of the invention. Exemplary non-standard amino acids of use include 2-naphthylalanine (2-NaI), 1-naphthylalanine (1-NaI), 2-indanylglycine carboxylic acid (2Ig1), dihydrotrpytophan (Dht), 4-benzoyl-L-phenylalanine (Bpa), 2-α-aminobutyric acid (2-Abu), 3-α-aminobutyric acid (3-Abu), 4-α-aminobutyric acid (4-Abu), cyclohexylalanine (Cha), homocyclohexylalanine (hCha), 4-fluoro-L-tryptophan (4fW), 5-fluoro-L-tryptophan (5fW), 6-fluoro-L-tryptophan (6fW), 4-hydroxy-L-tryptophan (4OH—W), 5-hydroxy-L-tryptophan (5OH—W), 6-hydroxy-L-tryptophan (6OH—W), 1-methyl-L-tryptophan (1MeW), 4-methyl-L-tryptophan (4MeW), 5-methyl-L-tryptophan (5MeW), 7-aza-L-tryptophan (7aW), α-methyl-L-tryptophan (αMeW), β-methyl-L-tryptophan (βMeW), N-methyl-L-tryptophan (NMeW), ornithine (orn), citrulline, norleucine, γ-glutamic acid, etc.

In certain embodiments of the invention the compstatin analog comprises one or more Trp analogs (e.g., at position 4 and/or 7 relative to the sequence of compstatin). Exemplary Trp analogs are mentioned above. See also Beene, et. al. *Biochemistry* 41: 10262-10269, 2002 (describing, inter alia, singly- and multiply-halogenated Trp analogs); Babitzke & Yanofsky, *J. Biol. Chem.* 270: 12452-12456, 1995 (describing, inter alia, methylated and halogenated Trp and other Trp and indole analogs); and U.S. Pat. Nos. 6,214,790, 6,169,057, 5,776,970, 4,870,097, 4,576,750 and 4,299,838. Other Trp analogs include variants that are substituted (e.g., by a methyl group) at the α or β carbon and, optionally, also at one or more positions of the indole ring. Amino acids comprising two or more aromatic rings, including substituted, unsubstituted, or alternatively substituted variants thereof, are of interest as Trp analogs.

In certain embodiments the Trp analog has increased hydrophobic character relative to Trp. For example, the indole ring may be substituted by one or more alkyl (e.g., methyl) groups. In certain embodiments the Trp analog participates in a hydrophobic interaction with C3. Such a Trp analog may be located, e.g., at position 4 relative to the sequence of compstatin. In certain embodiments the Trp analog comprises a substituted or unsubstituted bicyclic aromatic ring component or two or more substituted or unsubstituted monocyclic aromatic ring components.

In certain embodiments the Trp analog has increased propensity to form hydrogen bonds with C3 relative to Trp but does not have increased hydrophobic character relative to Trp. The Trp analog may have increased polarity relative to Trp and/or an increased ability to participate in an electrostatic interaction with a hydrogen bond donor on C3. Certain exemplary Trp analogs with an increased hydrogen bond forming character comprise an electronegative substituent on the indole ring. Such a Trp analog may be located, e.g., at position 7 relative to the sequence of compstatin.

In certain embodiments of the invention the compstatin analog comprises one or more Ala analogs (e.g., at position 9 relative to the sequence of compstatin), e.g., Ala analogs that are identical to Ala except that they include one or more $CH_2$ groups in the side chain. In certain embodiments the Ala analog is an unbranched single methyl amino acid such as 2-Abu. In certain embodiments of the invention the compstatin analog comprises one or more Trp analogs (e.g., at position 4 and/or 7 relative to the sequence of compstatin) and an Ala analog (e.g., at position 9 relative to the sequence of compstatin).

In certain embodiments of the invention the compstatin analog is a compound that comprises a peptide that has a sequence of (X'aa)$_n$-Gln-Asp-Xaa-Gly-(X"aa)$_m$, (SEQ ID NO: 2) wherein each X'aa and each X"aa is an independently selected amino acid or amino acid analog, wherein Xaa is Trp or an analog of Trp, and wherein n>1 and m>1 and n+m is between 5 and 21. The peptide has a core sequence of Gln-Asp-Xaa-Gly, where Xaa is Trp or an analog of Trp, e.g., an analog of Trp having increased propensity to form hydrogen bonds with an H-bond donor relative to Trp but, in certain embodiments, not having increased hydrophobic character relative to Trp. For example, the analog may be one in which the indole ring of Trp is substituted with an electronegative moiety, e.g., a halogen such as fluorine. In one embodiment Xaa is 5-fluorotryptophan. Absent evidence to the contrary, one of skill in the art would recognize that any non-naturally occurring peptide whose sequence comprises this core sequence and that inhibits complement activation and/or binds to C3 will have been designed based on the sequence of compstatin. In an alternative embodiment Xaa is an amino acid or amino acid analog other than a Trp analog that allows the Gln-Asp-Xaa-Gly peptide to form a β-turn.

In certain embodiments of the invention the peptide has a core sequence of X'aa-Gln-Asp-Xaa-Gly (SEQ ID NO: 3), where X'aa and Xaa are selected from Trp and analogs of Trp. In certain embodiments of the invention the peptide has a core sequence of X'aa-Gln-Asp-Xaa-Gly (SEQ ID NO: 3), where X'aa and Xaa are selected from Trp, analogs of Trp, and other amino acids or amino acid analogs comprising at least one aromatic ring. In certain embodiments of the invention the core sequence forms a β-turn in the context of the peptide. The β-turn may be flexible, allowing the peptide to assume two or more conformations as assessed for example, using nuclear magnetic resonance (NMR). In certain embodiments X'aa is an analog of Trp that comprises a substituted or unsubstituted bicyclic aromatic ring component or two or more substituted or unsubstituted monocyclic aromatic ring components. In certain embodiments of the invention X'aa is selected from the group consisting of 2-napthylalanine, 1-napthylalanine, 2-indanylglycine carboxylic acid, dihydrotryptophan, and benzoylphenylalanine. In certain embodiments of the invention X'aa is an analog of Trp that has increased hydrophobic character relative to Trp. For example, X'aa may be 1-methyltryptophan. In certain embodiments of the invention Xaa is an analog of Trp that has increased propensity to form hydrogen bonds relative to Trp but, in certain embodiments, not having increased hydrophobic character relative to Trp. In certain embodiments of the invention the analog of Trp that has increased propensity to form hydrogen bonds relative to Trp comprises a modification on the indole ring of Trp, e.g., at position 5, such as a substitution of a halogen atom for an H atom at position 5. For example, Xaa may be 5-fluorotryptophan.

In certain embodiments of the invention the peptide has a core sequence of X'aa-Gln-Asp-Xaa-Gly-X"aa (SEQ ID NO: 4), where X'aa and Xaa are each independently selected from Trp and analogs of Trp and X"aa is selected from His, Ala, analogs of Ala, Phe, and Trp. In certain embodiments of the invention X'aa is an analog of Trp that has increased hydrophobic character relative to Trp, such as 1-methyltryptophan or another Trp analog having an alkyl substituent on the indole ring (e.g., at position 1, 4, 5, or 6). In certain embodiments X'aa is an analog of Trp that comprises a substituted or unsubstituted bicyclic aromatic ring component or two or more substituted or unsubstituted monocyclic aromatic ring components. In certain embodiments of the invention X'aa is selected from the group consisting of 2-napthylalanine, 1-napthylalanine, 2-indanylglycine carboxylic acid, dihydrotryptophan, and benzoylphenylalanine. In certain embodiments of the invention Xaa is an analog of Trp that has increased propensity to form hydrogen bonds with C3 relative to Trp but, in certain embodiments, not having increased hydrophobic character relative to Trp. In certain embodiments of the invention the analog of Trp that has increased propensity to form hydrogen bonds relative to Trp comprises a modification on the indole ring of Trp, e.g., at position 5, such as a substitution of a halogen atom for an H atom at position 5. For example, Xaa may be 5-fluorotryptophan. In certain embodiments X"aa is Ala or an analog of Ala such as Abu or another unbranched single methyl amino acid. In certain embodiments of the invention the peptide has a core sequence of X'aa-Gln-Asp-Xaa-Gly-X"aa (SEQ ID NO: 4), where X'aa and Xaa are each independently selected from Trp, analogs of Trp, and amino acids or amino acid analogs comprising at least one aromatic side chain, and X"aa is selected from His, Ala, analogs of Ala, Phe, and Trp. In certain embodiments X"aa is selected from analogs of Trp, aromatic amino acids, and aromatic amino acid analogs.

In certain preferred embodiments of the invention the peptide is cyclic. The peptide may be cyclized via a bond between any two amino acids, one of which is (X'aa)$_n$ and the other of which is located within (X"aa)$_m$. In certain embodiments the cyclic portion of the peptide is between 9 and 15 amino acids in length, e.g., 10-12 amino acids in length. In certain embodiments the cyclic portion of the peptide is 11 amino acids in length, with a bond (e.g., a disulfide bond) between amino acids at positions 2 and 12. For example, the peptide may be 13 amino acids long, with a bond between amino acids at positions 2 and 12 resulting in a cyclic portion 11 amino acids in length.

In certain embodiments the peptide comprises or consists of the sequence X'aa1-X'aa2-X'aa3-X'aa4-Gln-Asp-Xaa-Gly-X"aa1-X"aa2-X"aa3-X"aa4-X"aa5 (SEQ ID NO: 5). In certain embodiments X'aa4 and Xaa are selected from Trp and analogs of Trp, and X'aa1, X'aa3, X"aa1, X"aa2, X"aa3, X"aa4, and X"aa5 are independently selected from among amino acids and amino acid analogs. In certain embodiments X'aa4 and Xaa are selected from aromatic amino acids and aromatic amino acid analogs. Any one or more of X'aa1, X'aa2, X'aa3, X"aa1, X"aa2, X"aa3, X"aa4, and X"aa5 may be identical to the amino acid at the corresponding position in compstatin. In one embodiment, X"aa1 is Ala or a single methyl unbranched amino acid. The peptide may be cyclized via a covalent bond between (i) X'aa1, X'aa2, or X'aa3; and (ii) X"aa2, X"aa3, X"aa4 or X"aa5. In one embodiment the peptide is cyclized via a covalent bond between X'aa2, and X"aa4. In one embodiment the covalently bound amino acid are each Cys and the covalent bond is a disulfide (S—S) bond. In other embodiments the covalent bond is a C—C, C—O, C—S, or C—N bond. In certain embodiments of the invention one of the covalently bound residues is an amino acid or amino acid analog having a side chain that comprises a primary or secondary amine, the other covalently bound residue is an amino acid or amino acid analog having a side chain that comprises a carboxylic acid group, and the covalent bond is an amide bond. Amino acids or amino acid analogs having a side chain that comprises a primary or secondary amine include lysine and diaminocarboxylic acids of general structure $NH_2(CH_2)_nCH(NH_2)COOH$ such as 2,3-diaminopropionic acid (dapa), 2,4-diaminobutyric acid (daba), and ornithine (orn), wherein n=1 (dapa), 2 (daba), and 3 (orn), respectively. Examples of amino acids having a side chain that comprises a carboxylic acid group include dicarboxylic amino acids such as glutamic acid and aspartic acid. Analogs such as beta-hydroxy-L-glutamic acid may also be used.

In certain embodiments, the compstatin analog is a compound that comprises a peptide having a sequence:

```
                                            (SEQ ID NO: 6)
Xaa1-Cys-Val-Xaa2-Gln-Asp-Xaa2*-Gly-Xaa3-His-Arg-
Cys-Xaa4;
``` wherein:
Xaa1 is Ile, Val, Leu, $B^1$-Ile, $B^1$-Val, $B^1$-Leu or a dipeptide comprising Gly-Ile or $B^1$-Gly-Ile, and $B^1$ represents a first blocking moiety;
Xaa2 and Xaa2* are independently selected from Trp and analogs of Trp;
Xaa3 is His, Ala or an analog of Ala, Phe, Trp, or an analog of Trp;
Xaa4 is L-Thr, D-Thr, Ile, Val, Gly, a dipeptide selected from Thr-Ala and Thr-Asn, or a tripeptide comprising Thr-Ala-Asn, wherein a carboxy terminal —OH of any of the L-Thr, D-Thr, Ile, Val, Gly, Ala, or Asn optionally is replaced by a second blocking moiety $B^2$; and the two Cys residues are joined by a disulfide bond.

In other embodiments Xaa1 is absent or is any amino acid or amino acid analog, and Xaa2, Xaa2*, Xaa3, and Xaa4 are as defined above. If Xaa1 is absent, the N-terminal Cys residue may have a blocking moiety $B^1$ attached thereto.

In another embodiment, Xaa4 is any amino acid or amino acid analog and Xaa1, Xaa2, Xaa2*, and Xaa3 are as defined above. In another embodiment Xaa4 is a dipeptide selected from the group consisting of: Thr-Ala and Thr-Asn, wherein the carboxy terminal OH or the Ala or Asn is optionally replaced by a second blocking moiety $B^2$.

In any of the embodiments of the compstatin analog of SEQ ID NO: 6, Xaa2 may be Trp.

In any of the embodiments of the compstatin analog of SEQ ID NO: 6, Xaa2 may be an analog of Trp comprising a substituted or unsubstituted bicyclic aromatic ring component or two or more substituted or unsubstituted monocyclic aromatic ring components. For example, the analog of Trp may be selected from 2-naphthylalanine (2-Nal), 1-naphthylalanine (1-Nal), 2-indanylglycine carboxylic acid (Ig1), dihydrotrpytophan (Dht), and 4-benzoyl-L-phenylalanine.

In any of the embodiments of the compstatin analog of SEQ ID NO: 6, Xaa2 may be an analog of Trp having increased hydrophobic character relative to Trp. For example, the analog of Trp may be selected from 1-methyltryptophan, 4-methyltryptophan, 5-methyltryptophan, and 6-methyltryptophan. In one embodiment, the analog of Trp is 1-methyltryptophan. In one embodiment, Xaa2 is 1-methyltryptophan, Xaa2* is Trp, Xaa3 is Ala, and the other amino acids are identical to those of compstatin.

In any of the embodiments of the compstatin analog of SEQ ID NO: 6, Xaa2* may be an analog of Trp such as an analog of Trp having increased hydrogen bond forming propensity with C3 relative to Trp, which, in certain embodiments, does not have increased hydrophobic character relative to Trp. In certain embodiments the analog of Trp comprises an electronegative substituent on the indole ring. For example, the analog of Trp may be selected from 5-fluorotryptophan and 6-fluorotryptophan.

In certain embodiments of the invention Xaa2 is Trp and Xaa2* is an analog of Trp having increased hydrogen bond forming propensity with C3 relative to Trp which, in certain embodiments, does not have increased hydrophobic character relative to Trp. In certain embodiments of the compstatin analog of SEQ ID NO: 6, Xaa2 is analog of Trp having increased hydrophobic character relative to Trp such as an analog of Trp selected from 1-methyltryptophan, 4-methyltryptophan, 5-methyltryptophan, and 6-methyltryptophan, and Xaa2* is an analog of Trp having increased hydrogen bond forming propensity with C3 relative to Trp which, in certain embodiments, does not have increased hydrophobic character relative to Trp. For example, in one embodiment Xaa2 is methyltryptophan and Xaa2* is 5-fluorotryptophan.

In certain of the afore-mentioned embodiments, Xaa3 is Ala. In certain of the afore-mentioned embodiments Xaa3 is a single methyl unbranched amino acid, e.g., Abu.

In certain embodiments the invention employs a compstatin analog of SEQ ID NO: 6, as described above, wherein Xaa2 and Xaa2* are independently selected from Trp, analogs of Trp, and other amino acids or amino acid analogs that comprise at least one aromatic ring, and Xaa is His, Ala or an analog of Ala, Phe, Trp, an analog of Trp, or another aromatic amino acid or aromatic amino acid analog.

In certain embodiments of the invention the blocking moiety present at the N- or C-terminus of any of the compstatin analogs described herein is any moiety that stabilizes a peptide against degradation that would otherwise occur in mammalian (e.g., human or non-human primate) blood or vitreous. For example, blocking moiety $B^1$ could be any moiety that alters the structure of the N-terminus of a peptide so as to inhibit cleavage of a peptide bond between the N-terminal amino acid of the peptide and the adjacent amino acid. Blocking moiety $B^2$ could be any moiety that alters the structure of the C-terminus of a peptide so as to inhibit cleavage of a peptide bond between the C-terminal amino acid of the peptide and the adjacent amino acid. Any suitable blocking moieties known in the art could be used. In certain embodiments of the invention blocking moiety $B^1$ comprises an acyl group (i.e., the portion of a carboxylic acid that remains following removal of the —OH group). The acyl group typically comprises between 1 and 12 carbons, e.g., between 1 and 6 carbons. For example, in certain embodiments of the invention blocking moiety $B^1$ is selected from the group consisting of: formyl, acetyl, proprionyl, butyryl, isobutyryl, valeryl, isovaleryl, etc. In one embodiment, the blocking moiety $B^1$ is an acetyl group, i.e., Xaa1 is Ac-Ile, Ac-Val, Ac-Leu, or Ac-Gly-Ile.

In certain embodiments of the invention blocking moiety $B^2$ is a primary or secondary amine (—$NH_2$ or —$NHR^1$, wherein R is an organic moiety such as an alkyl group).

In certain embodiments of the invention blocking moiety $B^1$ is any moiety that neutralizes or reduces the negative charge that may otherwise be present at the N-terminus at physiological pH. In certain embodiments of the invention blocking moiety B² is any moiety that neutralizes or reduces the negative charge that may otherwise be present at the C-terminus at physiological pH.

In certain embodiments of the invention, the compstatin analog is acetylated or amidated at the N-terminus and/or C-terminus, respectively. A compstatin analog may be acetylated at the N-terminus, amidated at the C-terminus, and or both acetylated at the N-terminus and amidated at the C-terminus. In certain embodiments of the invention a compstatin analog comprises an alkyl or aryl group at the N-terminus rather than an acetyl group.

In certain embodiments, the compstatin analog is a compound that comprises a peptide having a sequence:

(SEQ ID NO: 7)
Xaa1-Cys-Val-Xaa2-Gln-Asp-Xaa2*-Gly-Xaa3-His-Arg-Cys-Xaa4;

wherein:
Xaa1 is Ile, Val, Leu, Ac-Ile, Ac-Val, Ac-Leu or a dipeptide comprising Gly-Ile or Ac-Gly-Ile;
Xaa2 and Xaa2* are independently selected from Trp and analogs of Trp;
Xaa3 is His, Ala or an analog of Ala, Phe, Trp, or an analog of Trp;
Xaa4 is L-Thr, D-Thr, Ile, Val, Gly, a dipeptide selected from Thr-Ala and Thr-Asn, or a tripeptide comprising Thr-Ala-Asn, wherein a carboxy terminal —OH of any of L-Thr, D-Thr, Ile, Val, Gly, Ala, or Asn optionally is replaced by —NH₂; and
the two Cys residues are joined by a disulfide bond.

embodiments Xaa3 is a single methyl unbranched amino acid.

In certain embodiments of the invention Xaa1 is Ile and Xaa4 is L-Thr.

In certain embodiments of the invention Xaa1 is Ile, Xaa2* is Trp, and Xaa4 is L-Thr.

In certain embodiments the invention utilizes a compstatin analog of SEQ ID NO: 7, as described above, wherein Xaa2 and Xaa2* are independently selected from Trp, analogs of Trp, other amino acids or aromatic amino acid analogs, and Xaa3 is His, Ala or an analog of Ala, Phe, Trp, an analog of Trp, or another aromatic amino acid or aromatic amino acid analog.

In certain embodiments of any of the compstatin analogs described herein, Xaa3 is an analog of His.

Table 1 provides a non-limiting list of compstatin analogs useful in the present invention. The analogs are referred to in abbreviated form in the left column by indicating specific modifications at designated positions (1-13) as compared to the parent peptide, compstatin. Unless otherwise indicated, peptides are amidated at the C-terminus. Bold text is used to indicate certain modifications. Activity relative to compstatin is based on published data and assays described therein (WO2004/026326, Mallik, 2005; Katragadda, 2006). Where multiple publications reporting an activity were consulted, the more recently published value is used, and it will be recognized that values may be adjusted in the case of differences between assays. It will also be appreciated that the peptides listed in Table 1 are cyclized, e.g., via a disulfide bond between the two Cys residues when used in the therapeutic compositions and methods of the invention. Other methods of cyclizing the peptides may be used.

TABLE 1

| Peptide | Sequence | SEQ ID NO: | Activity over compstatin |
|---|---|---|---|
| Compstatin | $_H$-ICVVQDWGHHRCT-$_{CONH2}$ | 8 | * |
| Ac-compstatin | $_{Ac}$-ICVVQDWGHHRCT-$_{CONH2}$ | 9 | 3 × more |
| Ac-V4Y/H9A | $_{Ac}$-ICVYQDWGAHRCT-$_{CONH2}$ | 10 | 14 × more |
| Ac-V4W/H9A —OH | $_{Ac}$-ICVWQDWGAHRCT-$_{COOH}$ | 11 | 27 × more |
| Ac-V4W/H9A | $_{Ac}$-ICVWQDWGAHRCT-$_{CONH2}$ | 12 | 45 × more |
| Ac-V4W/H9A/T13dT —OH | $_{Ac}$-ICVWQDWGAHRCdT-$_{COOH}$ | 13 | 55 × more |
| Ac-V4(2-Nal)/H9A | $_{Ac}$-ICV**(2-Nal)QDWGA**HRCT-$_{CONH2}$ | 14 | 99 × more |
| Ac V4(2-Nal)/H9A —OH | $_{Ac}$-ICV**(2-Nal)QDWGA**HRCT-$_{COOH}$ | 15 | 38 × more |
| Ac V4(1-Nal)/H9A —OH | $_{Ac}$-ICV**(1-Nal)QDWGA**HRCT-$_{COOH}$ | 16 | 30 × more |
| Ac-V4 2Igl/H9A | $_{Ac}$-ICV**(2-Igl)QDWGA**HRCT-$_{CONH2}$ | 17 | 39 × more |
| Ac-V4 2Igl/H9A —OH | $_{Ac}$-ICV**(2-Igl)QDWGA**HRCT-$_{COOH}$ | 18 | 37 × more |
| Ac-V4Dht/H9A —OH | $_{Ac}$-ICVDhtQDWGAHRCT-$_{COOH}$ | 19 | 5 × more |
| Ac-V4(Bpa)/H9A —OH | $_{Ac}$-ICV**(Bpa)QDWGA**HRCT-$_{COOH}$ | 20 | 49 × more |
| Ac-V4(Bpa)/H9A | $_{Ac}$-ICV**(Bpa)QDWGA**HRCT-$_{CONH2}$ | 21 | 86 × more |
| Ac-V4(Bta)/H9A —OH | $_{Ac}$-ICV**(Bta)QDWGA**HRCT-$_{COOH}$ | 22 | 65 × more |
| Ac-V4(Bta)/H9A | $_{Ac}$-ICV**(Bta)QDWGA**HRCT-$_{CONH2}$ | 23 | 64 × more |
| Ac-V4W/H9(2-Abu) | $_{Ac}$-ICVWQDWG(2-Abu)HRCT-$_{CONH2}$ | 24 | 64 × more |
| +G/V4W/H9A + AN —OH | $_H$-GICVWQDWGAHRCTAN-$_{COOH}$ | 25 | 38 × more |
| Ac-V4(5fW)/H9A | $_{Ac}$-ICV**(5fW)QDWGA**HRCT-$_{CONH_2}$ | 26 | 31 × more |
| Ac-V4(5-MeW)/H9A | $_{Ac}$-ICV**(5-methyl-W)QDWGA**HRCT-$_{CONH_2}$ | 27 | 67 × more |
| Ac-V4(1-MeW)/H9A | $_{Ac}$-ICV**(1-methyl-W)QDWGA**HRCT-$_{CONH_2}$ | 28 | 264 × more |
| Ac-V4W/W7(5fW)/H9A | $_{Ac}$-ICVWQD**(5fW)GA**HRCT-$_{CONH_2}$ | 29 | 121 × more |
| Ac-V4(5fW)/W7(5tW)/H9A | $_{Ac}$-ICV**(5fW)QD(5fW)GA**HRCT-$_{CONH_2}$ | 30 | NA |
| Ac-V4(5-MeW)/W7(5fW)H9A | $_{Ac}$-ICV**(5-methyl-W)QD(5fW)GA**HRCT-$_{CONH_2}$ | 31 | NA |
| Ac-V4(1MeW)/W7(5fW)/H9A | $_{Ac}$-ICV**(1-methyl-W)QD(5fW)GA**HRCT-$_{CONH_2}$ | 32 | 264 × more |

NA = not available

Xaa1, Xaa2, Xaa2*, Xaa3, and Xaa4 are as described above for the various embodiments of SEQ ID NO: 6. For example, in certain embodiments Xaa2* is Trp. In certain embodiments Xaa2 is an analog of Trp having increased hydrophobic character relative to Trp, e.g., 1-methyltryptophan. In certain embodiments Xaa3 is Ala. In certain In certain embodiments of the compositions and methods of the invention the compstatin analog has a sequence selected from sequences 9-32. In certain embodiments of the compositions and methods of the invention the compstatin analog has a sequence selected from SEQ ID NOs: 14, 21, 28, 29, and 32. In certain embodiments of the compositions and methods of the invention the compstatin analog has a sequence selected from SEQ ID NO: 14. In certain embodiments of the compositions and methods of the invention the compstatin analog has a sequence selected from SEQ ID NOs: 30 and 31. In certain embodiments of the compositions and methods of the invention the compstatin analog has a sequence of SEQ ID NO: 28. In certain embodiments of the compositions and methods of the invention the compstatin analog has a sequence of SEQ ID NO: 29. In certain embodiments of the compositions and methods of the invention the compstatin analog has a sequence of SEQ ID NO: 32.

In other embodiments, compstatin analogs having sequences as set forth in Table 1, but where the Ac-group is replaced by an alternate blocking moiety $B^1$, as described above, are used. In other embodiments, compstatin analogs having sequences as set forth in Table 1, but where the —$NH_2$ group is replaced by an alternate blocking moiety $B^2$, as described above, are used.

In one embodiment, the compstatin analog binds to substantially the same region of the β chain of human C3 as does compstatin. In one embodiment the compstatin analog is a compound that binds to a fragment of the C-terminal portion of the β chain of human C3 having a molecular weight of about 40 kDa to which compstatin binds (Soulika, A. M., et al., *Mol. Immunol.*, 35:160, 1998; Soulika, A. M., et al., *Mol. Immunol.* 43(12):2023-9, 2006). In certain embodiments the compstatin analog is a compound that binds to the binding site of compstatin as determined in a compstatin-C3 structure, e.g., a crystal structure or NMR-derived 3D structure. In certain embodiments the compstatin analog is a compound that could substitute for compstatin in a compstatin-C3 structure and would form substantially the same intermolecular contacts with C3 as compstatin. In certain embodiments the compstatin analog is a compound that binds to the binding site of a peptide having a sequence set forth in Table 1, e.g., SEQ ID NO: 14, 21, 28, 29, or 32 in a peptide-C3 structure, e.g., a crystal structure. In certain embodiments the compstatin analog is a compound that binds to the binding site of a peptide having SEQ ID NO: 30 or 31 in a peptide-C3 structure, e.g., a crystal structure. In certain embodiments the compstatin analog is a compound that could substitute for the peptide of SEQ ID NO: 9-32, e.g., SEQ ID NO: 14, 21, 28, or 32 in a peptide-C3 structure and would form substantially the same intermolecular contacts with C3 as the peptide. In certain embodiments the compstatin analog is a compound that could substitute for the peptide of SEQ ID NO: 30 or 31 in a peptide-C3 structure and would form substantially the same intermolecular contacts with C3 as the peptide.

One of ordinary skill in the art will readily be able to determine whether a compstatin analog binds to a fragment of the C-terminal portion of the β chain of C3 using routine experimental methods. For example, one of skill in the art could synthesize a photocrosslinkable version of the compstatin analog by including a photo-crosslinking amino acid such as p-benzoyl-L-phenylalanine (Bpa) in the compound, e.g., at the C-terminus of the sequence (Soulika, A. M., et al, supra). Optionally additional amino acids, e.g., an epitope tag such as a FLAG tag or an HA tag could be included to facilitate detection of the compound, e.g., by Western blotting. The compstatin analog is incubated with the fragment and crosslinking is initiated. Colocalization of the compstatin analog and the C3 fragment indicates binding. Surface plasmon resonance may also be used to determine whether a compstatin analog binds to the compstatin binding site on C3 or a fragment thereof. One of skill in the art would be able to use molecular modeling software programs to predict whether a compound would form substantially the same intermolecular contacts with C3 as would compstatin or a peptide having the sequence of any of the peptides in Table 1, e.g., SEQ ID NO: 14, 21, 28, 29, or 32, or in other embodiments SEQ ID NO: 30 or 31.

Compstatin analogs may be prepared by various synthetic methods of peptide synthesis known in the art via condensation of amino acid residues, e.g., in accordance with conventional peptide synthesis methods, may be prepared by expression in vitro or in living cells from appropriate nucleic acid sequences encoding them using methods known in the art. For example, peptides may be synthesized using standard solid-phase methodologies as described in Malik, supra, Katragadda, supra, and/or WO2004026328. Potentially reactive moieties such as amino and carboxyl groups, reactive functional groups, etc., may be protected and subsequently deprotected using various protecting groups and methodologies known in the art. See, e.g., "Protective Groups in Organic Synthesis", $3^{rd}$ ed. Greene, T. W. and Wuts, P. G., Eds., John Wiley & Sons, New York: 1999. Peptides may be purified using standard approaches such as reversed-phase HPLC. Separation of diasteriomeric peptides, if desired, may be performed using known methods such as reversed-phase HPLC. Preparations may be lyophilized, if desired, and subsequently dissolved in a suitable solvent, e.g., water. The pH of the resulting solution may be adjusted, e.g. to physiological pH, using a base such as NaOH. Peptide preparations may be characterized by mass spectrometry if desired, e.g., to confirm mass and/or disulfide bond formation. See, e.g., Mallik, 2005, and Katragadda, 2006.

The structure of compstatin is known in the art, and NMR structures for a number of compstatin analogs having higher activity than compstatin are also known (Malik, supra). Structural information may be used to design compstatin mimetics. In one embodiment, the compstatin mimetic is any compound that competes with compstatin or any compstatin analog (e.g., a compstatin analog whose sequence is set forth in Table 1) for binding to C3 or a fragment thereof (such as a 40 kD fragment of the β chain to which compstatin binds) and that has an activity equal to or greater than that of compstatin. The compstatin mimetic may be a peptide, nucleic acid, or small molecule. In certain embodiments the compstatin mimetic is a compound that binds to the binding site of compstatin as determined in a compstatin-C3 structure, e.g., a crystal structure or a 3-D structure derived from NMR experiments. In certain embodiments the compstatin mimetic is a compound that could substitute for compstatin in a compstatin-C3 structure and would form substantially the same intermolecular contacts with C3 as compstatin. In embodiments the compstatin mimetic is a compound that binds to the binding site of a peptide having a sequence set forth in Table 1, e.g., SEQ ID NO: 14, 21, 28, 29, or 32, or in certain embodiments SEQ ID NO: 30 or 31, in a peptide-C3 structure. In certain embodiments the compstatin mimetic is a compound that could substitute for a peptide having a sequence set forth in Table 1, e.g., SEQ ID NO: 14, 21, 28, 29, or 32, or in certain embodiments SEQ ID NO: 30 or 31, in a peptide-C3 structure and would form substantially the same intermolecular contacts with C3 as the peptide. In certain embodiments the compstatin mimetic has a non-peptide backbone but has side chains arranged in a sequence designed based on the sequence of compstatin.

One of skill in the art will appreciate that once a particular desired conformation of a short peptide has been ascertained, methods for designing a peptide or peptidomimetic to fit that conformation are well known. See, e.g., G. R. Marshall (1993), Tetrahedron, 49: 3547-3558; Hruby and Nikiforovich (1991), in Molecular Conformation and Biological Interactions, P. Balaram & S. Ramasehan, eds., Indian Acad. of Sci., Bangalore, P P. 429-455), Eguchi M, Kahn M., Mini Rev Med Chem., 2(5):447-62, 2002. Of particular relevance to the present invention, the design of peptide analogs may be further refined by considering the contribution of various side chains of amino acid residues, e.g., for the effect of functional groups or for steric considerations as described in the art for compstatin and analogs thereof, among others.

It will be appreciated by those of skill in the art that a peptide mimic may serve equally well as a peptide for the purpose of providing the specific backbone conformation and side chain functionalities required for binding to C3 and inhibiting complement activation. Accordingly, it is contemplated as being within the scope of the present invention to produce and utilize C3-binding, complement-inhibiting compounds through the use of either naturally-occurring amino acids, amino acid derivatives, analogs or non-amino acid molecules capable of being joined to form the appropriate backbone conformation. A non-peptide analog, or an analog comprising peptide and non-peptide components, is sometimes referred to herein as a "peptidomimetic" or "isosteric mimetic," to designate substitutions or derivations of a peptide that possesses much the same backbone conformational features and/or other functionalities, so as to be sufficiently similar to the exemplified peptides to inhibit complement activation. More generally, a compstatin mimetic is any compound that would position pharmacophores similarly to their positioning in compstatin, even if the backbone differs.

The use of peptidomimetics for the development of high-affinity peptide analogs is well known in the art. Assuming rotational constraints similar to those of amino acid residues within a peptide, analogs comprising non-amino acid moieties may be analyzed, and their conformational motifs verified, by means of the Ramachandran plot (Hruby & Nikiforovich 1991), among other known techniques. Virtual screening methods can be used to identify compstatin mimetics that bind to C3. Such methods may comprise use of suitable algorithms to computationally dock, score, and optionally rank a plurality of candidate structures. Any of a wide variety of available software programs can be used to perform the virtual screening method. Exemplary programs useful for flexible molecular docking include DOCK 4.0, FlexX 1.8, AutoDock 3.0, GOLD 1.2, ICM 2.8, and more recent versions thereof.

One of skill in the art will readily be able to establish suitable screening assays to identify additional compstatin mimetics and to select those having desired inhibitory activities. For example, compstatin or an analog thereof could be labeled (e.g., with a radioactive or fluorescent label) and contacted with C3 in the presence of different concentrations of a test compound. The ability of the test compound to diminish binding of the compstatin analog to C3 is evaluated. A test compound that significantly diminishes binding of the compstatin analog to C3 is a candidate compstatin mimetic. For example, a test compound that diminishes steady-state concentration of a compstatin analog-C3 complex, or that diminishes the rate of formation of a compstatin analog-C3 complex by at least 25%, or by at least 50%, is a candidate compstatin mimetic. One of skill in the art will recognize that a number of variations of this screening assay may be employed. Compounds to be screened include natural products, libraries of aptamers, phage display libraries, compound libraries synthesized using combinatorial chemistry, etc. The invention encompasses synthesizing a combinatorial library of compounds based upon the core sequence described above and screening the library to identify compstatin mimetics. Any of these methods could also be used to identify new compstatin analogs having higher inhibitory activity than compstatin analogs tested thus far.

Other compounds, e.g., polypeptides, small molecules, monoclonal antibodies, aptamers, etc., that bind to C3 or C3a receptors (C3aR) are of use in certain embodiments of the invention. For example, U.S. Pat. No. 5,942,405 discloses C3aR antagonists. Aptamers that bind to and inhibit factor B may be identified using methods such as SELEX (discussed below). U.S. Pat. Pub. No. 20030191084 discloses aptamers that bind to C1q, C3 and C5. Also of use are RNAi agents that inhibit local expression of C3 or C3R.

Compounds that Inhibit Factor B Activation or Activity

In certain embodiments the complement inhibitor inhibits activation of factor B. For example, the complement inhibitor may bind to factor B. Exemplary agents include antibodies, antibody fragments, peptides, small molecules, and aptamers. While factor B has been suggested as a desirable target for complement inhibition where inhibition of the alternative pathway is desired, it is believed that the present disclosure is the first to specifically focus attention on the therapeutic potential of locally administered agents that inhibit factor B for treatment of inflammatory joint conditions such as arthritis. Exemplary antibodies that inhibit factor B are described in U.S. Pat. Pub. No. 20050260198. In certain embodiments the isolated antibody or antigen-binding fragment selectively binds to factor B within the third short consensus repeat (SCR) domain. In certain embodiments the antibody prevents formation of a C3bBb complex. In certain embodiments the antibody or antigen-binding fragment prevents or inhibits cleavage of factor B by factor D. In certain embodiments the complement inhibitor is an antibody, small molecule, aptamer, or polypeptide that binds to substantially the same binding site on factor B as an antibody described in U.S. Pat. Pub. No. 20050260198. Use of peptides that bind to and inhibit factor B, which may be identified using methods such as phage display, is within the scope of the invention. Use of aptamers that bind to and inhibit factor B, which may be identified using methods such as SELEX, is within the scope of the invention. Also of use are RNAi agents that inhibit local expression of factor B.

Compounds that Inhibit Factor D Activity

In certain embodiments the complement inhibitor inhibits factor D. For example, the complement inhibitor may bind to factor D. Exemplary agents include antibodies, antibody fragments, peptides, small molecules, and aptamers. While factor D has been suggested as a desirable target for systemic complement inhibition as a result of its relatively low serum concentration and ability to inhibit alternative pathway activation, it is believed that the present disclosure is the first to specifically focus attention on the therapeutic potential of locally administered agents that inhibit factor D. Exemplary antibodies that inhibit factor D are described in U.S. Pat. No. 7,112,327. In certain embodiments the complement inhibitor is an antibody, small molecule, aptamer, or polypeptide that binds to substantially the same binding site on factor D as an antibody described in U.S. Pat. No. 7,112,327. Exemplary polypeptides that inhibit alternative pathway activation and are believed to inhibit factor D are disclosed in U.S. Pub. No. 20040038869. Use of peptides that bind to and inhibit factor D, which may be identified using methods such as phage display, is within the scope of the invention. Use of aptamers that bind to and inhibit factor D, which may be identified using methods such as SELEX, is within the scope of the invention. Also of use are RNAi agents that inhibit local expression of factor D.

Compounds that Inhibit C5 Activation or Activity

In certain embodiments the complement inhibitor inhibits activation of C5. For example, the complement inhibitor may bind to C5. Exemplary agents include antibodies, antibody fragments, polypeptides, small molecules, and aptamers. Exemplary antibodies are described in U.S. Pat. No. 6,534,058. Exemplary compounds that bind to and inhibit C5 are described in U.S. Pat. Pub. Nos. 20050090448 and 20060115476. In certain embodiments the complement inhibitor is an antibody, small molecule, aptamer, or polypeptide that binds to substantially the same binding site on C5 as an antibody described in U.S. Pat. No. 6,534,058 or a peptide described in U.S. Ser. No. 10/937,912. U.S. Pat. Pub. No. 20060105980 discloses aptamers that bind to and inhibit C5. Also of use are RNAi agents that inhibit local expression of C5 or C5R.

In other embodiments the agent is an antagonist of a C5a receptor (C5aR). Exemplary C5a receptor antagonists include a variety of small cyclic peptides such as those described in U.S. Pat. No. 6,821,950; U.S. Ser. No. 11/375,587; and/or PCT/US06/08960 (WO2006/099330). In certain embodiments of the invention the complement inhibitor does not bind to C5, C5a, or C5aR. In certain embodiments of the invention the complement inhibitor does not inhibit activation of C5. In certain embodiments of the invention a cyclic peptide comprising the sequence [OPdChaWR] (SEQ ID NO: 35) is used. In certain embodiments of the invention a cyclic peptide comprising the sequence [KPdChaWR] (SEQ ID NO: 36) is used. In certain embodiments a peptide comprising the sequence (Xaa)$_n$[OPdChaWR] (SEQ ID NO: 37) is used, wherein Xaa is an amino acid residue and n is between 1 and 5. In certain embodiments a peptide comprising the sequence (Xaa)$_n$[KPdChaWR] (SEQ ID NO: 38) is used, wherein Xaa is an amino acid residue and n is between 1 and 5. In certain embodiments of the invention n is 1. In certain embodiments of the invention n is 1 and Xaa is a standard or nonstandard aromatic amino acid. For example, the peptides F-[OPdChaWR] (SEQ ID NO: 39), F-[KPdChaWR] (SEQ ID NO: 40); Cin-[OPdChaWR] (SEQ ID NO: 41), and HCin-[OPdChaWR] (SEQ ID NO: 42) are of interest. Optionally the free terminus comprises a blocking moiety, e.g., the terminal amino acid is acetylated. (Abbreviations: O: ornithine; Cha: cyclohexylalanine; Cin: cinnamoyl; Hcin: hydrocinnamoyl; square brackets denote internal peptide bond).

Multimodal Complement Inhibitors

In certain embodiments of the invention the complement inhibitor binds to more than one complement protein and/or inhibits more than one step in a complement activation pathway. Such complement inhibitors are referred to herein as "multimodal". One aspect of this invention is the recognition of the advantages of inhibiting local complement activation by local administration of a multimodal complement inhibitor for treatment of various disorders discussed herein. In certain embodiments of the invention the complement inhibitor is a virus complement control protein (VCCP). The invention specifically contemplates use of any of the agents described in U.S. Ser. No. 11/247,886 and PCT/US2005/36547, filed Oct. 8, 2005. Poxviruses and herpesviruses are families of large, complex viruses with a linear double-stranded DNA genome. Certain of these viruses encode immunomodulatory proteins that are believed to play a role in pathogenesis by subverting one or more aspects of the normal immune response and/or fostering development of a more favorable environment in the host organism (Kotwal, G J, *Immunology Today*, 21(5), 242-248, 2000). Among these are VCCPs. Poxvirus complement control proteins are members of the complement control protein (CCP) superfamily and typically contain 4 SCR modules. These proteins have features that make them advantageous for local complement inhibition in accordance with the present invention. In certain embodiments the VCCP is a poxvirus complement control protein (PVCCP). The PVCCP can comprise a sequence encoded by, e.g., vaccinia virus, variola major virus, variola minor virus, cowpox virus, monkeypox virus, ectromelia virus, rabbitpox virus, myxoma virus, Yaba-like disease virus, or swinepox virus. In other embodiments the VCCP is a herpesvirus complement control protein (HVCCP). The HVCCP can comprise a sequence encoded by a *Macaca fuscata* rhadinovirus, cercopithecine herpesvirus 17, or human herpes virus 8. In other embodiments the HVCCP comprises a sequence encoded by herpes simplex virus saimiri ORF 4 or ORF 15 (Albrecht, J C. & Fleckenstein, B., J. Virol., 66, 3937-3940, 1992; Albrecht, J., et al., Virology, 190, 527-530, 1992).

The VCCP may inhibit the classical complement pathway, the alternate complement pathway, the lectin pathway, or any two or more of these. In certain embodiments of the invention the VCCP, e.g., a PVCCP, binds to C3b, C4b, or both. In certain embodiments of the invention the PVCCP comprises one or more putative heparin binding sites (K/R-X-K/R) and/or possesses an overall positive charge. In some embodiments the PVCCP comprises at least 3 SCR modules (e.g., modules 1-3), e.g., 4 SCR modules. The PVCCP protein can be a precursor of a mature PVCCP (i.e., can include a signal sequence that is normally cleaved off when the protein is expressed in virus-infected cells) or can be a mature form (i.e., lacking the signal sequence).

Vaccinia complement control protein (VCP) is a virus-encoded protein secreted from vaccinia infected cells. VCP is 244 amino acids in length, contains 4 SCRs, and is naturally produced by intracellular cleavage of a 263 amino acid precursor. VCP runs as an ~35 kD protein in a 12% SDS/polyacrylamide gel under reducing conditions and has a predicted molecular mass of about 28.6 kD. VCP is described in U.S. Pat. Nos. 5,157,110 and 6,140,472, and in Kotwal, G K, et al., *Nature*, 355, 176-178, 1988. FIGS. 3A and 3B of U.S. Ser. No. 11/247,886 and PCT/US2005/36547 (WO2006042252) show the sequence of the precursor and mature VCP proteins, respectively. VCP has been shown to inhibit the classical pathway of complement activation via its ability to bind to C3 and C4 and act as a cofactor for factor I mediated cleavage of these components as well as promoting decay of existing convertase (Kotwal, G K, et al., *Science*, 250, 827-830, 1990; McKenzie et al., *J. Infect. Dis.*, 1566, 1245-1250, 1992). It has also been shown to inhibit the alternative pathway by causing cleavage of C3b into iC3b and thereby preventing the formation of the alternative pathway C3 convertase (Sahu, A, et al., *J. Immunol.*, 160, 5596-5604, 1998). VCP thus blocks complement activation at multiple steps and reduces levels of the proinflammatory chemotactic factors C3a, C4a, and C5a.

VCP also possesses the ability to strongly bind heparin in addition to heparan sulfate proteoglycans. VCP contains two putative heparin binding sites located in modules 1 and 4 (Jha, P and Kotwal, G J, and references therein). VCP is able to bind to the surface of endothelial cells, possibly via interaction with heparin and/or heparan sulfate at the cell surface, resulting in decreased antibody binding (Smith, S A, et al., *J. Virol.*, 74(12), 5659-5666, 2000). VCP can be taken up by mast cells and possibly persist in tissue for lengthy periods of time, thereby potentially prolonging its activity (Kotwal, G J, et al., In GP. Talwat, et al. (eds), 10$^{th}$ International Congress of Immunology., Monduzzi Editore, Bologna, Italy, 1998). In addition, VCP can reduce chemotactic migration of leukocytes by blocking chemokine binding (Reynolds, D, et al., in S. Jameel and L. Villareal (ed., *Advances in animal virology*. Oxford and IBN Publishing, New Delhi, India, 1999). VCP and other PVCCPs have a relatively small size relative to mammalian CCPs, which is advantageous for delivery in the present invention.

Variola virus major and minor encode proteins that are highly homologous to VCP and are referred to as smallpox inhibitor of complement enzymes (SPICE) (Rosengard, A M, et al., *Proc. Natl. Acad. Sci.*, 99(13), 8803-8813. U.S. Pat. No. 6,551,595). SPICE from various variola strains sequenced to date differs from VCP by about 5% (e.g., about 11 amino acid differences). Similarly to VCP, SPICE binds to C3b and C4b and causes their degradation, acting as a cofactor for factor I. However, SPICE degrades C3b approximately 100 times as fast as VCP and degrades C4b approximately 6 times as fast as VCP. The amino acid sequence of SPICE is presented in FIG. 6 (SEQ ID NO: 12) of U.S. Ser. No. 11/247,886 and PCT/US2005/36547 (WO2006042252) and can be described as follows. Referring to FIG. 6 of U.S. Ser. No. 11/247,886 and PCT/US2005/36547 (WO2006042252), a signal sequence extends from amino acid 1 to about amino acid 19. Four SCRs extend from about amino acid 20 to amino acid 263. Each SCR is characterized by four cysteine residues. The four cysteine residues form two disulfide bonds in the expressed protein. The boundaries of each SCR are best defined by the first and fourth cysteine residues in the sequence that forms the disulfide bonds of the SCR. An invariant tryptophan residue is present between cysteine 3 and cysteine 4 of each SCR. SCR1 extends from amino acid 20 or 21 to amino acid 81. Both residues are cysteines that may be involved in disulfide bonding. SCR2 extends from amino acid 86 to amino acid 143. SCR3 extends from amino acid 148 to amino acid 201. SCR4 extends from amino acid 206 to amino acid 261. The SCRs include the complement binding locations of SPICE. SPICE or any of the portions thereof that inhibit complement activation, e.g., SPICE and SPICE-related polypeptides containing four SCRs, such as those described in U.S. Pat. No. 6,551,595, are of use in the present invention.

Complement control proteins from cowpox virus (referred to as inflammation modulatory protein, IMP) and monkeypox virus (referred to herein as monkeypox virus complement control protein, MCP) have also been identified and sequenced (Miller, C G, et al., *Virology,* 229, 126-133, 1997 and Uvarova, E A and Shchelkunov, S N, *Virus Res.,* 81(1-2), 39-45, 2001). MCP differs from the other PVCCPs described herein in that it contains a truncation of the C-terminal portion of the fourth SCR.

It will be appreciated that the exact sequence of complement control proteins identified in different virus isolates may differ slightly. Such proteins fall within the scope of the present invention. Complement control proteins from any such isolate may be used, provided that the protein has not undergone a mutation that substantially abolishes its activity. Thus the sequence of a VCCP such as SPICE or VCP may differ from the exact sequences presented herein or under the accession numbers listed in Table 2. It will also be appreciated that a number of amino acid alterations, e.g., additions, deletions, or substitutions such as conservative amino acid substitutions, may be made in a typical polypeptide such as a VCCP without significantly affecting its activity, such that the resulting protein is considered equivalent to the original polypeptide. The viral polypeptides identified by accession number in Table 2 below are of use in various embodiments of the invention.

TABLE 2

Representative Viral Complement Control Proteins

| Virus | Protein | Accession | Virus Type |
|---|---|---|---|
| Variola | D12L | NP_042056 | Orthopoxvirus |
| | D15L (SPICE) | AAA69423 | Orthopoxvirus |
| Vaccinia | VCP | AAO89304 | Orthopoxvirus |
| Cowpox | CPXV034 | AAM13481 | Orthopoxvirus |
| | C17L | CAA64102 | Orthopoxvirus |
| Monkeypox | D14L | AAV84857 | Orthopoxvirus |
| Ectromelia virus | Complement control protein | CAE00484 | Orthopoxvirus |
| Rabbitpox | RPXV017 | AAS49730 | Orthopoxvirus |
| Macaca fuscata rhadinovirus | JM4 | AAS99981 | Rhadinavirus (Herpesvirus) |
| Cercopithecine herpesvirus 17 | Complement binding protein (ORF4) | NP_570746 | Herpesvirus |
| Human herpes virus 8 | Complement binding protein (ORF4) | AAB62602 | Herpesvirus |

In addition to the VCCPs described above, a number of other viral proteins exist that interfere with one or more steps in a complement pathway. These proteins are also of use in certain embodiments of the present invention. Certain of these proteins do not necessarily display clear homology to cellular complement regulators known to date. For example, HSV-1, HSV-2, VZV, PRV, BHV-1, EHV-1, and EHV-4 all encode versions of a conserved glycoprotein known as gC (Schreurs, et al., *J Virol.,* 62, 2251-2257, 1988; Mettenleiter, et al, *J. Virol.,* 64, 278-286; 1990; Herold, et al., *J Virol.,* 65, 1090-1098; 1991). With the exception of VZV, the gC protein encoded by these viruses binds to C3b (Friedman, et al., *Nature,* 309, 633-634, 1984; Huemer, et al., *Virus Res.,* 23, 271-280, 1993) gC1 (from HSV-1) accelerates decay of the classical pathway C3 convertase and inhibits binding of properdin and C5 to C3. Purified EBV virions possess an activity that accelerates decay of the alternative pathway C3 convertase and serves as a cofactor for the complement regulatory protein factor 1 (Mold et al., *J Exp Med,* 168, 949-969, 1988). The foregoing proteins are referred to collectively as virus complement interfering proteins (VCIPs). By any of a variety of means, such as interfering with one or more steps of complement activation, accelerating decay of a complement component, and/or enhancing activity of a complement regulatory protein, these VCIPs are said to inhibit complement. Any of these proteins, or derivatives thereof, e.g., fragments or variants thereof, can be used as a therapeutic agent in the invention. As in the case of VCCPs, will be appreciated that the exact sequence of VCIPs identified in different virus isolates may differ slightly. Such proteins fall within the scope of the present invention.

In certain embodiments of the invention a fragment or variant of a VCCP or VCIP is locally administered to an extravascular location of a subject. Preferred fragments and variants of a PVCCP possess at least one of the following activities: (i) ability to bind to C3, C3b, or both; (ii) ability to act as a cofactor for factor I cleavage of C3; (iii) ability to bind to C4, C4b, or both; (iv) ability to act as a cofactor for factor I cleavage of C4; (v) ability to accelerate decay of existing C3 convertase of the classical pathway, alternate pathway, or both; (vi) ability to bind heparin; (vii) ability to bind to heparan sulfate proteoglycans; (viii) ability to reduce chemotactic migration of leukocytes; (ix) ability to block chemokine (e.g., MIP-1$\alpha$) binding, e.g., to the surface of a cell (e.g., a leukocyte or endothelial cell surface); (x) ability to inhibit antibody binding to class I MHC molecules; (xi) ability to inhibit the classical complement pathway; (xii) ability to inhibit the alternative complement pathway; and (xiii) ability to inhibit complement-mediated cell lysis. Preferred PVCCP fragments and variants display complement binding activity, by which is meant ability to detectably bind to one or more complement components, preferably selected from the group consisting of: C3, C3b, C4, and C4b. Preferred fragments or variants of HVCCPs may also display ability to detectably bind to one or more complement components. Preferably the binding of the VCCP to the complement component is specific. It will be understood that a VCCP may be able to bind to only a single complement component or may be able to bind to more than one different complement component.

In certain embodiments of the invention the PVCCP fragment or variant comprises at least 3 SCR modules (e.g., modules 1-3), preferably 4 SCR modules. Preferably each of the SCR modules displays significant sequence identity to an SCR module found in a naturally occurring PVCCP, e.g., VCP or SPICE. Preferably the multiple SCR modules are arranged in an N to C manner so as to maximize overall identity to a naturally occurring PVCCP. If the sequence of a PVCCP fragment or variant contains an SCR domain that differs from the SCR consensus sequence at one or more positions, in certain embodiments of the invention the amino acid(s) at the one or more differing positions is identical to that found at a corresponding position in the most closely related SCR found in a naturally occurring PVCCP. In certain embodiments the PVCCP variant comprises at least one SCR module from a first PVCPP and at least one SCR module from a second PVCPP. In certain embodiments the PVCCP variant comprises at least one SCR module from a PVCCP and at least one SCR from a mammalian complement control protein (RCA protein). Any number of SCR modules, e.g., 1, 2, 3, 4, or more can come from any particular PVCCP or RCA protein in various embodiments of the invention. All such combinations and permutations are contemplated, even if not explicitly set forth herein.

Generally a fragment or variant of a naturally occurring VCCP or VCIP possesses sufficient structural similarity to its naturally occurring counterpart that it is recognized by a polyclonal antibody that recognizes the naturally occurring counterpart. In certain embodiments of the invention a fragment or variant of a VCCP possesses sufficient structural similarity to VCP or SPICE so that when its 3-dimensional structure (either actual or predicted structure) is superimposed on the structure of VCP or SPICE, the volume of overlap is at least 70%, preferably at least 80%, more preferably at least 90% of the total volume of the VCP structure. A partial or complete 3-dimensional structure of the fragment or variant may be determined by crystallizing the protein as described for VCP (Murthy, 2001). Alternately, an NMR solution structure can be generated, as performed for various VCP fragments (Wiles, A P, et al., *J. Mol. Biol.* 272, 253-265, 1997). A modeling program such as MODELER (Sali, A. and Blundell, T L, *J. Mol. Biol.*, 234, 779-815, 1993), or any other modeling program, can be used to generate a predicted structure. The model can be based on the VCP structure and/or any known SCR structure. The PROSPECT-PSPP suite of programs can be used (Guo, J T, et al., *Nucleic Acids Res.* 32(Web Server issue):W522-5, Jul. 1, 2004). Similar methods may be used to generate a structure for SPICE.

Fragments or variants of a VCCP or VCIP may be generated by any available means, a large number of which are known in the art. For example, VCCPs, VCIPs, and fragments or variants thereof can be produced using recombinant DNA technology as described below. A VCCP or VCIP fragment may be chemically synthesized, produced using PCR amplification from a cloned VCCP or VCIP sequence, generated by a restriction digest, etc. Sequences for a VCCP variant may be generated by random mutagenesis of a VCCP sequence (e.g., using X-rays, chemical agents, or PCR-based mutagenesis), site-directed mutagenesis (e.g., using PCR or oligonucleotide-directed mutagenesis, etc. Selected amino acids can be changed or added.

While not wishing to be bound by any theory, it is likely that amino acid differences between naturally occurring PVCCPs occur at positions that are relevant in conferring differences in particular properties such as ability to bind heparin, activity level, etc. For example, VCP and SPICE differ at only 11 amino acids, but SPICE has a much higher activity as a cofactor for cleavage of C3b (e.g., cleavage occurs at a much faster rate with SPICE than with VCP). The amino acid differences are likely to be responsible for the differential activities of the two proteins. The amino acids at these positions are attractive candidates for alteration to identify variants that have yet greater activity.

Additional Complement Inhibiting Agents, Mixtures, and Modifications

A variety of other complement inhibitors can be used in various embodiments of the invention. In some embodiments of the invention the complement inhibitor is a naturally occurring mammalian complement regulatory protein or a fragment or derivative thereof. For example, the complement regulatory protein may be CR1, DAF, MCP, CFH, or CFI. In some embodiments of the invention the complement regulatory polypeptide is one that is normally membrane-bound in its naturally occurring state. In some embodiments of the invention a fragment of such polypeptide that lacks some or all of a transmembrane and/or intracellular domain is used. Soluble forms of complement receptor 1 (sCR1), for example, are of use in the invention. For example the compounds known as TP10 or TP20 (Avant Therapeutics) can be used. C1 inhibitor (C1-INH) is also of use. In some embodiments a soluble complement control protein, e.g., CFH, is used. In some embodiments of the invention the polypeptide is modified to increase its solubility.

Inhibitors of C1s are of use. For example, U.S. Pat. No. 6,515,002 describes compounds (furanyl and thienyl amidines, heterocyclic amidines, and guanidines) that inhibit C1s. U.S. Pat. Nos. 6,515,002 and 7,138,530 describe heterocyclic amidines that inhibit C1s. U.S. Pat. No. 7,049,282 describes peptides that inhibit classical pathway activation. Certain of the peptides comprise or consist of WESNGQPENN (SEQ ID NO: 33) or KTISKAKGQPREPQVYT (SEQ ID NO: 34) or a peptide having significant sequence identity and/or three-dimensional structural similarity thereto. In some embodiments these peptides are identical or substantially identical to a portion of an IgG or IgM molecule. U.S. Pat. No. 7,041,796 discloses C3b/C4b Complement Receptor-like molecules and uses thereof to inhibit complement activation. U.S. Pat. No. 6,998,468 discloses anti-C2/C2a inhibitors of complement activation. U.S. Pat. No. 6,676,943 discloses human complement C3-degrading protein from *Streptococcus pneumoniae*.

Combination therapy using two or more complement inhibitors is within the scope of the invention. The two or more complement inhibitors may be provided in the same composition. In one embodiment at least two of the complement inhibitors are peptides, each having a length between 5 and 50 amino acids. In certain embodiments the complement inhibitors bind to two or more different complement components. In certain embodiments the complement inhibitors bind to two or more different soluble complement proteins. In certain embodiments the complement inhibitors inhibit activation or activity of at least two complement proteins selected from C3, C5, factor B, and factor D. In certain embodiments a first complement inhibitor inhibits activation or activity of C3 and a second complement inhibitor inhibit activation or activity of a complement protein selected from C5, factor B, and factor D. In certain embodiments a first complement inhibitor inhibits activation or activity of C3 and a second complement inhibitor inhibit activation or activity of a complement protein selected from factor B and factor D. In certain embodiments a first complement inhibitor inhibits activation or activity of C3 and a second complement inhibitor inhibit activation or activity of a complement protein selected from C5 and C5a.

Complement inhibitors, optionally linked to a binding moiety, can be modified by addition of a molecule such as polyethylene glycol (PEG) or similar molecules to stabilize the compound, reduce its immunogenicity, increase its lifetime in the body, increase or decrease its solubility, and/or increase its resistance to degradation. Methods for pegylation are well known in the art (Veronese, F. M. & Harris, *Adv. Drug Deliv. Rev.* 54, 453-456, 2002; Davis, F. F., Adv. Drug Deliv. Rev. 54, 457-458, 2002; Wang, Y. S. et al. *Adv. Drug Deliv. Rev.* 54, 547-570, 2002). A wide variety of polymers such as PEGs and modified PEGs, including derivatized PEGs to which polypeptides can conveniently be attached are described in Nektar Advanced Pegylation 2005-2006 Product Catalog, Nektar Therapeutics, San Carlos, Calif., which also provides details of appropriate conjugation procedures.

In certain embodiments the complement inhibitor is a multivalent compound comprising a plurality of complement inhibitor moieties covalently or noncovalently linked to a polymeric backbone or scaffold. The complement inhibitor moieties may be the same or different. A complement inhibitor may comprise or be modified to comprise a reactive functional group or be attached to a linker comprising a reactive functional group. The reactive functional group facilitates the attachment of the complement inhibitor to the polymeric backbone. The complement inhibitor can be any of the complement inhibitors described herein. It will be appreciated that following attachment to the polymeric backbone, the structure of the complement inhibitor moiety will differ slightly from that of the complement inhibitors described herein. For example, a complement inhibitor comprising an amine ($NH_2$) group, represented as $NH_2$—$R^1$, may react with a moiety comprising a carboxylic acid (COOH), represented as $R^2$—(C=O)OH to form a conjugate having formula $R^2$—(C=O)—NH—$R^1$, in which one of the hydrogens present in the complement inhibitor is no longer present and a new covalent bond (C—N) has been formed. Thus the term "complement inhibitor moiety" includes molecules having the precise formula of a complement inhibitor as described herein as well as molecular structures in which a functional group of a complement inhibitor has reacted with a second functional group, which typically entails loss of at least one atom or group of atoms that was present in the complement inhibitor molecule prior to the reaction and formation of a new covalent bond. The new covalent bond is formed between an atom that was previously attached to one of the atoms that is lost from the complement inhibitor and an atom to which the complement inhibitor becomes attached.

The complement inhibitor moieties can be identical or different. In certain embodiments of the invention the multivalent compound comprises multiple instances, or copies, of a single complement inhibitor moiety. In other embodiments of the invention the multivalent compound comprises one or more instances of each of two of more non-identical complement inhibitor moieties, e.g., 3, 4, 5, or more different complement inhibitor moieties. In certain embodiments of the invention the number of complement inhibitor moieties ("n") is between 2 and 6. In other embodiments of the invention n is between 7 and 20. In other embodiments of the invention n is between 20 and 100. In other embodiments n is between 100 and 1,000. In other embodiments of the invention n is between 1,000 and 10,000. In other embodiments n is between 10,000 and 50,000. In other embodiments n is between 50,000 and 100,000. In other embodiments n is between 100,000 and 1,000,000.

The complement inhibitor moieties may be attached directly to the polymeric scaffold or may be attached via a linking moiety that connects the complement inhibitor moiety to the polymeric scaffold. The linking moiety may be attached to a single complement inhibitor moiety and to the polymeric scaffold. Alternately, a linking moiety may have multiple complement inhibitor moieties joined thereto so that the linking moiety attaches multiple compstatin analog moieties to the polymeric scaffold.

In one embodiment, the complement inhibitor comprises an amino acid having a side chain comprising a primary or secondary amine, e.g., a Lys residue. For example, a Lys residue, or a sequence comprising a Lys residue, is added at the C-terminus of the complement inhibitor. In one embodiment, the Lys residue is separated from the cyclic portion of the complement inhibitor by a rigid or flexible spacer. The spacer may, for example, be a substituted or unsubstituted, saturated or unsaturated alkyl chain. The length of the alkyl chain may be, e.g., between 2 and 20 carbon atoms. In other embodiments the spacer is a peptide. The peptide spacer may be, e.g., between 1 and 20 amino acids in length, e.g., between 4 and 20 amino acids in length. Suitable spacers comprise or consist of multiple Gly residues, Ser residues, or both.

Any of a variety of polymeric backbones or scaffolds could be used. For example, the polymeric backbone or scaffold may be a polyamide, polysaccharide, polyanhydride, polyacrylamide, polymethacrylated, polypeptide, polyethylene oxide, or dendrimer. Suitable methods and polymeric backbones are described, e.g., in WO98/46270 (PCT/US98/07171) or WO98/47002 (PCT/US98/06963). In one embodiment, the polymeric backbone or scaffold comprises multiple reactive functional groups, such as carboxylic acids, anhydride, or succinimide groups. The polymeric backbone or scaffold is reacted with the complement inhibitors. In one embodiment, the complement inhibitor comprises any of a number of different reactive functional groups, such as carboxylic acids, anhydride, or succinimide groups, which are reacted with appropriate groups on the polymeric backbone. Alternately, monomeric units that could be joined to one another to form a polymeric backbone or scaffold are first reacted with the complement inhibitors and the resulting monomers are polymerized. In another embodiment, short chains are prepolymerized, functionalized, and then a mixture of short chains of different composition are assembled into longer polymers.

Targeted Complement Inhibitors

In certain embodiments of the invention the complement inhibitor is targeted to a component present at an extravascular location of a subject at risk of or suffering from a complement-mediated disorder. According to these embodiments a composition comprising (i) a complement inhibitor; and (ii) a binding moiety that binds to a component present at an extravascular location of a subject at risk of or suffering from a complement-mediated disorder, wherein said extravascular location is not the eye, and said disorder is not an eye disorder is locally administered to the subject. In certain embodiments the binding moiety and the complement inhibitor are linked. The linkage can be covalent or noncovalent and can be direct or indirect in various embodiments of the invention. The binding moiety can be, for example, an antibody or ligand, as discussed below. In general, the component can be any molecule present on or at the surface of a cell or noncellular molecular entity. By "on or at the surface of the cell or noncellular molecular entity" is meant that the component is accessible to molecules present in the extracellular environment so that it can be recognized and bound by the moiety. According to certain embodiments of the invention the component is a cellular marker. The cellular marker can be any marker that is expressed on or at the surface of a cell present at an extracellular location of interest. In certain embodiments of the invention the cellular marker is a cell type specific marker.

The component may be entirely extracellular. The component may be inserted into the cell membrane. In certain embodiments of the invention the component may be partly or entirely within the membrane, in which case the entity must partially penetrate the membrane to gain access. In general, the component is not located in the cytoplasm of a cell. As long as a sufficient portion of the component is exposed or accessible so that it can be recognized and bound, it will be said to be present on or at the surface. If the target is a molecular entity other than a cell, the component can be any chemical entity present on or at the surface of the molecule that is recognizable by an antibody or ligand. A large number of molecular components have been identified in deposits at sites of inflammation. Such components are suitable noncellular molecular entities to which complement inhibitor can be targeted. Typically the binding moiety will recognize a subportion of the component having particular three-dimensional structural features. Such portion will be referred to as an "epitope" though it is understood that the binding moiety may not be an antibody. The epitope may be one that is exposed or present only or largely in the diseased state.

In certain embodiments the marker is a component present in a superficial layer of articular cartilage in a patient diagnosed with arthritis, or other joint disorder. The epitope may be in a superficial layer of articular cartilage in a patient diagnosed with an arthritis, or other joint disorder. In certain embodiments the epitope is on Type II collagen or Type II collagen fragments of articular cartilage. In certain embodiments the epitope is present at a cleavage site generated by the individual or combined action of enzymes selected from the group consisting of matrix metalloproteinases and collagenases, e.g., selected from (MMP)-1, MMP-3, MMP-8 and MMP-13. In certain embodiments the epitope is on aggrecan, biglycan, or decorin of articular cartilage, or fragments of any of these. In certain embodiments the epitope is present at a cleavage site generated by the action of an enzyme that belongs to a group consisting of the A Disintegrin And Metalloproteinase with Thrombospondin motifs (ADAMTS) family and/or the MMP family. See, e.g., U.S. Pat. No. 7,067,144 and references therein for discussion of these epitopes and binding moieties therefor.

In certain embodiments of the invention the binding moiety is linked to the complement inhibitor. In other embodiments the binding moiety comprises a portion that binds to another molecule to which the complement inhibitor is attached. Suitable binding moieties include antibodies and ligands that specifically bind to a cellular marker or noncellular molecular entity such as those mentioned above. The linkage between the binding moiety and the complement inhibitor can be covalent or noncovalent and can be direct or indirect in various embodiments of the invention. "Indirect" in this context means that the binding moiety and the complement inhibitor are both linked to a third moiety. In various embodiments of the invention an appropriate binding moiety is any molecule that specifically binds to a target molecule (e.g., polypeptide or a portion thereof such as a carbohydrate moiety), through a mechanism other than an antigen-antibody interaction. Such a binding moiety is referred to as a "ligand". For example, in various embodiments of the invention the ligand is a polypeptide, peptide, nucleic acid (e.g., DNA or RNA), carbohydrate, lipid or phospholipid, or small molecule (e.g., an organic compound, whether naturally-occurring or artificially created that has relatively low molecular weight and is not a protein, polypeptide, nucleic acid, or lipid, typically with a molecular weight of less than about 1500 g/mol and typically having multiple carbon-carbon bonds).

Ligands may be naturally occurring or synthesized, including molecules whose structure has been invented by man. Examples of ligands include, but are not limited to, hormones, growth factors, or neurotransmitters that bind to particular receptors. It will also be appreciated that fragments or variants of polypeptide ligands differing in sequence from their naturally occurring counterparts but retaining the ability to bind to a cell of interest can also be used. Peptide ligands can be identified using phage display (Arap W, et al, *Nature Medicine* 8(2):121-7, 2002); Zurita A J, et al., *J Control Release,* 91(1-2):183-6, 2003; Pasqualini, R. & Ruoslahti, E. *Nature* 380, 364-366, 1996; Pasqualini, R., et al., *Trends Mol. Med.* 8, 563-571, 2002). In certain embodiments of the invention the ligand is an aptamer that binds to a cell type specific marker. In general, an aptamer is an oligonucleotide (e.g., DNA or RNA or) that binds to a particular protein. Aptamers are typically derived from an in vitro evolution process called SELEX. Methods for obtaining aptamers specific for a protein of interest are known in the art. See, e.g., Brody E N, Gold L. *J Biotechnol.,* 74(1):5-13, 2000. Small molecules can also be used as ligands. Methods for identifying such ligands are known in the art. For example in vitro screening of small molecule libraries, including combinatorial libraries, and computer-based screening, e.g., to identify small organic compounds that bind to concave surfaces (pockets) of proteins, can identify small molecule ligands for numerous proteins of interest (Huang, Z., *Pharm. & Ther.* 86: 201-215, 2000).

In certain embodiments of the invention binding moieties are not proteins or molecules that are typically used as carriers and conjugated to antigens for the purpose of raising antibodies. Examples are carrier proteins or molecules such as bovine serum albumin, keyhole limpet hemocyanin, bovine gamma globulin, and diphtheria toxin. In certain embodiments of the invention the cell binding moiety is not an Fc portion of an immunoglobulin molecule.

Methods for covalently or noncovalently linking a complement inhibitor to a binding moiety are known in the art. See, e.g., U.S. Ser. No. 10/923,940. General methods for conjugation and cross-linking are described in "Cross-Linking", Pierce Chemical Technical Library, available at the Web site having URL www.piercenet.com and originally published in the 1994-95 Pierce Catalog and references cited therein, in Wong S S, *Chemistry of Protein Conjugation and Crosslinking,* CRC Press Publishers, Boca Raton, 1991; and G. T. Hermanson, supra. See also, Allen, T. M., *Nature Reviews Cancer,* 2, 750-763, 2002. For example, according to certain embodiments of the invention a bifunctional crosslinking reagent is used to couple a complement inhibitor to an antibody or ligand. In general, bifunctional crosslinking reagents contain two reactive groups, thereby providing a means of covalently linking two target groups. The reactive groups in a chemical crosslinking reagent typically belong to various classes including succinimidyl esters, maleimides, pyridyldisulfides, and iodoacetamides. Bifunctional chelating agents may also be used.

Producing Complement Inhibitors

In general, the complement inhibitors are manufactured using standard methods known in the art and suitable for compounds of that class. Peptides such as compstatin analogs and other peptides discussed herein may be manufactured using standard solid phase peptide synthesis techniques. Polypeptides may, for example, be purified from natural sources, produced in vitro or in vivo in suitable expression systems using recombinant DNA technology in suitable expression systems (e.g., by recombinant host cells or in transgenic animals or plants), synthesized through chemical means such as conventional solid phase peptide synthesis and/or methods involving chemical ligation of synthesized peptides. Recombinant polypeptides such as recombinant VCCPs may be produced using standard recombinant nucleic acid techniques as described, e.g., in U.S. Ser. No. 11/247,886 and PCT/US2005/36547 (WO2006042252) and expression systems. See, e.g., Hardin, C., et al., (Eds.), "Cloning, Gene Expression and Protein Purification: Experimental Procedures and Process Rationale", Oxford University Press, Oxford, 2001, for further information regarding production of recombinant polypeptides and purification of polypeptides. Activity of certain polypeptides is at least partly dependent on their glycosylation state. It may be desirable to produce such polypeptides in systems that provide for glycosylation similar or substantially identical to that found in mammals, e.g., humans. For example, mammalian expression systems or modified lower eukaryotic expression systems (e.g., fungal expression systems), that provide for mammalian-like glycosylation can be used. See, e.g., U.S. Pub. Nos. 20060177898 and 20070184063. Antibodies, e.g., monoclonal antibodies, may be harvested from hybridomas or produced using recombinant methods as known in the art. Chemical modifications such as pegylation may be performed using standard methods.

In certain embodiments of the invention rather than administering a complement inhibiting polypeptide, recombinant cells that produce and secrete the polypeptide (e.g., a compstatin analog) are administered. Such cells may be generated similarly to recombinant host cells useful for protein expression (i.e., by introduction of a nucleic acid such as an expression vector that encodes the polypeptide into the cell). Typically a stable cell line is generated. The cells may be, for example, stem cells or precursor or mature cells of a type found at the extravascular location, e.g., fibroblasts, keratinocytes. In other embodiments of the invention any other cell type may be used. Autologous cells may be used. The cells can be introduced into any extravascular location contemplated herein. They may be encapsulated in a suitable material or structure that provides sufficient contact with bodily fluids for survival of the cells and release of the complement inhibitor to its desired site of activity.

Compositions, Sustained Release Formulations, and Routes of Administration

The invention provides compositions suitable for administration to an extravascular location such as a joint, the skin, the spinal canal, the brain, respiratory tract, the vitreous humour, the subretinal space, etc. In certain embodiments the compositions are sustained release formulations. Certain compositions of the invention comprise a complement inhibitor and a biocompatible polymer. In some embodiments the biocompatible polymer is biodegradable. The composition may be in the form of a solid or semi-solid article. In some embodiments the composition is in the form of a gel or a liquid that forms a gel upon exposure to physiological environment. Compositions may be formulated for local delivery in capsules, particles, microcapsules, microparticles, nanocapsules, nanoparticles, osmotic pumps, diffusion devices, liposomes, liposphseres, niosomes, etc. Such delivery systems comprising a complement inhibitor are an aspect of this invention.

In certain embodiments of the present invention the sustained release formulation of the invention comprises a complement inhibitor and an additional component, element, or structure that contributes to the sustained release properties of the formulation. The additional component, element, or structure that is effective to provide sustained release is referred to herein as a "drug delivery regulating component" or "sustained release material". Optionally the drug delivery regulating element is designed to provide control over the kinetics of release. It will be appreciated that the physical nature of the formulation, e.g., the shape, total surface area, ration of surface area to volume, etc., of any solid or semi-solid constituents, may contribute to its sustained release properties. As another example, tight compression of particles containing a therapeutic agent may result in release that takes place over a longer time period than if the particles are not compressed.

In certain embodiments of the invention the complement inhibitor is selected to have desirable properties for preparation of a sustained release formulation. In some embodiments the complement inhibitor is selected to be soluble in an aqueous medium, e.g., water or phosphate buffered saline (PBS), at concentrations of up to, e.g., about 5, 10, 25, 50, 100, 150, 200, 250, 300, 350, 400, 450, or 500 within a selected pH range. In other embodiments of the invention the complement inhibitor is selected to be at least in part insoluble (e.g., to form an aggregate or precipitate) at concentrations above, e.g., about 5, 10, 25, 50, 100, 150, 200, or 250, 300, 350, 400, 450, or 500 mg/ml in an aqueous medium such as water or PBS within a selected pH range. In certain embodiments the complement inhibitor is selected to be soluble in an organic solvent such as ethanol, dimethyl sulfoxide, or dimethyl formamide at concentrations of up to, e.g., about 5, 10, 25, 50, 100, 150, 200, 250, 300, 350, 400, 450, or 500 mg/ml within a selected pH range. In other embodiments of the invention the complement inhibitor is selected to be at least in part insoluble under such conditions. The selected pH range may be between 2.0 and 11.0, or any intervening range (e.g., 3.0-10.0, 4.0-9.0, 5.0-8.0) or value.

The drug delivery regulating component may comprise or consist of a polymer matrix that is physically associated with the therapeutic agent. For example, the agent may be entrapped, embedded, or encapsulated by the polymer matrix. A sustained release formulation can be an individual implant, a plurality of particles (nanoparticles, microparticles) or liposomes, a semi-solid or viscous material, etc. In general, compositions having concentrations of between about 0.001% and about 100% active agent(s) by weight may be used. The active agent(s) may be from about 1% to 90% by weight of the sustained release formulation. Often the active agent(s) is/are from about 20% to about 80% by weight of the of the sustained release formulation. In certain embodiments, the therapeutic agent(s) comprise about 30%-50% by weight of the sustained release formulation. A sustained release formulation may release the agent by diffusion or as a result of breakdown or erosion of at least a portion of the composition. The formulation may comprise a matrix that is permeable or semi-permeable to the agent.

A number of polymeric delivery vehicles for providing sustained release are known in the art and can be used to administer a complement inhibitor. Various polymers, e.g., biocompatible polymers, which may be biodegradable, can be used. The polymers may be homopolymers, copolymers (including block copolymers), straight, branched-chain, or cross-linked. Natural or synthetic polymers can be used in various embodiments of the invention. Useful polymers include, but are not limited to, poly-lactic acid (PLA), polyglycolic acid (PGA), poly-lactide-co-glycolide (PLGA), poly(phosphazine), poly(phosphate ester), polycaprolactones, polyanhydrides, ethylene vinyl acetate, polyorthoesters, polyethers, and poly(beta amino esters). In certain embodiments the formulation comprises poly-lactic-co-glycolic acid (PLGA) and can be prepared as described in Lewis, "Controlled Release of Bioactive Agents from Lactide/Glycolide polymer," in Biodegradable Polymers as Drug Delivery Systems, M. Chasin & R. Langer, Ed. (Marcel Dekker, New York), 1990. See also, Jones, D., Pharmaceutical Applications of Polymers for Drug Delivery, ISBN 1-85957-479-3, ChemTec Publishing, 2004. Formulations described in either of these references can be used. In certain embodiments the sustained release materials are co-polymers of lactic acid and glycolic acid wherein the weight ratio of lactic acid to glycolic acid is no more than 4:1 (i.e., 80% or less lactic acid to 20% or more glycolic acid by weight). Certain co-polymers of use have a mole percent composition of about 50% lactide and 50% glycolide. Other ratios include 65:35, 75:25, and 85:15. Certain pharmaceutically acceptable polyanhydrides of use in the present invention have a water-labile anhydride linkage. The rate of drug release can be controlled by the particular polyanhydride polymer utilized and its molecular weight. The polyanhydride polymer may be branched or linear. Other polymers useful in various embodiments of the invention include polyamides, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and co-polymers thereof, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene, polyvinylpyrrolidone, poly(butyric acid), poly(valeric acid), and poly(lactide-cocaprolactone). Peptides, polypeptides, proteins such as collagen or albumin, polysaccharides such as sucrose, chitosan, dextran, alginate, hyaluronic acid (or derivatives of any of these) and dendrimers (e.g., PAMAM dendrimers) are also of use. Methods for preparation of such formulations will be apparent to those skilled in the art. Liposomes or other lipid-containing particles can be used to locally administer a therapeutic agent. Additional exemplary polymers include cellulose derivatives such as, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxymethylcellulose, carboxylethyl cellulose, cellulose triacetate, cellulose sulphate sodium salt, polycarbamates or polyureas, cross-linked poly(vinyl acetate) and the like, ethylene-vinyl ester copolymers having an ester content of 4 to 80% such as ethylene-vinyl acetate (EVA) copolymer, ethylene-vinyl hexanoate copolymer, ethylene-vinyl propionate copolymer, ethylene-vinyl butyrate copolymer, ethylene-vinyl pentantoate copolymer, ethylene-vinyl trimethyl acetate copolymer, ethylene-vinyl diethyl acetate copolymer, ethylene-vinyl 3-methyl butanoate copolymer, ethylene-vinyl 3-3-dimethyl butanoate copolymer, and ethylene-vinyl benzoate copolymer, or mixtures thereof. Chemical derivatives of the afore-mentioned polymers, e.g., substitutions, additions of chemical groups, for example, alkyl, alkylene, hydroxylations, oxidations, and other modifications routinely made by those skilled in the art can be used. In some embodiments of the invention, materials that do not detectably activate complement when assessed in a suitable assay are used. In some embodiments of the invention, materials are selected that do not activate complement by more than 10% above baseline levels when present in amounts at which they would be administered to an extravascular location to treat a complement-mediated disorder.

In certain embodiments a biodegradable sustained release material degrades in vivo over a period of less than about two years, in some embodiments with at least 50% of the sustained release material degrading within about one year, and in some embodiments six months or less. In some embodiments the sustained release material will degrade significantly within one to three months, with at least 50% of the material degrading into non-toxic residues which are removed by the body, and 100% of the drug being released within a time period from about two weeks to about two months. In some embodiments the sustained release material degrades by hydrolysis. In some embodiments degradation occurs by surface erosion, rather than by bulk erosion. The pharmacokinetic release profile of the formulations may be first order, zero order, bi- or multi-phasic, to provide the desired effect over the desired time period.

A method of making a sustained release formulation involves combining or mixing the therapeutic agent with a polymeric component to form a mixture. The mixture may then be extruded, compressed, molded, etc., to form a single composition. Optionally, heat and/or pressure can be used. The single composition may then be processed to form individual implants or particles suitable for administration to an extravascular location. Additional methods for incorporating therapeutically active agents into polymeric matrices are known in the art. The polymeric matrix can be formed into various shapes such as rods, disks, wafers, etc., which may have a range of different dimensions (e.g., length, width, etc.) and volumes. Exemplary shapes include spherical, cylindrical, helical, coil-shaped or helical, screw-shaped, cubical, conical, ellipsoidical, biconvex, hemispherical or near-hemispherical etc. The implant may be shaped appropriately to fit into an extravascular location of interest such as a joint space. In particular embodiments the implant has a length or other longest dimension of between about 1 mm and about 20 cm, or between about 1 cm and about 10 cm. In certain embodiments the implant is at least somewhat flexible, which may facilitate accommodation of the implant at its site of administration. The total weight of the implant may be about 250 µg-100 g, e.g., about 10 mg-10 g. In some embodiments the weight is between 100 mg and 1 g. In some embodiments the weight is between 1 g and 10 g. In some embodiments the weight is between 10 g and 50 g.

In certain embodiments of the invention an implant is so dimensioned and shaped that it fits within the hollow shaft of an injection needle, e.g., a 22, 25, 27, 30, 33, or 35 gauge needle (or needle of any gauge ranging between 22 and 35). Without limitation, such implants may be useful, for example, to treat individual skin lesions such as psoriatic plaques. Exemplary and nonlimiting dimensions for a cylindrical implant may be about 0.5 to 8 millimeters in length and about 0.1 to 2 millimeters in diameter, e.g., about 0.75 mm to about 1.5 mm in diameter. Implants having other shapes, e.g., other rodlike structures with cross-sections that are rectangular or square in cross-section may have a cross-section in which the two points most distant from each other are separated by at most 0.1 mm to 1 mm. In particular embodiments the implant may have a length or other longest dimension of between about 5 microns and about 2 mm, or between about 10 microns and about 1 mm for administration with a needle. Alternately, the length or other longest dimension is greater than 1 mm, or greater than 2 mm, such as 3 mm or up to 10 mm. In certain embodiments of the invention the implants may also be at least somewhat flexible, which may facilitate accommodation of the implant at its site of administration. The total weight of the implant may be about 250-5000 micrograms, e.g., about 500-1000 micrograms. For example, an implant may be about 500 micrograms or about 1000 micrograms. Larger implants may also be formed and further processed before administration. In addition, larger implants may be desirable where relatively greater amounts of a therapeutic agent are to be provided in the implant.

In one embodiment the sustained release formulation is a biocompatible implant comprising a substantially impermeable polymeric outer layer covering a core which comprises the drug to be delivered, wherein said outer layer has one or more orifices, by which is meant one or more openings in the outer layer through which, when the device is in use, body fluids can enter the device and the drug contained in the device (e.g., dissolved, encapsulated, or entrapped within the device) can migrate out of the device. In certain embodiments the orifices in total have a surface area of less than 10 percent of the total surface area of the device. In certain embodiments of the invention the implant comprises an outer coating layer that is permeable to the therapeutic agent, allowing its slow diffusion out of the implant. The composition, structure, and/or thickness of the coating layer may be selected to provide a particular permeability and diffusion rate.

A therapeutic agent can be contained in an implant as a dry powder, particles, granules, or as a compressed solid. The drug may also be present as a solution or be dispersed in a polymer matrix. Implants may have the active agent or agents homogenously distributed through the polymeric matrix, e.g., they may be monolithic. In other embodiments the active agent(s) are heterogeneously distributed in the polymeric matrix. For example, discrete regions of the implant may contain solid particles of an active agent, or a reservoir of active agent may be encapsulated by the polymeric matrix. The therapeutic agent(s) may be distributed in a non-homogenous pattern in the matrix. For example, an implant may include a portion that has a greater concentration of the therapeutic agent relative to a second portion of the implant. Multilayered structures, with the layers having different compositions and may have different physical characteristics such as density or porosity are another embodiment. For example, the layers may contain different therapeutic agents or combinations thereof. In another embodiment, layers that are relatively resistant to degradation are interspersed with layers that degrade more rapidly.

In some embodiments the complement inhibitor is encapsulated within a solid matrix formed of a biocompatible first solid-phase material. The complement inhibitor contained within the solid matrix can be a solid, a liquid, in a suspension, in an emulsion or in a solution in various embodiments.

The biodegradable polymeric materials which form the matrix may be subject to enzymatic or hydrolytic instability. Water soluble polymers may be cross-linked with hydrolytic or biodegradable unstable cross-links to provide useful water insoluble polymers. The degree of stability can vary widely, depending, for example, upon the choice of monomer, whether a homopolymer or copolymer or mixture, is employed, and whether the polymer includes terminal acid groups. The biodegradation of the polymer and hence the extended release profile of the sustained release formulation may also influenced by the relative average molecular weight of the polymeric materials employed. Different molecular weights of the same or different polymeric materials may be included in the formulations to modulate the release profile. For example, the average molecular weight of the polymer may range from about 5 to about 500 kD, e.g., from about 10 to 100 kD, or from about 15 to 50 kD.

In certain embodiments the implant is an article of manufacture coated with a release layer, e.g., comprising a polymer and a complement inhibitor. Thus the invention provides an implant comprising: (a) an implantable article of manufacture; (b) a release layer disposed over at least a portion of the implant; and (c) a complement inhibitor. The release layer comprises a polymer, which in certain embodiments comprises styrene or a styrene copolymer and, optionally, at least one additional polymer. The article could be intended for delivery of the complement inhibitor but may have one or more additional functions as well. For example, in certain embodiments the article is a prosthesis such as an artificial joint or an orthopedic appliance or hardware such as a screw, rod, etc. Exemplary methods for producing an article coated with a release layer are provided in U.S. Pat. No. 7,105,175 and will be adapted for articles suited for extravascular administration. In certain embodiments the implant is administered in associated with an operative or interventional procedure at a joint or bone. In one embodiment such procedure comprises arthroscopic surgery. In certain embodiments the procedure is a standard surgical technique selected from the group consisting of: cartilage shaving, abrasion chondroplasty, laser repair, debridement, chondroplasty, microfracture with or without subchondral bone penetration, mosaicplasty, cartilage cell allograft, stem cell autografts, costal cartilage grafts, chemical stimulation, electrical stimulation, perichondral autografts. In some embodiments the method results in an elevated local concentration of the agent relative to its concentration in the blood. Other methods of modifying an orthopedic device to locally release a complement inhibitor are also within the scope of the invention.

The invention encompasses administering the compositions to sites of injury or surgery. The compositions may be administered to inhibit post-surgical inflammation.

The invention provides a composition comprising a population of particles that comprise a complement inhibitor, wherein the composition is suitable for administration to an extravascular location and the composition is capable of releasing the complement inhibitor in an amount effective to treat a complement-mediated disorder affecting the respiratory system, nervous system, musculoskeletal system, and integumentary system when a suitable amount of the composition is administered to the extravascular location. Nanoparticles or microparticles can be made using any method known in the art including, but not limited to, spray drying, phase separation, single and double emulsion, solvent evaporation, solvent extraction, and simple and complex coacervation. Particulate polymeric compositions can also be made using granulation, extrusion, and/or spheronization. See, e.g., U.S. Publication No. 20040092470. A composition can contain nanoparticles or microparticles having different compositions and/or properties. The conditions used in preparing the particles may be altered to yield particles of a desired size or property (e.g., hydrophobicity, hydrophilicity, external morphology, density, hardness, "stickiness", shape, etc.). The method of preparing the particle and the conditions (e.g., solvent, temperature, concentration, air flow rate, etc.) used may also depend on the therapeutic agent and/or the composition of the polymer matrix. It is generally desirable to avoid extremes of temperature or pH that could result in significant degradation of the complement inhibitor. It will be appreciated that the extent of degradation may be a function of both the particular conditions and the time over which the complement inhibitor is exposed to the conditions, as well as the structure and properties of the agent itself. For example, a stable peptide such as a compstatin analog may have significant advantages. Compositions can be tested to determine whether the method selected is appropriate in terms of retaining sufficient efficacy. In certain embodiments a selected formulation method results in a composition in which, following formulation, the compound retains at least 10% preferably at least 20%, 50%, or more of the level of activity of the input compound.

The method of preparing the particle and the conditions (e.g., solvent, temperature, concentration, air flow rate, etc.) used may also depend on the particular active agents and other components included in the composition. If the particles prepared by any of the above methods have a size range outside of the desired range, the particles can be sized, for example, using a sieve, by milling, etc. Combinations of methods may be employed.

Microparticles and nanoparticles of use in the invention can have a range of dimensions. Generally, a microparticle will have a diameter of 500 microns or less, e.g., between 1 and 500 microns, between 50 and 500 microns, between 100 and 250 microns, between 20 and 50 microns, between 1 and 20 microns, between 1 and 10 microns, etc., and a nanoparticle will have a diameter of less than 1 micron, e.g., between 10 nm and 100 nm, between 100 nm and 250 nm, between 100 nm and 500 nm, between 250 nm and 500 nm, between 250 nm and 750 nm, between 500 nm and 750 micron. 30. In some embodiments the microparticles have a diameter ranging from 5-750 microns. In some embodiments the microparticles have a diameter ranging from 10 to 500 microns. In some embodiments the microparticles have a diameter ranging from 20 to 200 microns. In some embodiments the nanoparticles have a diameter ranging from 5-750 nanometers. In some embodiments the nanoparticles have a diameter ranging from 10 to 500 nanometers. In some embodiments the nanoparticles have a diameter ranging from 20 to 200 nanometers. In some embodiments the size is selected to minimize or avoid transport across capillary walls, thereby minimizing entry into the vascular system.

In some embodiments the microparticles or nanoparticles are formed from a polymer selected from the group consisting of hyaluronan, chitosan, collagen, gelatin, alginate, polylactic acid (PLLA), polyglycolic acid (PGA) and PLGA or combinations of the foregoing. Particles can be substantially uniform in size (e.g., diameter) or shape or may be heterogeneous in size and/or shape. They may be substantially spherical or may have other shapes, in which case the relevant dimension will be the longest straight dimension between two points on the surface of the particle rather than the diameter. The particle population can consist of between about 20% and about 100% particles falling within any of the afore-mentioned size ranges, e.g. about 40%, 40%, 50%, 60%, 70%, 80%, 90%, etc.

In another embodiment sustained release biocompatible and biodegradable microcapsules, optionally having no or minimal burst release, which can be programmed to release their active core for variable durations ranging from 1-100 days in an aqueous physiological environment are prepared. The microcapsules are comprised of a core of complement inhibiting polypeptide or other complement inhibitor encapsulated in a matrix of poly(lactide/glycolide) copolymer having a molar composition of lactide/glycolide from 90/10 to 40/60, which may contain a pharmaceutically-acceptable excipient, as a blend of uncapped free carboxyl end group and end-capped forms ranging to ratios from 100/0 to 1/99. The microcapsules may be prepared as described in U.S. Pat. No. 6,902,743.

The invention provides a population of particles comprising two or more populations (subpopulations), wherein the subpopulation are distinguishable from one another in one or more characteristics such as size, composition, etc. Each population comprises a complement inhibitor, which may be the same or different. Any combination of two or more different complement inhibitors is envisioned. In certain embodiments a first population comprises particles that release the agent over a first time interval and/or with a first release profile over time, and a second population may comprise particles that release the agent over a second time interval and/or with a second release profile over time. The combined formulation releases the agent over a third time interval with a third release profile over time. The third time interval may be longer than either the first or the second time intervals. The first and second populations may comprise particles made of materials that degrade or erode at differing rates. In another embodiment the particles of different populations have outer layers or coats of differing thickness. In certain embodiments at least one population does not contain a complement inhibitor. In certain embodiments at least one population does not contain a therapeutic agent.

In one aspect, the invention provides a sustained release formulation comprising microcarriers containing a first solid-phase biocompatible material and a complement inhibitor, wherein said microcarriers sustain the in vivo release of the biologically active agent. The composition also contains particles of a second biocompatible solid-phase material wherein the second solid-phase material further sustains the in vivo release of the biologically active agent. Optionally such release is at an extravascular location. In certain embodiments the formulation Comprises (a) microcarrier particles of about one millimeter or less containing an effective amount of a complement inhibitor encapsulated within a first polymer which biocompatible and selected from the group consisting of poly(lactide)s, poly(glycolide)s, poly(lactide-co-glycolide)s, poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetyls, polycyanoacrylates, polyetheresters, poly(dioxanone)s, poly(alkylene alkylate)s, copolymers of polyethylene glycol and polyorthoester, biodegradable polyurethanes, blends and copolymers thereof, wherein the microcarriers sustain the in vivo release of the complement inhibitor, and (b) microparticles of about one millimeter or less of a second polymer which is biocompatible and biodegradable, wherein said microparticles are substantially free of the biologically active agent, and which are separate form but commingled with the microcarrier particles of a) and are present in an amount sufficient to elongate the release period of the complement inhibitor from the microcarrier particles of (a). In some embodiments the first polymer and the second polymer are the same polymer. In other embodiments they are different. In some embodiments the second polymer is selected from the group consisting of poly(lactide)s, poly (glycolide)s, poly(lactide-co-glycolide)s, poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetyls, polycyanoacrylates, polyetheresters, poly(dioxanone)s, poly(alkylene alkylate)s, copolymers of polyethylene glycol and polyorthoester, biodegradable polyurethanes, blends and copolymers thereof. Suitable methods for making the compositions are described in U.S. Pat. No. 5,916,597.

Compositions comprising particles may comprise a pharmaceutically acceptable carrier e.g., a liquid such as sterile water, saline, etc. Particle compositions can be injectable. In certain embodiments of the invention the sustained release formulation comprises liposomes. Liposomes can be prepared according to methods known to those skilled in the art, for example, as described in U.S. Pat. No. 4,522,811 and other references listed herein. Liposomes, including targeted liposomes (e.g., antibody targeted liposomes), pegylated liposomes, and polymerized liposomes have been described (Hansen C B, et al., *Biochim Biophys Acta*. 1239(2):133-44, 1995; Torchilin V P, et al., *Biochim Biophys Acta*, 1511(2): 397-411, 2001; Ishida T, et al., *FEBS Lett.* 460(1):129-33, 1999). In certain embodiments the sustained release formulation does not comprise liposomes or, if liposomes are present, less than 1%, 5%, 10%, or 20% of the complement inhibitor by weight is contained in the liposomes.

In certain embodiments the sustained release formulation comprises a cyclodextrin. The cyclodextrin may be provided in an amount from about 0.5% (w/w) to about 25% (w/w) of the formulation. In certain implants, the cyclodextrin is provided in an amount from about 5% (w/w) to about 15% (w/w) of the formulation. The cyclodextrin may be α, β, or γ-cyclodextrin, or mixtures thereof. Cyclodextrin derivatives are also of use. The cyclodextrin or derivative may be present in an amount effective to enhance the solubility of the therapeutic agent in a fluid or gel phase or matrix in which it is to be dissolved.

In certain embodiments of the invention a sustained release formulation comprises a therapeutic agent and a gel-forming material, also referred to as a gel "precursor". In accordance with certain embodiments of the invention, a solution containing a soluble gel-forming material and a therapeutic agent is prepared by combining gel-forming material and therapeutic agent in solution using any suitable method, e.g., by adding the therapeutic agent to a solution containing soluble gel-forming material or by adding both the therapeutic agent and gel-forming material in dry or liquid form to a suitable solvent. The composition is delivered locally to an appropriate extravascular location in the body of a subject. The solution rapidly forms a gel at or close to of the site of administration. The therapeutic agent is entrapped within the gel. The therapeutic agent diffuses out of the gel or is released as the gel degrades over time, thereby providing a continuous supply of the agent to tissues and structures that are either in direct physical contact with the gel or located nearby. In certain embodiments the solution is administered in or near a joint. In other embodiments the solution is administered intrathecally. Delivery can be accomplished by injection (e.g., using a 25, 27, or 30 gauge needle or the like), by catheter, etc.

Gel formation can occur through a variety of mechanisms. For example, gel formation can be triggered by substances such as ions present in physiological fluids with which the gel precursor comes into contact following administration. In some embodiments an initiating agent such as an ion, salt, cross-linking agent, or polymerization initiator is added to the solution shortly before administration. The solution is administered after a suitable time, typically before significant gel formation has occurred. The exact time will depend, e.g., on the particular gel precursor, initiating agent, and concentrations thereof used. In certain embodiments gel formation occurs at least in part as a result of a change in pH or a change in temperature. For example, gel formation can occur as a result of an increase or decrease in pH and/or temperature of the solution upon administration to an extravascular location of a mammalian subject having a body temperature of about 37° C. In other embodiments gel formation occurs as a result of diffusion of a substance, such as an organic solvent (e.g. ethanol, methanol, ethylene glycol, or N-methylpyrrolidone), out of the solution into surrounding tissues following administration.

Alternately, a preshaped gel implant can be made, e.g., by introducing the solution into a mold or cavity of the desired shape and allowing gel formation to occur. In certain embodiments of the invention gel formation occurs in the presence of a suitable concentration of an ion, salt, cross-linking agent, or polymerization initiator, which can be added to the solution either prior to or following the introduction of the solution into the mold or cavity. The mold or cavity can be, e.g., any structure that contains a hollow space or concave depression into which a solution can be introduced. In another embodiment, a film or membrane is formed from the gel-forming solution containing a therapeutic agent.

In one embodiment, soluble collagen is used as the gel-forming material. The collagen is initially soluble, e.g., in an aqueous medium, and forms a solution that has a low viscosity but is capable of rapid formation of a gel under appropriate conditions, e.g., conditions encountered upon administration to a mammalian subject. A variety of different collagen preparations can be used in the present invention provided that the collagen is initially soluble and is capable of rapidly forming a gel under appropriate conditions. Suitable collagen preparations, and methods for their manufacture, are described, e.g., in U.S. Pat. Nos. 5,492,135; 5,861,486; 6,197,934; 6,204,365; and WO 00/47130, but the invention is not limited to such preparations or methods. These collagens are prepared in soluble form and rapidly form a gel upon exposure to physiological fluids or other fluids having suitable concentration of ions. In accordance with the present invention, injecting or otherwise introducing the collagen solution to an extravascular location results in gel formation, presumably induced by contact with physiological fluids. However it is noted that the invention is in no way limited by the mechanism by which gel formation occurs. In addition, as noted above, the gel can be formed in vitro and then implanted at an appropriate location.

One suitable method of preparing a soluble collagen solution involves extracting collagen from a natural source, acid solubilizing the collagen, and dialyzing the solubilized collagen against a solution containing a chelating agent, e.g., a metal chelating agent such as ethylenediamine tetraacetic acid, disodium salt dihydrate (EDTA), while raising the pH. One or more dialysis steps against a solution such as deionized water lacking the chelating agent may also be performed. Unlike standard collagen solutions that undergo spontaneous fibrillogenesis at neutral pH and room temperature, collagen solutions for use in the present invention remain in solution during storage for extended periods of time and rapidly undergo gel formation when exposed to physiological fluids. The chelating agent may alter the concentration of one or more cations and thereby prevent fibrillogenesis that would otherwise occur as the pH is raised. The chelating agent may have other desirable effects on the collagen solution, and in certain embodiments of the invention the collagen solution comprises a chelating agent, e.g., EDTA. The chelating agent may remain in the collagen solution following dialysis or may be added to the collagen solution. The concentration of the chelating agent may range, for example, between about 0.02M and about 0.05M, e.g., between about 0.025M and about 0.035M. Other chelating agents may also be used including, but not limited to, those described in U.S. Pat. No. 5,861,486.

In certain embodiments the collagen solution has a concentration of soluble collagen ranging between 1 mg/ml and 100 mg/ml, e.g., between 10 mg/ml and 70 mg/ml, between 20 mg/ml and 50 mg/ml, e.g., 30 mg/ml, etc. In certain embodiments of the invention the pH of the collagen solution is between 6.0 and 8.0, e.g., between 6.5 and 7.5, e.g., 7.0.

In certain embodiments of the invention the collagen composition further comprises a fibrillar component comprising fibrillar collagen solids. For example, certain collagen compositions contain between 0.5 mg/ml and 30 mg/ml fibrillar collagen solids, or between 1 mg/ml and 20 mg/ml fibrillar collagen solids, e.g., 2 mg/ml, 3 mg/ml, 4 mg/ml, 5 mg/ml, 6 mg/ml, 8 mg/ml, 10 mg/ml, etc. In terms of percent fibrillar collagen solids on a weight/volume basis, certain collagen compositions contain between 0.05 and 3% fibrillar collagen solids or between 0.1 and 2% fibrillar collagen solids, e.g., 0.2%, 0.3%, 0.4%, 0.5%, 0.6%, 0.8%, 1%, 1.2%, etc. Any suitable fibrillar component can be used in the collagen compositions of the invention. Fibrillar collagen solids can be prepared using a variety of methods. For example, fibrillar collagen may be reconstituted collagen prepared from animal sources such as bovine hide (Frontiers in Matrix Biology, Vol. 10, pp. 1-58, in *Methods of Connective Tissue Research*, Eds. Robert, Moczar, and Moczar, S. Karger, Basel, 1985). Fibrillar collagen may be prepared from human or animal sources as described in U.S. Pat. Nos. 4,969,912 and 5,322,802. The fibrillar collagen solids are suspended in solution at a concentration typically ranging from about 10-100 mg/ml. The collagen suspension containing fibrillar collagen solids is combined with, e.g., added to, a soluble collagen composition either prior to or following addition of the therapeutic agent to a solution comprising soluble collagen.

In some embodiments of the invention the soluble collagen preparation comprises a chemical cross-linking agent. The agent may crosslink collagen molecules and/or fibrils to one another and/or may crosslink a therapeutic agent such as compstatin or an analog thereof to a collagen molecule or fibril. Typical cross-linking agents crosslink collagen amine groups to one another or to amine, carboxyl, phenol, sulfonyl, or carbohydrate groups of therapeutic agents. Suitable cross-linking agents include, but are not limited to, those described in WO 00/47130. Cross-linking may stabilize the collagen gel (e.g., decrease its rate of breakdown) and/or decrease the rate of release of the therapeutic agent from the gel.

The presence of fibrillar collagen solids may have any of a variety of advantageous effects. For example, the fibrillar collagen solids may increase the in vivo stability of the collagen gel, e.g., they may decrease the rate of breakdown of the gel. The fibrillar collagen solids may increase the stability of a therapeutic agent contained in the gel and/or decrease or modulate the rate at which the agent is released from the gel by diffusion and/or breakdown of the gel.

Any of collagen types I-XXVIII, or mixtures thereof, can be used in various embodiments of the present invention. The collagen can be purified from natural sources (e.g., human tissue or animal tissue such as bovine, rabbit, etc.) as described in the above-referenced patents and publications. Alternatively, the collagen can be manufactured using recombinant DNA techniques, in which case the sequence can be of human or animal origin. See, e.g., U.S. Pat. Nos. 5,593,854 and 5,667,839. Methods for the production of proteins, e.g., a polypeptide of interest such as a collagen chain, using recombinant DNA technology are well known in the art. The term "collagen" includes collagen fragments. In certain embodiments the soluble collagen comprises or consists of a collagen fragment or combination of fragments. In certain embodiments a complete collagen polypeptide chain is used. Various modified or derivatized collagens are also of use in various embodiments of the invention. See, e.g., U.S. Pat. No. 5,201,764. Collagen can be acylated with one or more acylating agents such as glutaric anhydride, succinic anhydride, and maleic anhydride and at least one other acylating agent selected from the group consisting of methacrylic anhydride, beta-styrene sulfonyl chloride, ethylene-maleic anhydride copolymer, styrene-maleic anhydride copolymer or poly(vinyl) sulfonic acid.

Other collagen materials of use in the invention are described in U.S. Pat. No. 5,412,076, which discloses a crosslinkable modified collagen which is soluble in water and/or in aprotic polar organic solvents and which comprises free or unsubstituted thiol groups carried by residues of cysteine, at least some of said residues being fixed to the collagen via spacer compounds. In certain embodiments the spacer compounds are carboxylated hydrocarbon units. Yet other collagen materials of use in the invention are described in U.S. Pat. No. 6,916,909, which discloses collagen peptides that are modified by grafting free or substituted thiol functions carried by mercaptoamine radicals. In certain embodiments the mercaptoamino residues are identical to or different than each other and are exclusively grafted onto the aspartic acids and glutamic acids of the collagenic chain via amide bonds, and optionally said collagenic peptide is soluble in aqueous media and/or in polar solvents.

Other gel-forming materials of use in the invention include, but are not limited to, hyaluronic acid and modified forms thereof, polysaccharides such as alginate and modified forms thereof, carbomers, self-assembling peptides, etc. See, e.g., U.S. Pat. No. 6,129,761 for further description of alginate and modified forms thereof, hyaluronic acid and modified forms thereof, and additional examples of soluble gel-forming materials that are of use in various embodiments of the present invention. As described therein, other polymeric hydrogel precursors include polyethylene oxide-polypropylene glycol block copolymers such as Polaxmers, e.g., Pluronics™ or Tetronics™ which are crosslinked by hydrogen bonding and/or by a temperature change, as known in the art. Other materials which may be utilized include proteins such as fibrin or gelatin. Polymer mixtures also may be utilized. For example, a mixture of polyethylene oxide and polyacrylic acid which gels by hydrogen bonding upon mixing may be utilized. The composition may comprise a cross-linking agent, polymerizing agent such as a polymerization initiator, etc.

Typically a gel-forming material of use in the invention is capable of being at least partly dissolved, or in certain embodiments of the invention substantially or fully dissolved, e.g., in an aqueous medium. For example, at least 50%, at least 60%, at least 70%, at least 80%, at least 90%, at least 95%, or more, by weight, of the gel-forming material present in a gel-forming composition may be dissolved. In certain embodiments essentially 100% of the material is dissolved. It will be appreciated that the aqueous medium can contain one or more liquids in addition to water, e.g., various alcohols. In general, at least 10%, 20%, 30%, 40%, 50%, 60%, 70%, 80%, 90%, 95%, or about 100% of the liquid present in the medium is water.

Covalently crosslinkable hydrogel precursors also are useful. For example, a water soluble polyamine, such as chitosan, can be cross-linked with a water soluble diisothiocyanate, such as polyethylene glycol diisothiocyanate. The isothiocyanates will react with the amines to form a chemically crosslinked gel. Aldehyde reactions with amines, e.g., with polyethylene glycol dialdehyde also may be utilized. A hydroxylated water soluble polymer also may be utilized.

In certain embodiments of the invention a therapeutic agent is covalently or noncovalently attached to a drug delivery regulating component such as a polymer via a linking moiety. The linking moiety may be cleaved to release the therapeutic agent from the drug delivery regulating component to provide sustained release. For example, the linking moiety may be a peptide containing a site that is cleaved by an endogenous enzyme such as a protease, or the linking moiety may contain a labile or hydrolyzable bond.

Alternatively, polymers may be utilized which include substituents which are crosslinked by a radical reaction upon contact with a radical initiator. For example, polymers including ethylenically unsaturated groups which can be photochemically crosslinked may be utilized, as disclosed in WO 93/17669, the disclosure of which is incorporated herein by reference. In this embodiment, water soluble macromers that include at least one water soluble region, a biodegradable region, and at least two free radical-polymerizable regions, are provided. The macromers are polymerized by exposure of the polymerizable regions to free radicals generated, for example, by photosensitive chemicals and or light. Examples of these macromers are PEG-oligolactyl-acrylates, wherein the acrylate groups are polymerized using radical initiating systems, such as an eosin dye, or by brief exposure to ultraviolet or visible light. Additionally, water soluble polymers which include cinnamoyl groups which may be photochemically crosslinked may be utilized, as disclosed in Matsuda et al., ASAID Trans., 38:154-157 (1992). In certain embodiments the polymers are at least partially soluble in aqueous solutions, such as water, buffered salt solutions, or aqueous alcohol solutions.

Methods for the synthesis of the other polymers described above are known to those skilled in the art. See, for example Concise Encyclopedia of Polymer Science and Polymeric Amines and Ammonium Salts, E. Goethals, editor (Pergamen Press, Elmsford, N.Y. 1980). Many polymers, such as poly (acrylic acid), are commercially available. Naturally occurring and synthetic polymers may be modified using chemical reactions available in the art and described, for example, in March, "Advanced Organic Chemistry," 4th Edition, 1992, Wiley-Interscience Publication, New York.

Water soluble polymers with charged side groups may be crosslinked by reacting the polymer with an aqueous solution containing ions of the opposite charge, either cations if the polymer has acidic side groups or anions if the polymer has basic side groups. Examples of cations for crosslinking of the polymers with acidic side groups to form a hydrogel are monovalent cations such as sodium, and multivalent cations such as copper, calcium, aluminum, magnesium, strontium, barium, and tin, and di-, tri- or tetra-functional organic cations such as alkylammonium salts. Aqueous solutions of the salts of these cations are added to the polymers to form soft, highly swollen hydrogels and membranes. The higher the concentration of cation, or the higher the valence, the greater the degree of cross-linking of the polymer. Additionally, the polymers may be crosslinked enzymatically, e.g., fibrin with thrombin. In some embodiments a self-assembling peptide, such as those described in U.S. Pat. No. 6,800,481 is used.

These peptides self-assemble to form a hydrogel structure upon contact with monovalent cations, e.g., such as those present in extracellular fluid.

In embodiments of the invention in which the gel is formed by cross-linking polymer chains to one another, the composition can include an appropriate cross-linking agent, which is selected according to the particular polymer. Alternately, the cross-linking agent can be administered after administration of the composition containing the gel-forming material, at substantially the same location. Any of these gels can be formed in vitro, e.g., as described above for gels comprising soluble collagen, and implanted at an appropriate extravascular location.

In certain embodiments of the invention the composition contains cells that produce and secrete a complement inhibitor instead of, or in addition to, the molecule itself. In these embodiments, the gel may be resistant to degradation, so that it traps the cells therein for a sustained period of time.

In certain embodiments the compositions form a gel within 5 minutes following administration. In certain embodiments the preparations form a gel within 90 seconds, 2 minutes, or 3 minutes following administration. In certain embodiments a gel is formed between 5-90 seconds following administration. In other embodiments a gel is formed within 3-5 minutes following administration.

The total volume of the solution administered may range from about 50 µl-100 ml. In certain embodiments the amount is 50 µl-100 µl, 100 µl-1 ml, 1 ml-5 ml, 5 ml-10 ml, 10 ml-50 ml, or 50 ml-100 ml. In some embodiments the weight of the formed gel is between 250 µg-100 g, e.g., about 10 mg-10 g. In some embodiments the weight is between 100 mg and 1 g. In some embodiments the weight is between 1 g and 10 g. In some embodiments the weight is between 10 g and 50 g.

The invention further provides a composition comprises (i) a population of particles comprising a complement inhibitor; and (ii) a continuous biocompatible matrix or precursor thereto. The matrix may be a gel, solid or semi-solid polymeric matrix, etc. The precursor is a material used to form the bulk of the matrix. The particles may be nanoparticles, microparticles, lipid-based particles (e.g., liposomes), niosomes, etc. The particles may be uniform or non-uniform in terms of their material composition and/or size. The population may comprise multiple subpopulations each of which has one or more uniform characteristics, e.g., as described above. In certain embodiments the matrix is a gel such as those described above.

One aspect of the invention is sustained release preparations having desirable release kinetics. In one embodiment less than 50% of the total complement inhibitor is released within the first 48 hours following administration. In one embodiment less than 25% of the total complement inhibitor is released within the first 48 hours following administration. In one embodiment less than 50% of the total complement inhibitor is released within the first week following administration. In one embodiment less than 25% of the total complement inhibitor is released within the first week following administration. In certain embodiments there is a biphasic release profile wherein a first fraction of the administered dose (e.g., up to 50%) is rapidly released (e.g. within the 12, 24, or 48 hours) and a second fraction of the administered dose is released at a different rate, e.g., a less than 0.1 times the rate at which the second fraction is released. In some embodiments there is a first phase (e.g., 12, 24, or 48 hours) in which a first fraction of the total dose is released, and a second phase in which the time required to release an equal amount of the dose as released during the first phase is at least or about 5, 10, 20, 50, or 100 times as long as the first phase. In some embodiments the second phase is between or at least 2-4 weeks, between or at least 1-3 months, between or at least 3-6 months, or between or at least 6-12 months. In some embodiments the release profile is triphasic. In one embodiment a bolus is administered together with or within up to 2 hours prior to or following administration of a sustained release preparation.

The present invention contemplates use of a variety of sustained release formulations and methods for their manufacture known in the art. These formulations and methods comprise or are applied to a complement inhibitor with appropriate modifications as necessary. In general, any complement inhibitor can be used in various embodiments of the invention, it being recognized that certain formulations are more advantageously employed with complement inhibitors having particular physicochemical properties as described or evident to one of skill in the art upon reading the instant specification. The invention provides a composition comprising a complement inhibitor complexed or mixed with a substance having an opposite charge to the complement inhibitor. The substance may be a lipid, polysaccharide, or polymer having a plurality of acidic moieties (e.g., carboxyl moieties or phosphonic acid moieties) or basic moieties (e.g., amine moieties). In some embodiments the substance is an alkali metal, alkaline earth metal, or polyvalent metal.

The composition may be used in preparation of a sustained release formulation or device. The substance may reduce degradation and/or facilitate sustained release. The invention provides a composition comprising a complement inhibitor and an organic solvent. Organic solvents as used herein refer to any carbon-based liquid solvent. Exemplary organic solvents include methylene chloride, ethyl acetate, dimethyl sulfoxide, tetrahydrofuran, dimethylformamide, and ethanol. In some embodiments the organic solvent is an alcohol, e.g., having 1 to 10 carbon atoms, such as methanol, ethanol, iso-propanol, n-propanol, or t-butanol, as well as glycerol, propylene glycol, ethylene glycol, hexylene glycol, polypropylene glycol, and polyethylene glycol, and most preferably ethanol or iso-propanol. Other organic solvents are substituted heterocyclic compounds, esters of carbonic acid and alkyl alcohols, alkyl esters of monocarboxylic acids, alkyl esters of dicarboxylic acids, alkyl esters of tricarboxylic acids, alkyl ketones, alcohols, dialkylamides, dimethylsulfoxide (DMSO), dimethylsulfone, tetrahydrofuran, lactones, cyclic alkyl amides, aromatic amides, mixtures and combinations thereof. In some embodiments alcohols are solvents that, when added to aqueous solution, increase the hydrophobicity of the solution by decreasing solution polarity.

In another aspect, this sustained release formulation comprises an ionic conjugate containing a free carboxyl group-containing biodegradable polymer such as a polyester made of monomers such as lactic acid, ε-caprolic acid, glycolic acid, trimethylene carbonate, or p-dioxanone; or a copolymer thereof and a free amino group-containing complement inhibitor (e.g., a peptide drug such as a compstatin analog) which are ionically bonded to each other. The drug may have, e.g., 1-10 free amino groups. The sustained release formulation may be in the form of nanoparticles or microparticles or in the form of a shaped article. Suitable methods and materials for making the sustained release formulation are described in U.S. Pat. No. 6,911,218, wherein a complement inhibitor is used as an active agent.

In one embodiment the sustained release formulation is hydrogel composition that contains (a) a polymer material and (b) an effective amount of a complement inhibitor. The polymer materials used in the hydrogel composition have reverse gelation properties and exist as a liquid, aqueous solution at temperatures below physiological temperatures (e.g., below the body temperature of a patient) but form hydrogels under physiological conditions (e.g., at temperatures at or near the body temperature of a patient). The compositions may thus be administered to a patient by injection while they are in a liquid state. Upon administration the carrier hydrogel compositions then form hydrogels with the complement inhibitor embedded therein. Suitable methods and materials for making the sustained release formulation are described in U.S. Pat. No. 6,541,020, wherein a complement inhibitor is used as an active agent.

In one embodiment the sustained release formulation comprising microcapsules that provide for sustained release of water soluble peptides, with adjustable release periods of between 1 to 18 weeks. The microcapsule walls are made of a biodegradable polymer. Suitable methods and materials for making the sustained release formulation are described in U.S. Pat. No. 6,534,094, wherein a complement inhibitor is used as an active agent. One such process is based on the formation of an intermediate complex water/oil/water emulsion. By evaporating the solvent in the emulsion by pressure reduction the microcapsules consolidate, retaining the active peptides in the polymeric matrix. The process produces the complex emulsion in a two mixer, continuous operation. In the first mixer a water/oil emulsion is formed and it is used to form the complex emulsion in the second mixer.

In one embodiment the invention provides sustained release microcapsules of complement inhibitor and a biodegradable polymer. Suitable methods and materials for making the sustained release formulation are described in U.S. Pat. No. 6,419,961, wherein a complement inhibitor is used as an active agent. One such method comprises obtaining microcapsules comprising a bioactive substance that are encapsulated with a biodegradable polymer, and thermally drying the obtained microcapsules at a temperature not lower than the glass transition temperature of the biodegradable polymer for about 24 to about 120 hours to produce the sustained-release microcapsules comprising, relative to the weight of the sustained-release microcapsule, not less than 60% (w/w) of the biodegradable polymer. In certain embodiments the complement inhibitor is released at essentially or approximately constant rate over a very long period of time from just after administration with dramatically suppressed initial release of the complement inhibitor in excess just after administration and with minimum remaining organic solvent.

In another aspect the invention provides a composition comprising a complement inhibitor contained within polymeric microparticles, wherein a mixture of the complement inhibitor and the polymer are dispersed within a continuous phase, and the resulting dispersion is directly lyophilized to remove the water and organic solvents and form said microparticles. The continuous phase may be aqueous or organic. In certain embodiments the complement inhibitor-polymer mixture is obtained by dispersing an aqueous solution of the complement inhibitor in a second, non-aqueous phase containing the polymer, prior to addition to the continuous phase. In certain embodiments the active ingredient-polymer mixture is obtained by dissolving both components in a non-aqueous solvent prior to addition to the continuous phase. In certain embodiments the active ingredient is present as a dispersion of solid particles in a non-aqueous solution of the polymer, which is then added to the continuous phase. In certain embodiments the complement inhibitor is omitted from the mixture, thereby producing blank polymeric microparticles, and the complement inhibitor is loaded onto said blank polymeric microparticles by suspending said blank polymeric microparticles in active ingredient solution. Suitable methods and materials for making the sustained release formulation are described in U.S. Pat. No. 6,020,004, wherein a complement inhibitor is used as an active agent. It will be appreciated that the particle loading method is applicable to a wide variety of particles compositions.

Further provided by the present invention is a sustained release delivery system for delivering a complement inhibitor. The system includes a reservoir comprising the complement inhibitor and a capillary channel in communication with the reservoir and the exterior of the system for delivering the complement inhibitor from the system. The capillary channel has a cross-sectional area and a length selected to deliver the complement inhibitor at a predetermined rate. The system may further include an outer surface that is impermeable and non-porous during delivery of the complement inhibitor. The complement inhibitor may be formulated in a glassy sugar matrix. In one embodiment an entirety of a reservoir that encloses the complement inhibitor is impermeable and non-porous to fluids external of said reservoir during delivery of the complement inhibitor. Suitable methods and materials for making the sustained release formulation are described in U.S. Pat. No. 6,261,583. A complement inhibitor is used as an active agent.

The invention further provides an implant composition for sustained delivery of a biologically active agent. The implant composition includes a complement inhibitor, a thermoplastic polymer, an organic liquid and a small amount of an aqueous medium. The thermoplastic polymer is insoluble in water so that the implant composition has the form of a substantially homogeneous pliable, moldable solid. Suitable methods and materials for making the sustained release formulation are described in U.S. Pat. No. 6,261,583. A complement inhibitor is used as an active agent.

In another embodiment the invention provides a flowable composition for forming a solid biodegradable implant in situ within a body, comprising: (a) a complement inhibitor; (b) a non-polymeric, water-insoluble material that is biodegradable, (c) a minor amount of biodegradable, bioabsorbable thermoplastic polymer; (d) a biocompatible, organic solvent that is miscible to dispersible in water or body fluids, and capable of dissipating, diffusing or leaching from the composition into body fluid upon placement within a body, whereupon the non-polymeric material coagulates or precipitates to form the implant. Suitable methods and materials for making the sustained release formulation are described in U.S. Pat. No. 6,120,789. A complement inhibitor is used as an active agent.

In another embodiment the invention provides solid dose delivery systems for administration of a complement inhibitor. The delivery systems comprise a vitreous vehicle loaded with the complement inhibitor and capable of releasing it in situ at various controlled rates. In one embodiment, the vehicle is a hydrophobic carbohydrate derivative (HDC). Suitable methods and materials for making the sustained release formulation are described in U.S. Pat. No. 6,586,006. A complement inhibitor is used as an active agent.

In one embodiment the invention provides an implant made from an implant precursor having a two-part structure made of an outer sac and a liquid content. The implant precursor is composed of a biodegradable, water-coagulable thermoplastic polymer and a water-miscible organic solvent. When administered to an implant site in a mammal, the implant precursor, having a complement inhibitor included therewith, solidifies in situ to a solid, microporous matrix by dissipation of the organic solvent to surrounding tissue fluids and coagulation of the polymer. Suitable methods and materials for making the implant precursor and implant are described in U.S. Pat. No. 6,395,293. A complement inhibitor is used as the active agent.

In another embodiment the invention provides a sustained release polymeric composition which includes a base polymer or copolymer, an organic solvent, a polymeric controlled release additive, and a complement inhibitor. The polymeric controlled release additive reduces the initial burst of complement inhibitor released from the polymeric composition as it is solidifying to form the solid implant. The controlled release additive is a poly(lactide-co-glycolide)/polyethylene glycol block copolymer in certain embodiments. In certain embodiments the polymeric composition is capable of forming the implant by dissipation or dispersement of the organic solvent within the body. In certain embodiments the poly(lactide-co-glycolide)/polyethylene glycol block copolymer includes from about 50 mole % to about 90 mole % lactide monomers and about 50 mole % to about 10 mole % glycolide monomers. Suitable methods and materials for making the implant precursor and implant are described in U.S. Pat. No. 6,630,155. A complement inhibitor is used as the active agent.

In another embodiment the invention provides a sustained release formulation comprising a biocompatible, bioerodable polymer having dispersed therein a glassy matrix phase comprising a peptide or polypeptide complement inhibitor and a thermoprotectant, said glassy matrix phase having a glass transition temperature above the melting point of the polymer. In certain embodiments the thermoprotectant is selected from the group consisting of trehalose, lactose, maltose, cellobiose, melezitose, melibiose, raffinose and sucrose. In certain embodiments the biocompatible, bioerodable polymer is polycaprolactone. Suitable methods and materials for making the formulation are described in U.S. Pat. No. 6,187,330.

A variety of sustained release formulations for delivering an active agent, and suitable methods and materials for their manufacture, are described in U.S. Pat. Nos. 6,451,335 and 6,419,961. Such formulations, wherein at least one active agent is a complement inhibitor, are an aspect of the invention.

A sustained release formulation may include an excipient component, such as a bulking agent, buffering agent, stabilizer, preservative, and the like. Water soluble buffering agents include alkali and alkaline earth carbonates, phosphates, bicarbonates, citrates, borates, acetates, succinates and the like, such as sodium phosphate, citrate, borate, acetate, bicarbonate, carbonate and the like. These agents are optionally present in amounts sufficient to maintain a pH of the formulation of between about 2 to about 9, e.g., about 4 to about 8. Suitable water soluble preservatives include sodium bisulfite, sodium bisulfate, sodium thiosulfate, ascorbate, benzalkonium chloride, chlorobutanol, thimerosal, phenylmercuric acetate, phenylmercuric borate, phenylmercuric nitrate, parabens, methylparaben, polyvinyl alcohol, benzyl alcohol, phenylethanol and the like and mixtures thereof. In certain embodiments the stabilizer is a polyol which term denotes a hydrocarbon including at least two hydroxyls bonded to carbon atoms. Polyols may include other functional groups. Polyols in certain embodiments have a molecular weight less than about 70,000 kD. Examples of useful polyols include sugar alcohols such as mannitol and trehalose, and polyethers such as polyethylene glycol. See U.S. Pat. No. 5,589,167, "Polyether" as used herein denotes a hydrocarbon containing at least three ether bonds. Polyethers may include other functional groups. Polyethers useful for practicing the invention include polyethylene glycol (PEG). In certain embodiments a stabilizing agent is an agent that inhibits aggregation of a complement inhibitor. Buffering agents, preservatives, stabilizers, etc., may be present in amounts of from 0.001 to about 5% by weight, e.g., about 0.01 to about 2% by weight. These agents may also be used in liquid compositions lacking drug release regulating components. A sustained release formulation may contain a variety of additional components that lack therapeutic activity and that may or may not contribute to the sustained release features of the formulation. Examples include plasticizing agents, solubilizing agents, solubility decreasing agents, and dispersing agents (see U.S. Pat. No. 6,331,313), provided that such components are compatible with administration under the conditions used.

One of ordinary skill in the art will appreciate that the materials and methods selected for preparation of a sustained release formulation, implant, etc., should be such as to retain activity of the compound. For example, it may be desirable to avoid excessive heating of certain agents such as polypeptides, which could lead to denaturation and loss of activity.

In some embodiments of the invention the sustained release formulation comprises a delivery agent that enhances delivery of the agent to a desired site of action, enhances bioavailability of the agent, or otherwise enhances activity of the agent. In certain embodiments the delivery agent increases tissue permeability. The delivery agent may increase membrane permeability via a paracellular route, e.g., via tight junctions. Exemplary compounds are described in U.S. Pat. Pub. No. 20040077540 and include a peptide or peptide analog or mimetic selected or derived from an extracellular domain of a mammalian JAM, occludin or claudin protein. A composition comprising a complement inhibitor and a tissue permeability enhancer may be administered nasally (e.g., by nasal spray) to deliver the complement inhibitor to the central nervous system.

Included within the scope of the term "sustained release formulation" are devices or "chips" that include one or more reservoirs containing the agent and that release the agent or a portion thereof from the one or more reservoirs into the surrounding area (see, e.g., U.S. Pat. Nos. 5,797,898 and 6,976, 982). Release may occur through a variety of means. For example, the reservoirs may have a biodegradable cap that is impermeable to the agent and degrades over time, so that the therapeutic agent is released once the cap is degraded. Caps of differing thickness will cause release to occur at different times. Mechanical, electrical, or other means may be used to release the agent from a reservoir, optionally using external control means to regulate such release. Release can occur at predetermined times and/or in predetermined amounts. The device may be programmable.

Other sustained release devices of use in the invention include devices such as pumps that effect infusion of a substantially fluid material to a location in the body in a continuous, substantially continuous, or intermittent manner. The device may be programmed to release predetermined amounts of the agent at predetermined time intervals. U.S. Pat. No. 4,692,147, assigned to Medtronic, Inc., Minneapolis, Minn., describes a suitable pump. In certain embodiments one or more of the infusion systems known as the Synchromed® Infusion System manufactured by Medtronic, Inc. of Minneapolis, Minn. (see web site having URL www.medtronic.com) is used. However, it will be appreciated that the pump may take the form of any device used for moving fluid from a reservoir. Mechanical, pressure-based, osmotic, or electrokinetic means may be used.

For example, in order to deliver an agent to the brain parenchyma, a catheter attached to the pump may be implanted so that the discharge portion lies in the brain parenchyma. See, e.g., U.S. Pat. No. 6,263,237 for description of a variety of suitable systems and methods for implanting them into the body of a subject and directing the administration of an active agent to a desired location in the brain. Continuous intracerebral microinfusion is a technique of regional delivery of therapeutic agents directly into brain parenchyma. It establishes a bulk flow current that has the potential to homogeneously distribute even large molecules.

In certain embodiments of the invention the agent is delivered to one or more of the cavities or chambers of the central nervous system that contain cerebrospinal fluid (CSF), e.g., the ventricles or cisterna magna. To deliver an agent to a ventricle or the cisterna magna using an infusion pump, the catheter may be implanted so that the discharge portion lies in the ventricle or the cisterna. The agent diffuses out of the ventricle or cisterna magna. Delivery to these locations therefore allows delivery of the agent to a relatively wide area of the brain rather than localizing it more closely to a specific site. In certain embodiments of the invention delivery to a CSF-containing space is accomplished by surgically implanting a catheter through the skull so that the tip has access to the space. The other end of the catheter is then connected to a reservoir (e.g., an Ommaya reservoir), which is placed beneath the scalp (subcutaneously). The agent could also be delivered directly to a region in the brain, e.g., intraoperatively or using sterotactic guidance.

Methods for administering agents intrathecally are well known in the art. If the subject suffers from spinal cord injury, the catheter is implanted so that the discharge portion lies in the intrathecal space while the other end is connected to the pump reservoir. Such methods are commonly used in the treatment of chronic pain, and are routinely used to deliver analgesic agents over a period of months. Similar methods are of use in the present invention.

In one embodiment of the present invention a subject suffering from traumatic brain injury, stroke, or spinal cord injury, is treated systemically with a first complement inhibitor and a second complement inhibitor is administered locally to the CNS. The first and second complement inhibitors may be the same or different. In other embodiments of the invention a complement inhibitor is administered locally to a subject suffering from traumatic brain injury, stroke, or spinal cord injury without also administering a complement inhibitor systemically. Without wishing to be bound by any theory, local administration may augment or exceed beneficial effects, if any, that would result from systemic complement inhibition in a subject suffering from traumatic brain injury, stroke, or spinal cord injury. Local administration may have reduced side effects and enable a higher concentration of inhibitor to be delivered to a location in the CNS where complement activation would result in damage to CNS tissue. Furthermore, local administration will inhibit locally produced soluble complement proteins even after systemic complement proteins and systemically delivered complement inhibitors that are too large to cross the blood-brain barrier, can no longer gain access to the CNS, e.g., after healing has begun. In certain embodiments a neuroprotective or neurotropic agent is also administered systemically and/or locally in various embodiments of the invention. In certain embodiments the neuroprotective or neurotropic agent is administered together with the complement inhibitor in a single composition. Such agents include a variety of peptides and small molecules. The agent may be one that protects against glutamate and/or β-amyloid toxicity. The agent may be one that has been previously shown to be effective in an animal model. The agent may be a second-generation N-methyl-D-aspartic acid or alpha-amino-3-hydroxy-methyl-4-isoxazolyl-propionic acid receptor antagonists, calpain inhibitors, cyclosporine A analog, etc. (Wang, et al., *Curr Opin Neurol.*, 19(6):514-519, 2006). In certain embodiments the agent is thyrotropin-releasing hormone (TRH), a TRH analog, a diketopiperazine structurally related to the TRH metabolite cyclo-his-pro, or a recently described cyclic dipeptide (Faden, et al., *Neuropharmacology*, 49(3):410-24, 2005).

For delivery to the PNS, e.g., in the case of PNS injury or chronic pain mediated at least in part by the PNS, suitable methods include injection or infiltration into a nerve or nerve trunk, e.g., adjacent to a site of nerve damage, and implantation of a polymer-based delivery device or microchip at or adjacent to a site of nerve damage. Methods for administering agents such as anesthetics to diverse nerves, nerve bundles, etc., within the PNS are well known in the art, and any of these methods are applicable in the context of the present invention.

The invention provides compositions comprising a complement inhibitor for administration by inhalation, e.g., through the nose or mouth and into the respiratory tract. In certain embodiments the complement inhibitor is administered in an amount effective to treat a condition that affects the respiratory system, while resulting in minimal absorption into the blood and thus minimal systemic delivery of the complement inhibitor. In certain embodiments of the invention the extent of absorption into the blood is such that no clinically significant complement inhibition is observed in an organ or tissue outside the respiratory system when the complement inhibitor is administered at a dose that is effective in the lung.

The composition can be delivered in the form of an aerosol spray from a pressured container or dispenser which contains a suitable propellant, e.g., hydrofluoroalkanes (HFA): either HFA 134a (1,1,1,2,-tetrafluoroethane) or HFA 227 (1,1,1,2,3,3,3-heptafluoropropane) or combinations of the two are of use, or from a nebulizer. Devices for delivery of aerosolized or non-aerosolized formulations useful for delivering complement inhibitors to the respiratory tract include, but are not limited to, pressurized metered dose inhalers (MDI), dry powder inhalers (DPI), and metered solution devices (MSI), and nebulizers. In certain embodiments the delivery system is suitable for delivering the composition into major airways (trachea and bronchi) of a subject and/or deeper into the lung (bronchioles and/or alveoli). In certain embodiments compositions comprising a complement inhibitor are delivered using a nasal spray.

In certain embodiments the complement inhibitor is delivered to the respiratory tract, e.g., bronchi and/or lungs as a composition that consists essentially of the complement inhibitor in dry, e.g., lyophilized form or in an aqueous medium that consists essentially of water, optionally also including a salt (e.g., NaCl, a phosphate salt), buffer, and/or an alcohol. In other embodiments the composition contains one or more additional components. For example, in certain embodiments the particles contain one or more components in addition to a complement inhibitor.

Aerosol formulations for delivery to the respiratory tract may comprise liquid or dry particles of various dimensions and properties. In certain embodiments of the invention the particles are in the form of a dry composition suitable for inhalation. A dry particle composition containing particles smaller than about 1 mm in diameter is also referred to herein as a dry powder. A "dry" composition has a relatively low liquid content, so that the particles are readily dispersible, e.g., in a dry powder inhalation device to form an aerosol or spray. A "powder" consists largely or essentially entirely of finely dispersed solid particles that are relatively free flowing and capable of being readily dispersed in an inhalation device and subsequently inhaled by a subject, preferably so that a significant fraction of the particles can reach a desired portion of the respiratory tract.

Powder compositions may be characterized on the basis of various parameters such as the fine particle fraction (FPF), the emitted dose, the average particle density, and the mass median aerodynamic diameter (MMAD). Suitable methods are known in the art, some of which are described in U.S. Pat. Nos. 6,942,868 and 7,048,908 and U.S. Publication Nos. 20020146373, 20030012742, and 20040092470. In certain embodiments of the invention particles having a mass mean aerodynamic diameter of between 1 μm and 25 μm, e.g., between 1 μm and 10 μm, are used. In certain embodiments large porous particles having mean geometric diameters ranging between 3 and 15 μm and tap density between 0.04 and 0.6 g/cm$^3$ are used. See, e.g., U.S. Pat. No. 7,048,908; Edwards, D. et al, Science 276:1868-1871, 1997; and Vanbever, R., et al., Pharmaceutical Res. 16:1735-1742, 1999).

Methods for making particles, including dry powders, are described above. The particles may consist essentially of one or more complement inhibitors. In certain embodiments the particles or the composition include one or more additional agents, e.g., stabilizing agents, delivery-enhancing agent, excipients, etc. Suitable excipients for pulmonary delivery are known in the art. See, e.g., U.S. Pat. Pub. No. 20040092470 for exemplary dry powder compositions. These particles while described as useful for oligonucleotide delivery could also be used for delivering other molecules. Dry particle compositions may be delivered in dry form or may be dissolved in a suitable solvent and delivered as liquid aerosols or by other suitable delivery means. Liquid particles can also be delivered, e.g., as aerosol formulations. In general, size ranges for such particles may be similar to those described above for dry particles. In certain embodiments the liquid particles are between approximately 0.5-5 μm for respiratory delivery, though smaller or larger particles could also be used. Suitable aqueous vehicles include water or saline, optionally including an alcohol. In some embodiments the composition comprises a surfactant suitable for introduction into the lung. Additional considerations for pulmonary delivery are discussed in Bisgaard, H., et al., (eds.), Drug Delivery to the Lung, Vol. 26 in "Lung Biology in Health and Disease", Marcel Dekker, New York, 2002.

For topical applications, the complement inhibitor and optionally other therapeutic agent may be formulated in a suitable ointment containing the active agent(s) suspended or dissolved in one or more carriers. Alternatively, the therapeutic agents can be formulated in a suitable lotion, cream, gel, or jelly containing the active components suspended or dissolved in one or more pharmaceutically acceptable carriers. Pastes, suspensions, emulsions, sprays, patches (e.g., hydrogel patches), masks, and powders are other forms suitable for topical administration. Suitable carriers include, but are not limited to, liquid petrolatum, white petrolatum, propylene glycol, polyoxyethylene, polyoxypropylene, emulsifying wax, mineral or other oil, sorbitan monostearate, polysorbate 60, cetyl esters, wax, cetearyl alcohol, 2-octyldodecanol, benzyl alcohol and water. Any methods and materials suitable for preparing ointments, salves, gels, creams, etc., as generally known in the art may be used.

In certain embodiments a formulation intended for topical administration to the skin comprises a skin penetration enhancer. The enhancer may increase effective transport of the agent into or through one or more layers of the epidermis or the dermis. A variety of delivery agents and approaches that enhance uptake and/or penetration of active agents into the skin are of use. In certain embodiments the delivery agent enhances penetration of the stratum corneum. Exemplary compounds include alpha-hydroxy acids, limonene, azone (AZ), lauryl alcohol (LA), other alcohols, isopropyl myristate (IPM), etc.

If desired, the appropriate proportions of therapeutic agent, polymer, and/or any other modifiers for a sustained release formulation such as a population of microparticles or an implant to provide a desired rate of release of the therapeutic agent may be empirically determined by formulating several compositions, for example, with varying proportions of such ingredients. A USP approved method for dissolution or release test can be used to measure the rate of release (USP 23; NF 18 (1995) pp. 1790-1798).

As noted above, the complement inhibitor may be dissolved in a pharmaceutically acceptable carrier prior to its formulation with a drug delivery regulating component. The term "pharmaceutically acceptable carrier" refers to a non-toxic carrier that does not destroy the pharmacological activity of the compound with which it is formulated. Pharmaceutically acceptable carriers or vehicles that may be used in the compositions of this invention include, but are not limited to, water, physiological saline, and the like. As further noted above, pharmaceutically acceptable salts of the compounds can be used, such as those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Salts derived from appropriate bases include alkali metal (e.g., sodium and potassium), alkaline earth metal (e.g., magnesium), ammonium and $N^+(C1-4\ alkyl)4$ salts. This invention also envisions the quaternization of any basic nitrogen-containing groups of the compounds disclosed herein. Water or oil-soluble or dispersible products may be obtained by such quaternization. Furthermore it will be appreciated that the invention encompasses solvates, hydrates, enantiomeric forms, conformers, tautomers, polymorphic forms, etc., of the active agents described herein.

The amount and concentration of the therapeutic agent(s) in a composition can vary depending on a number of factors including, but not limited to, the identity of the therapeutic agent(s), the condition being treated and its severity, the particular gel-forming components and/or chemical cross-linking agents in the composition, the total amount of composition administered (which itself can vary based on various considerations such as the anatomy of the patient, etc.). Exemplary doses are between approximately 0.1 and 10,000 mg/dose for each location to be treated, e.g., between approximately 0.5 and 5000 mg/dose, between 1 and 1000 mg/dose, etc. Exemplary concentrations of a therapeutic agent in a composition of the invention are between approximately 0.001 and 100 mg of the therapeutic agent per milliliter of solution, e.g., the concentration may be between 0.01 and 50 mg/ml, between 0.1 and 10 mg/ml, etc.

The dosing interval (i.e., the time between individual administrations of an inventive composition) and the dose of the therapeutic agent delivered with each administration can vary. In certain embodiments the composition is delivered at times more than 6 weeks apart, e.g., 2, 3, 4, 5, or 6 months apart, or any intervening number of weeks, e.g., 8, 10, 12, 14, 16 weeks, etc. In other embodiments the composition is delivered at even greater time intervals, e.g., at times 7, 8, 9, 10, 11, or 12 months apart. In other embodiments the time interval is 6 weeks or less, e.g., 1, 2, 3, 4, 5, or 6 weeks apart. For example, the composition may be administered on average every 2 weeks, every 4 weeks, every 30 days, etc. Of course the time interval can vary. For example, the time intervals between doses can alternate between 6 weeks or less and more than 6 weeks. In certain embodiments the average time interval between administrations of an inventive composition is at least 6 weeks, e.g., 2, 3, 4, 5, or 6 months, or any intervening number of weeks, e.g., 8, 10, 12, 14, 16 weeks, etc. In certain embodiments of the invention the composition is administered multiple times at time intervals on average at least 6, 8, 10, or 12 weeks apart, or on average 3, 4, 6, 8, 12, 15, 18, or 24 months apart, etc. The composition may be administered at least 1, 2, 5, 10, 15, 20, or more times. The composition may be administered indefinitely at various intervals to a subject suffering from or at risk of a complement-mediated disorder.

Measuring Complement Inhibition

Any suitable method can be used for assessing the ability of an agent or composition containing the agent to inhibit complement activation (or any other relevant properties). A number of in vitro assays can be used. For example, ability of an agent to inhibit the classical or alternative complement pathway may be assessed by measuring complement-mediated hemolysis of erythrocytes (e.g., antibody-sensitized or unsensitized rabbit or sheep erythrocytes), by human serum or a set of complement components in the presence or absence of the agent. An agent inhibits complement if it decreases hemolysis in this inhibition assay to a statistically significant degree ($p<0.05$). The ability of an agent to bind to one or more complement component such as C3, C5, factor B, factor D can be assessed using isothermal titration calorimetry or other methods suitable for performing in liquid phase. In another embodiment, the ability of an agent to bind to a complement component is measured using an ELISA assay. For example, the wells of a microtiter plate are coated with the agent. A complement inhibitor can be functionalized in order to facilitate binding it to a plate. For example, the agent could be biotinylated, and a streptavidin-coated plate is used. Complement component(s) are added to the wells. After a period of incubation the wells are washed, and bound complement components are detected using antibodies to the complement component of interest. Other methods of use include surface plasmon resonance, equilibrium dialysis, etc.

The ability of certain agents such as a VCCP to act as a cofactor for factor I mediated cleavage of a complement component, e.g., C3, C3b, etc., and the rate of such cleavage, may be determined by incubating the agent with the complement component and factor I for a period of time. Following incubation samples are subjected to electrophoresis to separate the components and cleavage products by size. Complement components and cleavage products thereof may be visualized using, for example, Coomassie staining, immunoblotting using antibodies that recognize the component, etc. A time course may be performed. The ability of an agent to bind heparin may be assessed by ELISA assay or by flowing the agent through a heparin column and collecting and analyzing unbound material for presence of the agent (where a diminished amount of the agent indicates that the agent has bound to heparin in the column). Methods for assessing the ability of an agent to bind to cells, e.g., endothelial cells, include flow cytometry. Chemotaxis inhibition by an agent or cellular uptake of an agent can be measured using well established chemotaxis or uptake assays. In any of the above methods, the agent may be tested at a range of different dilutions.

Methods for measuring systemic or local complement activation taking place in vitro or in vivo and for determining the ability of a complement inhibitor to inhibit such activation are known in the art. For example, measurement of complement activation products such as C3a, C5a, C3bBb, C5b-9, covalent complexes between the recognition molecule of the classical pathway (C1q) and activated C4, etc., provides an indication of the extent of complement activation. A decrease in the amount of such products indicates inhibition of complement activation. In some embodiments a ratio between an active cleavage product and its inactive desArg form is measured (e.g., C3a/C3adesArg). One of skill in the art can distinguish between classical, alternative, and lectin pathway activation by appropriate selection of the complement activation product(s) measured and/or appropriate activators of complement such as zymosan, lipopolysaccharide, immune complexes, etc. Other methods involve measuring complement-mediated hemolysis of red blood cells as a result of terminal complex formation.

Complement activation in vivo and/or its inhibition by a complement inhibitor, can be measured in an appropriate biological sample. For example, systemic complement activation and/or its inhibition by a complement inhibitor, can be measured in a blood sample. Local activation and/or inhibition in the respiratory tract can be measured in a sputum sample. Local activation and/or inhibition in a joint can be measured in a sample of synovial fluid. Local activation and/or inhibition in the CNS can be measured in a sample of CSF. Serial measurements beginning before administration of a complement inhibitor provide an indication of the extent to which the complement inhibitor inhibits complement activation and the time course and duration of the inhibition. It will be appreciated that a decrease in activation products may only become apparent once activation products present prior to administration of the complement inhibitor have been degraded or cleared.

The in vivo effects of certain complement inhibitors on systemic or local complement activation in a subject (e.g., a subject suffering from or at risk of a complement-mediated disorder) can also be assessed using in vitro assays such as those described herein or known in the art. Appropriate biological samples (e.g., plasma, synovial fluid, sputum) are obtained from the subject, e.g. prior to and following local administration of a complement inhibitor. The in vitro assay is performed using these samples as a source of complement components. Serial measurements beginning before administration of a complement inhibitor provide an indication of the extent to which the complement inhibitor inhibits complement activation and the time course and duration of the inhibition.

The foregoing methods are described in a number of references cited herein (U.S. Pat. Nos. 5,157,110; 6,551,595; U.S. Pat. No. 6,319,897; WO2004/026328 (PCT/US2003/029653), U.S. Ser. No. 10/937,912; Morikis, 2004; Mallik, 2005; Katragadda, M., 2006,) Sahu, 1998; Smith, 2000; Rosengard, 2002, etc.). Any of these methods or variants thereof, or others known in the art, can be used to assess the effect of systemic and/or local administration of a composition comprising a complement inhibitor in accordance with the present invention. Examples 5 and 6 provide suitable assays to measure inhibition of the classical and alternative pathways, respectively.

Monitoring Degradation of a Sustained Release Formulation or Device

Certain sustained release formulations and devices release a therapeutic agent as the material degrades under physiological conditions. Bioavailability of the agent and/or amount or concentration of the agent at a site of desired activity is typically at least in part controlled by the rate at which the mass and/or volume of the material decreases. The invention provides methods of monitoring a sustained release formulation or device comprising a therapeutic agent. The methods are of use to monitor degradation of a biodegradable sustained release formulation or device. The methods are of use to monitor bioavailability of the agent and/or amount or concentration of the agent at a site of desired activity. The invention provides a sustained release formulation or device comprising a detectable moiety and a therapeutic agent such as a complement inhibitor or any other therapeutic agent discussed herein. As used herein a "detectable moiety" is a moiety, e.g., molecule or supramolecular complex, which can be included in a sustained release formulation and can be detected by a particular method or methods of interest. Typically the detection method is external and non-invasive, i.e., the method does not involve penetration of the skin or another externally accessible body surface or entry into a body cavity. In certain embodiments the detectable moiety has a property that renders it detectable without the need to administer another moiety to render the detectable moiety detectable. In certain embodiments of the invention the detectable moiety can be detected while present in the sustained release formulation or device. In certain embodiments the detectable moiety can be detected only when it is no longer present in the sustained release formulation or device. In certain embodiments of the invention the detectable moiety cannot be detected after it has been released from the sustained release formulation or device or is detectable for only a limited period of time (e.g., up to 1-2 weeks). For example, the detectable moiety may degrade or be cleared from its site of release.

In certain embodiments, detection of the detectable moiety can be used to assess the mass or volume of the sustained release formulation or device that remains intact at a time "X" after administration and/or to assess the mass or volume of the sustained release formulation or device that has degraded at a time "X" after administration. If it is determined that a predetermined mass or volume of the formulation has degraded or remains, the subject may be retreated within a suitable time period. For example, retreatment can be scheduled to take place within 1, 2, 3, or 4 weeks of the time when the formulation is determined or expected to be at least 70%, 80%, 90%, 95%, 99% or 100% degraded. Detection of the detectable moiety can alternately or additionally be used to assess the amount of therapeutic agent that remains within the sustained release formulation or device, i.e., has not yet been released.

In certain embodiments the detectable moiety is selected to be released from the sustained release formulation or device, or to degrade, at a rate that correlates with the rate of release of the therapeutic agent, e.g., at about the same rate. Detection of the detectable moiety can thus be used to determine the amount of the therapeutic agent that has been released or, equivalently, the amount that has not been released.

Thus the invention provides a method of treating a subject comprising: (a) administering to the subject a first quantity of a first biodegradable sustained release formulation or device comprising a detectable moiety and a therapeutic agent; (b) detecting the detectable moiety using a non-invasive detection method. In certain embodiments, presence and/or amount of the moiety detected serves as an indication of the amount of the sustained release formulation or device that remains intact or has degraded or serves as an indication of the amount of the therapeutic agent remaining in the sustained release formulation or device. In certain embodiments the moiety is detected to facilitate appropriate placement of the formulation or device at an extravascular location in the body. The method may further comprise (c) administering to the subject a second quantity of a second sustained release formulation or device based on the results of step (b). The first and second amounts may be the same or different. The first and second sustained release formulations may be the same or different. If different, they may differ in the amount or identity of (i) the therapeutic agent; or (ii) a drug delivery regulating component such as a polymer matrix. Steps (b) and (c) can be repeated multiple times. Step (b) could comprise determining that the moiety is undetectable or is present in an amount below a predetermined level, wherein failure to detect the moiety, or detection below a predetermined level indicates that the sustained release formulation or device remains at least partially intact or, in certain embodiments, has substantially degraded.

The sustained release formulation or device could be any sustained release formulations or device described herein or known in the art. It could be in the form of a gel, solid or semi-solid macroscopic or microscopic article of manufacture, plurality of microparticles or nanoparticles, etc. In one embodiment, the detectable moiety is distributed uniformly throughout the formulation, e.g., its concentration varies by not more than about 20% throughout the formulation. The structure could be, e.g., a macroscopic implant, microparticle, or nanoparticle. In certain embodiments the shape and/or size of the structure can be monitored by detecting the moiety. In certain embodiments, as the structure degrades, the moiety is released such that eventually the total signal detected from the remaining portion of the structure is below a predetermined threshold, indicating that the sustained release formulation or device has largely degraded. In certain embodiments the moiety becomes detectable following its release as the structure degrades, such that eventually the signal is above a predetermined threshold, indicating that the sustained release formulation or device has largely degraded. In certain embodiments, such an approach is used for a formulation that is administered as a liquid and forms a gel following administration. The detectable moiety is mixed in solution with the gel-forming material and the therapeutic agent. At least a portion of the detectable moiety (e.g., at least 10, 20, 30, 40, 50, 60, 70, 80, 90% or more of the detectable moiety is trapped within the gel following administration.

In other embodiments the detectable moiety is non-uniformly distributed in the formulation. For example, the detectable moiety may be concentrated in a central region of the formulation that is expected to remain intact when most of the formulation has degraded. Detection of the moiety indicates that most of the formulation has degraded and released the therapeutic agent. The detectable moiety could become detectable as the thickness of the outer layer decreases and/or as the detectable moiety is released.

A variety of different detectable moieties could be incorporated into a sustained release formulation or device. In certain embodiments the detectable moiety is substantially non-toxic when administered in the amounts and at the sites envisioned for administration of the sustained release formulation or device. In certain embodiments the detectable moiety is a particle. In certain embodiments the detectable moiety is not a particle. In certain embodiments the detectable moiety is soluble in an aqueous medium or organic solvent. The detectable moiety may be or comprise a fluorescent or luminescent molecule. The molecule may be a protein or an organic or inorganic dye. In certain embodiments the detectable moiety is a quantum dot. In certain embodiments of the invention the detectable moiety emits a detectable signal, e.g., electromagnetic energy such as in the form of UV, visible, or infrared light. In certain embodiments the detectable moiety detectably absorbs electromagnetic radiation. In certain embodiments the detectable moiety is not a therapeutic agent. In certain embodiments the detectable moiety is not an amino acid, nucleotide, or nucleic acid. In certain embodiments the detectable moiety is distinct from the drug releasing component of a sustained release formulation or device. One aspect of the present invention is a composition comprising a complement inhibitor (e.g., a compstatin analog) and a detectable moiety, e.g., a detectable moiety described herein.

Fluorescence is a phenomenon in which absorption of light of a given wavelength by a fluorescent molecule is followed by the emission of light at longer wavelengths. See, e.g., Valeur, B., "Molecular Fluorescence: Principles and Applications", John Wiley and Sons (2002), "Handbook of Fluorescent Probes and Research Products" (Molecular Probes, 9th edition, 2002) and "The Handbook—A Guide to Fluorescent Probes and Labeling Technologies", (Invitrogen Corp., 10th edition, available at the Invitrogen web site and from Invitrogen Corp.). Chemiluminescence is the emission of light from a chemical reaction that occurs at or near ambient temperatures. Bioluminescence is a luminescent process mediated by an enzyme or other biological system. See, e.g., McCapra and Beheshti in "Bioluminescence and Chemiluminescence: Instruments and Applications", K. Van Dyke (ed.), CRC Press, Boca Raton, Fla., pgs. 9-42 (1985).

Fluorescent and luminescent molecules include a variety of different organic or inorganic small molecules commonly referred to as "dyes" or "indicators". Fluorescent and luminescent molecules also include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins (RFP, BFP, YFP, CYP, and SFP), reef coral fluorescent protein, etc. Luminescent proteins include luciferase, aequorin and derivatives thereof. Numerous fluorescent and luminescent dyes and proteins are described in the handbooks from Molecular Probes and Invitrogen mentioned above. Exemplary molecules include fluorescein, rhodamine, tetramethylrhodamine, R-phycoerythrin, Cy-3, Cy-5, Cy-7, Texas Red, Phar-Red, allophycocyanin (APC), fluorescein amine, eosin, dansyl, umbelliferone, 5-carboxyfluorescein (FAM), 2'7'-dimethoxy-4'5'-dichloro-6-carboxyfluorescein (JOE), 6 carboxyrhodamine (R6G), N,N,N',N'-tetramethyl-6-carboxyrhodamine (TAMRA), 6-carboxy-X-rhodamine (ROX), 4-(4'-dimethylaminophenylazo)benzoic acid (DABCYL), 5-(2'-aminoethyl)aminonaphthalene-1-sulfonic acid (EDANS), 4-acetamido-4'-isothiocyanatostilbene-2,2' disulfonic acid, acridine, acridine isothiocyanate, r-amino-N-(3-vinylsulfonyl)phenylnaphthalimide-3,5, disulfonate (Lucifer Yellow VS), N-(4-anilino-1-naphthyl)maleimide, anthranilamide, Brilliant Yellow, coumarin, 7-amino-4-methylcoumarin, 7-amino-4-trifluoromethylcouluarin (Coumarin 151), cyanosine, 4',6-diaminidino-2-phenylindole (DAPI), 5',5"-diaminidino-2-phenylindole (DAPI), 5',5"-dibromopyrogallol-sulfonephthalein (Bromopyrogallol Red), 7-diethylamino-3-(4'-isothiocyanatophenyl)-4-methylcoumarin diethylenetriamine pentaacetate, 4,4'-diisothiocyanatodihydro-stilbene-2,2'-disulfonic acid, 4,4'-diisothiocyanatostilbene-2,2'-disulfonic acid, 4-dimethylaminophenylazophenyl-4'-isothiocyanate (DABITC), eosin isothiocyanate, erythrosin B, erythrosin isothiocyanate, ethidium, 5-(4,6- dichlorotriazin-2-yl)aminofluorescein (DTAF), QFITC (XRITC), fluorescamine, IR144, IR1446, Malachite Green isothiocyanate, 4-methylumbelliferone, ortho cresolphthalein, nitrotyrosine, pararosaniline, Phenol Red, B-phycoerythrin, o-phthaldialdehyde, pyrene, pyrene butyrate, succinimidyl 1-pyrene butyrate, Reactive Red 4 (Cibacron® Brilliant Red 3B-A), lissamine rhodamine B sulfonyl chloride, rhodamine B, rhodamine 123, rhodamine X, sulforhodamine B, sulforhodamine 101, sulfonyl chloride derivative of sulforhodamine 101, tetramethyl rhodamine, riboflavin, rosolic acid, and terbium chelate derivatives).

Other detectable moieties include electron spin resonance molecule (such as for example nitroxyl radicals), electrical charge transducing or transferring molecules, etc.

Quantum dots (QDs) are nanocrystals with physical dimensions small enough (e.g., smaller than the exciton Bohr radius) such that the effect of quantum confinement gives rise to unique optical and electronic properties that are not observed either in the bulk material, in discrete atoms, or in larger nanoparticles. Semiconductor QDs are often composed of atoms from groups II-VI or III-V in the periodic table, but other compositions are also possible. Quantum dots generally have a broad absorption spectrum and a narrow emission spectrum. By varying their size and composition, the emission wavelength can be tuned (i.e., adjusted in a predictable and controllable manner) from the blue to the near infrared. Quantum dots and methods for their synthesis and conjugation with biomolecules are well known in the art (See, e.g., Michalet X, et al., *Science,* 307(5709):538-44, 2005; Smith, A M, *Ann Biomed Eng.,* 34(1):3-14, 2006). Quantum dots with a large variety of absorption and emission spectra are commercially available, e.g., from Evident Technologies (Troy, N.Y.) or Quantum Dot Corp. (Hayward Calif.; now owned by Invitrogen), etc. Quantum dots are described, e.g., in U.S. Pat. Nos. 5,990,479; 6,207,392 6,251,303; and 6,914,265, among others. In some embodiments the QDs are soluble. In some embodiments the QDs are coated with a polymer or other material, e.g., one or more hydrophilic or amphipathic polymers, that increases the stability of the QDs, renders the QDs soluble, and/or renders the QDs biocompatible. The polymer may stabilize the QDs in a physiological environment. In some embodiments the QDs are stable while contained in the sustained release formulation but unstable when released from the formulation or device into the local environment within the body. In this case, detection of the QDs implies that the QDs are still contained in the sustained release formulation or device and provides an indication of the extent to which the formulation or device remains intact. In some embodiments the QDs are incorporated into particles (e.g., composed of a biocompatible polymer matrix) which are themselves incorporated into the sustained release formulation or device. See Vashist, et al., "Review of Quantum Dot Technologies for Cancer Detection and Treatment", AZojono Journal of Nanotechnology Online, posted Sep. 13, 2006; DOI: 10.2240/azojono0113 and references therein for additional information about QDs of use in the present invention.

Also of use are detectable moieties that increase the detectability of the sustained release formulation or device by ultrasound or magnetic resonance. Such moieties are referred to in the art as contrast enhancers or agents. Ultrasound contrast enhancers known in the art are of use. In one embodiment the detectable moiety comprises gas-filled microbubbles. Also of use are magnetic resonance contrast enhancers known in the art. Also of use are radioactive or radioopaque moieties known to those of skill in the art as suitable administration to mammalian subjects over time periods contemplated herein.

In certain embodiments the detectable moiety is not perceived by the subject when administered to the eye in amounts sufficient to allow its external detection in accordance with the invention. In this regard, moieties that do not emit significant amounts of electromagnetic radiation within the visible portion of the electromagnetic spectrum may be preferred.

The detection method will be selected as appropriate to detect the detectable moiety. For example, in certain embodiments the detection method detects electromagnetic radiation within the infrared, near-infrared, visible, or UV portion of the spectrum. Suitable detection systems are known in the art and may employ, for example, charge coupled devices (CCDs), CMOS sensors, LEDs, etc. For example, one of skill in the art could employ a detection system known in the art for in vivo imaging of QDs. In certain embodiments detection employs an optical coherence tomography (OCT) system. The invention provides a medical instrument, e.g., an opthalmoscope, comprising a detection system capable of detecting fluorescent or luminescent moieties in an extravascular location in the body. In certain embodiments the instrument is an opthalmoscope, and the extravascular location is the eye, or a compartment thereof, e.g., the vitreous chamber. In one embodiment, the invention provides an opthalmoscope comprising a detection system capable of detecting QDs in the eye, e.g., within the vitreous chamber. In certain embodiments the instrument enables visualization of the distribution of the detectable moiety within the extravascular location, e.g., within the eye. In certain embodiments the detector enables quantification of the amount or distribution of the detectable moiety in the extravascular location. In certain embodiments the instrument comprises a portable, e.g., handheld, portion or probe comprising a detector, or comprises an optical fiber that transmits a signal to a detector. In one embodiment the instrument comprises a miniaturized fluorescence imaging system such as the LumiSens 830 (Sensovation Corp., Pleasanton, Calif. 94588). As used herein, "portable" means in certain embodiments that the instrument or portion thereof referred to weighs about 5 kg or less, e.g., about 2 kg or less, e.g., about 1 or 0.5 kg, or less, and is typically movable from room to room by an adult person of average strength without needing to be on wheels or in contact with a weight-bearing surface such as a floor. As used herein, "handheld" means that the instrument or portion thereof referred to can be readily manipulated and positioned for use by hand by an adult person of average strength. In certain embodiments the instrument comprises magnification means, e.g., a microscope or other lens system and/or comprises a camera. In certain embodiments the instrument comprises an ultrasound transducer. In certain embodiments the instrument comprises or interfaces with a signal processor. In certain embodiments the instrument interfaces with a computer and/or a display device so that, e.g., the user can visualize the sustained release formulation within the body, e.g., within the vitreous chamber. The invention thus provides a variety of systems comprising a detection means and any one or more of the afore-mentioned components.

The invention provides a sustained release formulation or device comprising a detectable moiety and a complement inhibitor. In certain embodiments the complement inhibitor is a compstatin analog.

Therapies for Ocular Disorders

Another aspect of the present invention relates to treatment of ocular disorders characterized by macular degeneration and/or ocular inflammation using any of a variety of different agents. Such disorders include age-related macular degeneration, diabetic retinopathy, uveitis, and glaucoma.

In certain embodiments the therapeutic agent is an anti-TNF agent, e.g., an anti-TNFα agent. The term "anti-TNF agent" refers to an agent that antagonizes, neutralizes, opposes, and/or inhibits the activity of TNF, e.g., TNFα, TNFβ, or both. In certain embodiments the anti-TNF agent comprises a TNF receptor that binds to TNF and renders it biologically unavailable. The term "TNF receptor" refers to a full length TNF receptor or a portion thereof sufficient to bind to TNF (e.g., TNFα). TNF binds to p55 (also termed TNF-R55, TNF-RI, or TNFRβ) and p75 (also termed TNF-R75, TNF-RII, or TNFRα) TNF receptors. TNF receptors exist both on the cell surface and as soluble receptors. The soluble forms are involved in the regulation and bioavailability of TNF (Locksley R M, et al., *Cell,* 104:487-501, 2001). In certain embodiments of the invention the anti-TNF agent is a soluble TNFα receptor. The TNFα receptor may comprise the extracellular domain of a naturally occurring TNFα receptor such as p55 or p75 receptor, or a portion thereof sufficient to bind TNFα. See, e.g., U.S. Pat. Nos. 5,395,760; 5,605,690; 5,945,397; 6,201,105; 6,572,852; Re. 36,755. The anti-TNFα agent may comprise two or more soluble TNFα receptors or portions thereof attached together, e.g., by a peptide or non-peptide linker, as a fusion protein, etc. For example, the agent may be a dimer containing two soluble TNF receptors. The soluble TNFα receptor may comprise at least a portion of the sequence of a human TNFα receptor, e.g., at least a portion of the extracellular domain. The agent may further comprise one or more additional polypeptide domains, e.g., a portion of an antibody molecule such as an Fc domain or portion thereof. In certain embodiments the therapeutic agent is etanercept (Enbrel®). In certain embodiments the TNF receptor comprises a recombinantly produced polypeptide.

In certain embodiments the anti-TNF agent comprises an antibody or peptide that specifically binds to TNF, e.g., specifically binds to TNFα. The peptides can be, e.g., portions of a TNFα receptor and/or portions or structural analogs of anti-TNFα antibody antigen binding regions or variable regions. Such antibodies or peptides bind TNF with neutralizing and/or inhibiting biological activity. In certain embodiments the therapeutic agent is a monoclonal antibody such as infliximab (Remicade®). The antibody may be a mouse antibody, chimeric antibody, humanized antibody, etc. For example, the antibody may comprise human constant and non-human (e.g., rodent such as murine) variable regions. See, e.g., U.S. Pat. No. 5,656,272, for discussion of a variety of anti-TNF agents of use in various embodiments of the invention. See also U.S. Pat. Nos. 5,641,751; 5,698,195; 5,919,452; 6,277,969; 6,284,471; or 6,835,823. In certain embodiments the antibody is a human monoclonal antibody such as adalimumab (Humira®) (see PCT publication WO97/29131). In certain embodiments the anti-TNF agent is approved for use by the Food and Drug Administration (FDA) and/or by one or more other agencies or bodies that regulates the approval of pharmaceutical agents for use in humans. The agent can be administered using any suitable method. In certain embodiments the agent is locally administered to the eye or in the vicinity of the eye. The agent may be administered, e.g., by intravitreal injection, sub-Tenon injection, retrobulbar injection, subretinal injection, subconjunctival injection, suprachoroidal injection, or intrascleral injection. The agent can be formulated using any available sustained release formulation or device suitable for delivering therapeutic agents to the eye. A sustained release formulation or device described herein or otherwise known in the art can be used. In certain embodiments the agent is administered in an implant suitably dimensioned for administration to the eye. In certain embodiments the formulation comprises microparticles or nanoparticles or a gel-forming material.

In certain embodiments the amount of the anti-TNF agent administered is approximately the amount needed to inhibit TNF activity in the eye by at least 50%, 60%, 70%, 80%, 90%, or more. In certain embodiments the amount of the anti-TNF agent administered to the eye is approximately the amount needed to reduce TNF activity in the eye to no more than 10%, 20%, 30%, 40%, or 50% of its activity in the absence of the agent. The TNF activity inhibited may be any biological activity of TNF. In certain embodiments the amount of the anti-TNF agent administered to the eye is approximately the amount needed to bind to at least 50%, 60%, 70%, 80%, 90%, or more of the TNF molecules present in a compartment of the eye such as the vitreous. In certain embodiments the amount or concentration of the anti-TNF agent administered to the subject is approximately the same as, or no more than 2 times the maximum dose approved by the FDA or another regulatory agency for systemic administration of the agent. In certain embodiments the amount or concentration of the anti-TNF agent locally administered to the eye of the subject or present within the eye following administration of a sustained release formulation comprising the agent, is approximately the same as, or no more than the maximum dose approved by the FDA or another regulatory agency for systemic administration of the agent. In certain embodiments the amount or concentration of the anti-TNF agent administered to the subject is approximately the same as, or no more than 2 times, or no more than 5 times the average effective dose when the agent is systemically administered to treat rheumatoid arthritis. In certain embodiments the amount or concentration of the anti-TNF agent locally administered to the eye of the subject or present within the eye following administration of a sustained release formulation comprising the agent, is approximately the same as, or no more than 2 times, or no more than 5 times the average effective dose when the agent is systemically administered to treat rheumatoid arthritis. In certain embodiments the total amount of the agent administered to the eye in a single dose is between 10 µg and 50 mg. In certain embodiments the total amount of the agent administered to the eye in a single dose is between 100 µg and 5 mg. In certain embodiments the total amount of the agent administered to the eye in a single dose is between 100 µg and 1 mg.

In certain embodiments the subject does not suffer from an inflammatory disorder other than an eye disorder. In certain embodiments the subject does not suffer from one or more disorders selected from the group consisting of: rheumatoid arthritis, psoriatic arthritis, psoriasis, Crohn's disease, ankylosing spondylitis, or another disorder, for which treatment with the anti-TNF agent would be indicated. In certain embodiments the subject does suffer from one or more disorders selected from the group consisting of: rheumatoid arthritis, psoriatic arthritis, psoriasis, Crohn's disease, ankylosing spondylitis, or another disorder, for which treatment with the anti-TNF agent would be indicated, but the subject is treated using a dose, formulation, or route of administration that one of skill in the art would not consider suitable for treating the disorder.

Combination Therapies and Compositions

The present invention contemplates the use of complement inhibitors such as compstatin analogs or mimetics together with one or more other second agents effective for treatment of a disorder discussed herein. The agents may be administered separately or together in the same composition. If administered separately they may be administered concurrently or sequentially. In certain embodiments a complement inhibitor is administered locally and a second agent is administered systemically. In other embodiments two or more agents are administered locally. In certain embodiments two or more agents are administered as components of the same formulation, e.g. the same sustained release formulation. The invention contemplates the addition of a complement inhibitor to existing therapies for various disorders discussed herein, to achieve improved overall efficacy.

The agents may act on the same target(s) or pathway(s) or on different targets or pathways. The complement inhibitor and the second agent may act additively or synergistically (wherein the combined activity of the agents is greater than the sum of their activities if administered individually). In some embodiments presence of the complement inhibitor unexpectedly allows a reduction in the dose of the second agent required to produce a desired effect.

The second agent(s) are selected as appropriate for the disorder to be treated. In some embodiments the agent is already used in the art for treatment of the disorder. In other embodiments the agent is not commonly used in the art for treatment of the disorder. Suitable agents include anti-inflammatory agents such as corticosteroids, non-steroidal anti-inflammatory agents, leukotriene or leukotriene receptor antagonists, cytokine or cytokine receptor antagonists (e.g., anti-TNFα agents such as antibodies or soluble TNFα receptors or fragments thereof that bind TNFα), anti-IgE agents (e.g. antibodies or antibody fragments that bind to IgE or to an IgE receptor), angiogenesis inhibitors, analgesic agents, and anti-infective agents. Anti-infective agents include anti-viral agents, anti-bacterial agents, anti-fungal agents, and anti-parasite agents. Suitable corticosteroids agents of use in various embodiments of the invention include dexamethasone, cortisone, prednisone, hydrocortisone, beclomethasone dipropionate, betamethasone, flunisolide, methylprednisone, paramethasone, prednisolone, triamcinolone, alclometasone, amcinonide, clobetasol, fludrocortisone, diflorasone diacetate, fluocinolone acetonide, fluocinonide, fluorometholone, flurandrenolide, halcinonide, medrysone and mometasone, and pharmaceutically acceptable mixtures and salts thereof and any other derivatives and analogs thereof. Antibiotics such as sulfisoxazole, penicillin G, ampicillin, cephalosporins, quinolones, amikacin, gentamicin, tetracyclines, chloramphenicol, erythromycin, clindamycin, isoniazid, rifampin, and derivatives, salts and mixtures thereof; antifungals such as amphotericin B, nystatin, ketoconazole, itraconazole; and other art known anti-infective or agents or combinations thereof are of use.

In certain embodiments the anti-inflammatory agent is an agonist of a melanocortin receptor. Examples include melanocyte-stimulating hormones (e.g., α-MSH) and fragments, variants, or analogs thereof, such as the core melanocortin peptide His-Phe-Arg-Trp, the melanocortin receptor agonist MTII ([Ac-N1e4, Asp5, d-Phe7, Lys10]cyclo-alpha-MSH-(4-10) amide). In some embodiments the agent is an antagonist of a Toll-like receptor (TLR). The TLR may be any of the TLRs known in mammals, e.g., TLR1-TLR13. In some embodiments the agent is a TLR4 antagonist. In some embodiments the agent is a TLR2 or TLR5 antagonist. In some embodiments the agent is a TLR9 antagonist. In some embodiments the agent is a TLR3 or TLR7 antagonist.

Suitable agents may be selected as appropriate for the disorder being treated. For example, in the case of a disorder affecting a joint, a chondroprotective agent may be used. Such an agent may preserve or stimulate cartilage formation. The agent may stimulate synthesis of extracellular matrix components such as proteoglycans or collagen. In certain embodiment the chondroprotective agent is insulin-like growth factor 1 (IGF-1) or a biologically active fragment or variant thereof. IGF-1 receptor agonists could also be used. In certain embodiments the agent is insulin or an insulin variant. See, e.g., U.S. Pat. No. 6,689,747 for further information regarding insulin and useful formulations containing insulin. The agent may be administered in an amount effective to (a) retain proteoglycans in the matrix, (b) inhibit proteoglycan release from matrix, or (c) stimulate proteoglycan synthesis. In certain embodiments the agents comprise at least one anabolic chondroprotective agent. In certain embodiments the agents comprise at least one anabolic chondroprotective agent and at least one inhibitor of cartilage catabolism, each being included in therapeutically effective amounts such that the plurality of chondroprotective agents both inhibit cartilage catabolism and promote cartilage anabolism. Exemplary anabolic chondroprotective agents are selected from the group consisting of interleukin (IL) agonists that promote cartilage anabolism, members of the transforming growth factor-β superfamily that promote cartilage anabolism, insulin-like growth factors that promote cartilage anabolism and fibroblast growth factors that promote cartilage anabolism. In certain embodiments the anabolic chondroprotective agent is selected from the group consisting of IL-4, IL-10, IL-13, TGF-β1, TGF β2, TGF β3, BMP-2, BMP-4, BMP-6, BMP-7, IGF-1, bFGF and variants thereof that retain the biological characteristics of the naturally occurring agents. In certain embodiments the anabolic chondroprotective agent is selected from the group consisting of: members of the transforming growth factor-β superfamily that promote cartilage anabolism; insulin-like growth factors that promote cartilage anabolism; and fibroblast growth factors that promote cartilage anabolism. In certain embodiments the inhibitor of cartilage catabolism is selected from the group consisting of IL-1 receptor antagonists that inhibit cartilage catabolism, TNF-α receptor antagonists that inhibit cartilage catabolism, cyclooxygenase-2 specific inhibitors that inhibit cartilage catabolism, MAP kinase inhibitors that inhibit cartilage catabolism, nitric oxide synthase inhibitors that inhibit cartilage catabolism, and nuclear factor kappa B inhibitors that inhibit cartilage catabolism. In certain embodiments the inhibitor of cartilage catabolism is selected from the group consisting of: inhibitors of matrix metalloproteinases that inhibit cartilage catabolism; cell adhesion molecules that inhibit cartilage catabolism; intracellular signaling inhibitors that inhibit cartilage catabolism; and inhibitors of SH2 domains that inhibit cartilage catabolism. See U.S. Pat. No. 7,067,144 for additional information regarding these and other suitable agents as well as exemplary doses. In certain embodiments the cartilage catabolism antagonist is selected from the group consisting of: IL-1ra, NO inhibitors, ICE inhibitors, antagonists of IL-6, IL-8, LIF, IFN-γ or TNF-α, tetracyclines and variants thereof, inhibitors of apoptosis, MMP inhibitors, aggrecanase inhibitors and inhibitors of serine and cysteine proteinases. In certain embodiments the agent is a peptide growth factor. The peptide growth factor may be selected from a family member from the group consisting of: IGF (1,2), PDGF (AA, AB, BB), BMPs, FGF (1-20), TGF-β (1-3) and EGF. In certain embodiments the agent is selected from the group consisting of bisphosphonates, and osteoprotegerin. In certain embodiments the agent is an anti-inflammatory agent selected from the group consisting of anti-TNFα antibodies, soluble TNF receptors, IL1ra, soluble IL1 receptors, IL4, IL-10 and IL-13.

In certain embodiments the additional agent is a local anesthetic agent. A "local anesthetic agent" or "local anesthetic" is a drug that provides local numbness and/or analgesia. The term also includes, but is not limited to, any drug which, when locally administered, e.g., topically or by infiltration or injection, provides localized full or partial inhibition of sensory perception and/or motor function. Local anesthetic agents include bupivacaine, ropivacaine, dibucaine, procaine, chloroprocaine, prilocalne, mepivacaine, etidocaine, tetracaine, lidocaine, and xylocaine, as well as anesthetically active derivatives, analogs and mixtures thereof. The local anesthetic can be in the form of a salt, for example, the hydrochloride, bromide, acetate, citrate, carbonate or sulfate. In one embodiment the local anesthetic agent is in the form of a free base. In certain embodiments the local anesthetic agent is a long-acting agent capable of effectively relieving pain for at least as long as bupivacaine when administered in an acceptable dose. Compositions comprising a complement inhibitor and a local anesthetic agent may be locally administered to a joint or bursa, e.g., to a subject suffering from arthritis, ankylosing spondylitis, etc.

In certain embodiments the composition is administered for a disorder affecting the nervous system and the additional agent is a member of the brain-derived neurotrophic factor (BDNF) family or nerve growth factor (NGF) family, e.g., BDNF, NGF, or NT-3. See, e.g., U.S. Pat. Nos. 6,663,899 and 6,933,276 for information regarding certain of these factors and formulations thereof.

It will be appreciated that a number of the agents mentioned herein are found naturally in mammalian subjects. In certain embodiments the administered agent is from the same species as the subject to whom it is administered. For example, human IFG-1 or NGF is administered to a human. In other embodiments the agent is from a different species.

The invention provides a sustained release formulation comprising a complement inhibitor, e.g., a compstatin analog or VCCP, and an additional agent selected from those mentioned above. The invention provides a sustained release formulation comprising a complement inhibitor, e.g., a compstatin analog or VCCP, and two additional agents selected from those mentioned above.

Testing Therapeutic Potential in Animal Models and Humans

A number of different animal models with pathological features that resemble one or more features of a complement-mediated disorder are known in the art. A composition containing a complement inhibitor can be administered in various doses to mice, rats, dogs, primates, etc., that spontaneously exhibit a disorder or in which a disorder has been experimentally induced by subjecting the animal to a suitable protocol. The ability of the compound to prevent or treat one or more signs or symptoms of the disorder is assessed using standard methods and criteria.

Any animal model known in the art can be used to assess the safety and/or efficacy of local administration of a complement inhibitor. In certain embodiments of the invention the animal model is one in which local complement activation occurs at an extravascular location manifesting symptom(s) of the disorder. A suitable animal model may more closely replicate the role of local complement activation in human subjects suffering from the disorder than certain other animal models known in the art. In certain embodiments a suitable animal model is generated by locally administering a sensitizing, irritating, or immunogenic substance to an extravascular location such as a joint, the respiratory tract, the skin, or the CNS. See, e.g., Linton, supra. In certain embodiments a suitable animal model is generated by locally administering a first sensitizing, irritating, or immunogenic substance to an extravascular location such as a joint, the respiratory tract, the skin, or the CNS, and administering a second sensitizing, irritating, or immunogenic substance systemically. The substances could be the same or different and could be administered in either order in various embodiments of the invention. The invention provides a method of testing a candidate agent for treatment of an inflammation-associated disorder, the method comprising steps of: providing an animal in which at least one complement pathway is abnormally activated at an extravascular location at which the disorder is manifest; administering the candidate agent to the extravascular location so that the agent is present for a prolonged period of time at said location in an amount effective to inhibit local complement activation; and determining whether the symptom is significantly alleviated following administration of the candidate agent, wherein if the symptom is significantly alleviated the candidate agent is identified as being of use in treating the disorder by local administration.

Compounds that show promising results in animal studies, such as acceptable safety and feasibility of administering a dose expected to effectively inhibit complement in the relevant extravascular location in a human subject, may be tested in humans, e.g., using standard protocols and endpoints for clinical trials for therapies for the particular disorder under study. It will be appreciated that in the case of certain disorders of interest herein, demonstrating efficacy in animal models is not necessary in order to establish that a compound described herein would be considered therapeutically useful by those of skill in the art and/or for conducting clinical trials in humans although such results could strengthen the motivation for proceeding to clinical trials.

The methods of the invention may include providing a subject to which a composition of the invention is to be administered. The subject is typically at risk of or suffering from a complement-mediated disorder. In certain embodiments the subject is at risk of or suffers from at least one complement-mediated disorder other than an eye disorder characterized by macular degeneration, choroidal neovascularization, retinal neovascularization, or ocular inflammation. In certain embodiments the subject is at risk of or suffers from at least one complement-mediated disorder in addition to an eye disorder characterized by macular degeneration, choroidal neovascularization, retinal neovascularization, or ocular inflammation.

The composition is typically administered to the subject with the intent of treating or preventing development of such disorder. Thus the subject will typically have been identified as being at risk of or suffering from such a condition. Any suitable tests and criteria can be used to identify a subject at risk of or suffering from disorder of interest herein. Methods for diagnosis of the disorders of interest herein and for assessing response to therapy are known in the art.

In certain embodiments of the invention the method of treatment comprises determining whether the subject has a genetic polymorphism that increases the risk of the disorder. "Determining" as used here refers to establishing that a subject has a polymorphism that increases the risk of the disorder, either by performing or ordering a suitable test, or by receiving results of a test performed or ordered by another, wherein the test ascertains whether the subject has the polymorphism. It will be appreciated that a useful genetic test need not be 100% accurate. The polymorphism may be in gene that encodes a complement component.

EXAMPLES

Example 1

ELISA-Based Assay for Classical Complement Pathway Activation to Assess Complement Inhibiting Activity

This example describes a protocol for measuring complement pathway activation and the ability of a test agent, e.g., a complement inhibitor of interest, to inhibit it. The protocol measures C3b deposition in an ELISA format. C3b deposition monitored here is through complement activated by the classical pathway. Briefly, 96-well plates are coated with BSA. Plasma (or any biological sample of interest), chicken ovalbumin (OVA), polyclonal anti-OVA antibodies and a complement inhibitor of interest are then added and incubated, followed by addition of Anti-human C3 HRP-conjugated antibody. After an additional incubation, substrate is added and signal detected.

Ninety-six well ELISA plate (ThermoElectron 9205)
Chicken OVA (Sigma A5378)
Polyclonal anti-chicken OVA (Abcam ab1221-100)
BSA 1% in PBS—Calbiochem #126626 1/30 dilution
Veronal Buffer+0.5 mM $MgCl_2$+0.15 mM $CaCl_2$ ($VB^{++}$)
Plasma (collected with Lepirudin at 5 ug/ml final concentration)
Anti-human C3 HRP-conjugated polyclonal Ab (C3-HRP Ab, Cappel 55237)
Tween-20 Wash Buffer (0.05% in PBS)
TMB (Peroxidase substrate)—1:1 mixture of BD 51-2607KC and 51-2606KC.
3M $H_2SO_4$
Micro-plate Reader Protocol:
1. Add 50 μl/well of 1% chicken OVA (in PBS)
2. Incubate for overnight at 4° C.
3. Remove by shaking and tapping the plate; aspirate any remaining fluid.
4. Block by adding 200 μl of 1% BSA/PBS
5. Incubate for 1 h at room temp
6. Remove by shaking and tapping the plate; aspirate any remaining fluid.
7. Add 50 μl of 1/4000 dilution of Polyclonal anti-chicken OVA in 1% BSA/PBS
8. Incubate for 1 h at room temp
9. Wash twice with wash buffer
10. Add 50 μl $VB^{++}$ to wells #2 to 12
11. Add 100 μl of starting drug dilution (2× in $VB^{++}$) to well 1.
12. Serially dilute (1:2) the drug from wells 1 to 10 as follow
    a. Take 50 μl of solution from the originating well
    b. Add this to the next well
    c. Mix by pipetting several times
    d. Repeat up to well #10
Note: from well #10 remove 50 ul and discard.
13. Add 50 μl of 2× plasma dilution to wells 1 to 11 (q.v. 5.10 above)
14. Incubate for 1 h
15. Wash twice with wash buffer
16. Add 50 μl of 1/1000 dilution of C3-HRP Ab in 1% BSA/PBS
17. Incubate for 1 h
18. Add 100 μl of TMB to all wells
19. Incubate for 5 min
20. Add 50 μl 3M $H_2SO_4$
21. Read the plate at 405 nm $VB^{++}$ Formula:

| | |
|---|---|
| Barbital | 5 mM |
| NaCl | 72.5 mM |
| $MgCl_2$ | 0.5 mM |
| $CaCl_2$ | 0.15 mM |
| pH | 7.3-7.4 |

Stock Solutions:

| Veronal Buffer (5X) | | | |
|---|---|---|---|
| | Prod # | MW | For 500 ml |
| 9 mM Sodium Barbitone | Sigma B0500 | 206.17 | 927 mg |
| 15.5 mM diethylbarbituric acid | Sigma B0375 | 184.19 | 1.42 grams |
| | Prod # | MW | For 50 ml |
| Mg-Cl2 (200X) | | | |
| 100 mM $MgCl_2$-$6H_2O$ | Sigma M0250 | 203.30 | 1.00 gram |
| $CaCl_2$ (500x) | | | |
| 75 mM $CaCl_2$ | Sigma C7902 | 147.01 | 551.28 mg |

The above assay is performed using a variety of different compstatin analogs. Percent inhibition may be normalized by considering 100% activation equal to activation occurring in the absence of compound or equal to activation occurring in the in the presence of an equal amount of an inactive variant of compstatin.

Example 2

ELISA-Based Assay for Alternative Complement Pathway Activation to Assess Complement Inhibiting Activity

This example describes a protocol for measuring complement pathway activation and the ability of a test agent, e.g., a complement inhibitor of interest, to inhibit it. The protocol measures C3b deposition in an ELISA format. C3b deposition monitored here is through complement activated by the alternative pathway. Briefly, 96-well plates are coated with LPS+BSA. Plasma (or any biological sample of interest) and any complement inhibitor of interest are then added and incubated, followed by addition of Anti-human C3 HRP-conjugated antibody. After an additional incubation, substrate is added and signal detected.

Materials:
Ninety-six well ELISA plate (Corning 3590)
LPS from *Salmonella typhosa*—Sigma L7136 (40 ug/ml in PBS)
BSA 1% in PBS—Calbiochem #126626 1/30 dilution
Veronal Buffer+10 mM $MgCl_2$+10 mM EGTA (VB-Mg EGTA)
Plasma (collected with Lepirudin at 5 ug/ml final concentration)
Anti-human C3 HRP-conjugated polyclonal Ab (C3-HRP Ab, Cappel 55237)
Tween-20 Wash Buffer (0.05% in PBS)

TMB (Peroxidase substrate)—1:1 mixture of BD 51-2607KC and 51-2606KC.

3M $H_2SO_4$

Micro-plate Reader

Protocol:
1. Add 50 μl/well of LPS at 40 μg/ml (in PBS)
2. Incubate for 2 hours at room temp
3. Remove by shaking and tapping the plate; aspirate any remaining fluid.
4. Block by adding 200 μl of 1% BSA/PBS
5. Incubate for 1 h at room temp
6. Remove by shaking and tapping the plate; aspirate any remaining fluid.
7. Add 50 μl VB-Mg EGTA to wells #2 to 12
8. Add 100 μl of starting drug dilution (2× in VB-Mg EGTA) to well 1.
9. Serially dilute (1:2) the drug from wells 1 to 10 as follow
   e. Take 50 μl of solution from the originating well
   f. Add this to the next well
   g. Mix by pipetting several times
   h. Repeat up to well #10

Note: from well #10 remove 50 μl and discard.

10. Add 50 μl of 2× plasma dilution to wells 1 to 11. This involves the following: (i) pipette 50 μl of plasma into well #1; (i) mix well by pipetting; (ii) discard pipette tip and replace with fresh one; (iii) pipette 50 μl of the contents of well #1 and add to well #2. Repeat steps (i) through (iii) for wells #2 through #11.
11. Incubate for 1 h
12. Wash twice with wash buffer
13. Add 50 μl of 1/1000 dilution of C3-HRP Ab in 1% BSA/PBS
14. Incubate for 1 h
15. Add 100 μl of TMB to all wells
16. Incubate for 30 min
17. Add 50 μl 3M $H_2SO_4$
18. Read the plate at 405 nm The above assays may be performed using a variety of different complement inhibitors and/or plasma samples (or samples of any body fluid of interest). Percent inhibition may be normalized by considering 100% activation equal to activation occurring in the absence of compound or equal to activation occurring in the in the presence of an equal amount of an inactive variant of a compound.

Example 3

Data Analysis

The following procedure may be used to calculate $IC_{50}$ values for a complement inhibitor and biological sample of interest. Data is analyzed using GraphPad Prism v4.03 software. Data sets from each experiment are normalized to percent activation compared to the 100% activation control corresponding to the well to which no compound is added. Then, all single data sets are pooled into a single table. Drug concentration values (X values) are transformed to their Logarithms and percent activation (Pa) (Y values) is transformed to percent inhibition (Pi) using the following formula Pi=100–Pa (Yi=100–Ya). The percent inhibition is plotted against the drug concentration and the resulting data set is fit to a sigmoidal-dose response function [Y=Bottom+(Top–Bottom)/(1+10^((Log $EC_{50}$–X)))]. $IC_{50}$ values are obtained from the fit parameters.

Example 4

Selection of Complement Inhibitor

The methods described in Examples 1-3 are used to measure complement activation in various biological samples, such as plasma, synovial fluid, CSF, etc., and to assess the ability of a panel of complement inhibitors to inhibit complement activation in such samples. Samples are obtained from normal individuals and those suffering from a complement-mediated disorder such as arthritis. For example, arthrocentesis is used to collect synovial fluid, or biopsy is used to collect synovial membrane tissue. The data are used to select a complement inhibitor and dose for local administration to individuals suffering from the disorder. For example, the complement inhibitor and dose may be selected so as to reduce average complement activity in biological samples obtained from individuals suffering from the disorder to the average complement activity found in comparable biological samples obtained from individuals not suffering from the disorder.

Example 5

Development of Microparticle Sustained Release Formulation

The method of Example 4 is used to select a complement inhibitor for use in individuals suffering from rheumatoid arthritis. A panel of sustained release microparticle formulations containing the complement inhibitor is prepared using a variety of different materials (PLGA, polyanhydrides, polyorthoesters). The particles have a variety of average diameters and densities. The sustained release formulations are tested in vitro (e.g., in physiological saline) to identify those that release sufficient complement inhibitor to achieve a desired concentration in a desired volume for at least two weeks.

Selected formulations are tested in vivo in antigen-induced arthritis (AIA) rabbit and rat models of rheumatoid arthritis. The formulations are administered to one or more affected joint cavities by intraarticular injection. Synovial tissue and fluid are obtained 28 days following administration and evaluated using various techniques including immunohistochemistry, quantitative image analysis, and immunoassay. Various parameters including inflammatory cytokine synthesis, inflammatory cell infiltrate, and appearance are assessed and compared with appropriate controls. Clinical parameters including swelling and gait disturbance are also evaluated. Blood samples are obtained prior to administration, at 2, 4, 8, 12, and 24 hours following administration, and at weekly intervals thereafter for 6 weeks and evaluated to determine whether the treatment detectably affects systemic complement activity.

Example 6

Treatment of Arthritis in an Animal Model by Local Administration of a Sustained Release Formulation of a Complement Inhibitor Recombinant SPICE is produced in and purified from a *Pichia pastoris* expression system as described in (Sahu, A, et al., *J. Immunol.*, 160, 5596-5604, 1998). A solution comprising a gel-forming material and SPICE is prepared and injected into a joint of an animal model for arthritis in which local synthesis and/or local activation of complement occurs. A gel is formed in the joint space. SPICE is released over a prolonged time in amounts sufficient to provide a concentration sufficient to reduce complement activation in the synovial fluid and/or synovial membrane to within twice normal levels, or by a factor of at least 2, for a desired average time period. Symptoms and occurrence of potential side effects are monitored. A reduction in average severity of one or more symptom(s) is indicative of efficacy. Blood samples are obtained prior to administration, at 2, 4, 8, 12, and 24 hours following administration, and at weekly intervals thereafter for the duration of the study and evaluated to determine whether the treatment detectably affects systemic complement activity and, if so, to what extent.

Example 7

Treatment of Arthritis in an Animal Model by Local Administration of a Sustained Release Formulation of a Complement Inhibitor Example 6 is repeated using the compstatin analog of SEQ ID NO: 14 instead of SPICE. The compstatin analog is chemically synthesized using standard methods and added to the solution containing the gel-forming material. The animal is a non-human primate. The compstatin analog is released over time in amounts sufficient to provide a concentration that reduces complement activation in the synovial fluid and/or synovial membrane to within twice normal levels, or by a factor of at least 2, for a desired average time period. Symptoms are monitored. A reduction in one or more symptom(s) is indicative of efficacy. Blood samples are obtained prior to administration, at 2, 4, 8, 12, and 24 hours following administration, and at weekly intervals thereafter for the duration of the study and evaluated to determine whether the treatment detectably affects systemic complement activity and, if so, to what extent.

Example 8

Treatment of Arthritis in an Animal Model by Local Administration of a Sustained Release Formulation of a Complement Inhibitor A solution comprising a gel-forming material and the compstatin analog of SEQ ID NO: 28 (chemically synthesized using standard methods) is prepared and injected into a joint of an animal model for arthritis in which local synthesis and/or local activation of complement occurs. The animal is a non-human primate. The compstatin analog is released over a prolonged time in amounts sufficient to provide a concentration sufficient to reduce complement activation in the synovial fluid and/or synovial membrane to within twice normal levels, or by a factor of at least 2, for a desired period of time. Symptoms are monitored. A reduction in one or more symptom(s) is indicative of efficacy. Blood samples are obtained prior to administration, at 2, 4, 8, 12, and 24 hours following administration, and at weekly intervals thereafter for 6 weeks and evaluated to determine whether the treatment detectably affects systemic complement activity and, if so, to what extent.

Example 9

Treatment of Arthritis in an Animal Model by Local Administration of a Sustained Release Formulation of a Complement Inhibitor A solution comprising a gel-forming material and the compstatin analog of SEQ ID NO: 29 (chemically synthesized using standard methods) is prepared and injected into a joint of an arthritis animal model in which local synthesis and/or local activation of complement occurs. The animal is a non-human primate. The compstatin analog is released over a prolonged time in amounts sufficient to provide a concentration sufficient to reduce complement activation in the synovial fluid and/or synovial membrane to within twice normal levels for a desired period of time. Symptoms and potential side effects are monitored. A reduction in one or more symptom(s) is indicative of efficacy. Blood samples are obtained prior to administration, at 2, 4, 8, 12, and 24 hours following administration, and at weekly intervals thereafter for 8 weeks and evaluated to determine whether the treatment detectably affects systemic complement activity and, if so, to what extent.

Example 10

Treatment of Arthritis in an Animal Model by Local Administration of a Sustained Release Formulation of a Complement Inhibitor A solution comprising a gel-forming material and the compstatin analog of SEQ ID NO: 32 (chemically synthesized using standard methods) is prepared and injected into a joint of an arthritis animal model in which local synthesis and/or local activation of complement occurs. The animal is a non-human primate. The compstatin analog is released over a prolonged time in amounts sufficient to provide a concentration sufficient to reduce complement activation in the synovial fluid and/or synovial membrane to within normal levels for at least one month. Symptoms and potential side effects are monitored. A reduction in one or more symptom(s) is indicative of efficacy. Blood samples are obtained prior to administration, at 2, 4, 8, 12, and 24 hours following administration, and at weekly intervals thereafter for 8 weeks and evaluated to determine whether the treatment detectably affects systemic complement activity and, if so, to what extent.

Example 11

Treatment of Arthritis in an Animal Model by Local Administration of a Sustained Release Formulation of a Complement Inhibitor Example 5 is repeated using recombinantly produced SPICE as the complement inhibitor. SPICE is released over a prolonged period of time in amounts sufficient to provide a concentration sufficient to reduce complement activation in the synovial fluid and/or synovial membrane to within normal levels for at least one month. Symptoms and potential side effects are monitored. A reduction in one or more symptom(s) is indicative of efficacy. Blood samples are obtained prior to administration, at 2, 4, 8, 12, and 24 hours following administration, and at weekly intervals thereafter for 6 weeks and evaluated to determine whether the treatment detectably affects systemic complement activity and, if so, to what extent.

Example 12

Treatment of Arthritis in an Animal Model by Local Administration of a Sustained Release Formulation of a Complement Inhibitor Example 5 is repeated using a highly potent compstatin analog as the complement inhibitor. The animal is a non-human primate. The compstatin analog is released over a prolonged time period in amounts sufficient to provide a concentration sufficient to reduce complement activation in the synovial fluid and/or synovial membrane to within normal levels for at least one month. Symptoms and potential side effects are monitored. A reduction in one or more symptom(s) is indicative of efficacy. Blood samples are obtained prior to administration, at 2, 4, 8, 12, and 24 hours following administration, and at weekly intervals thereafter for 6 weeks and evaluated to determine whether the treatment detectably affects systemic complement activity and, if so, to what extent.

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. It will be appreciated that the invention is in no way dependent upon particular results achieved in any specific example or with any specific embodiment. In the claims articles such as "a,", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. For example, and without limitation, it is understood that where claims or description indicate that a residue at a particular position may be selected from a particular group of amino acids or amino acid analogs, the invention includes individual embodiments in which the residue at that position is any of the listed amino acids or amino acid analogs. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. In particular, any claim that is dependent on another claim can be modified to include one or more elements or limitations found in any other claim that is dependent on the same base claim. Furthermore, where the claims recite a composition, it is to be understood that methods of administering the composition according to any of the methods disclosed herein, and methods of using the composition for any of the purposes disclosed herein are included, and methods of making the composition according to any of the methods of making disclosed herein are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. For purposes of conciseness only some of these embodiments have been specifically recited in haec verba herein, but the invention includes all such embodiments. It should also be understood that, in general, where the invention, or aspects of the invention, is/are referred to as comprising particular elements, features, etc., certain embodiments of the invention or aspects of the invention consist, or consist essentially of, such elements, features, etc.

The inclusion of a "providing" step in certain methods of the invention is intended to indicate that the composition is administered to treat a disorder recited in the method. Thus the subject will have or be at risk of the disorder and the composition is administered to treat the disorder, typically upon the sound recommendation of a medical or surgical practitioner, who may or may not be the same individual who administers the composition. The invention includes embodiments in which a step of providing is not explicitly included and embodiments in which a step of providing is included. The invention also includes embodiments in which a step of identifying the subject as being at risk of or suffering from a complement-mediated disorder is included.

Where ranges are given, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. A time period of 1 month is understood to mean 30 days. A time period of 1 year is understood to mean 365 days. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately".

It is to be understood that any particular embodiment, feature, or aspect of the present invention may be explicitly excluded from any one or more of the claims. For example, any particular composition, compound or class of compounds, extravascular location, route or method of administration, dose, formulation, device, or complement-mediated disorder can be excluded from any one or more claims.

We claim:

1. A method of treating a complement-mediated disorder which is an inflammatory condition of the respiratory system comprising administering an effective amount of a compstatin analog comprising a cyclic peptide having a core sequence of X'aa-Gln-Asp-Xaa-Gly (SEQ ID NO: 3), wherein X'aa and Xaa are each independently selected from Trp and analogs of Trp, directly to the respiratory tract.

2. The method of claim 1, wherein said compstatin analog is administered in an amount that reduces systemic complement activation by less than 20%.

3. The method of claim 1, wherein the compstatin analog is a compound that comprises a cyclic peptide having a core sequence of X'aa-Gln-Asp-Xaa-Gly-X"aa (SEQ ID NO: 4), where X'aa and Xaa are each independently selected from Trp and analogs of Trp and X"aa is selected from His, Ala, single methyl unbranched amino acids, Phe, Tip, and analogs of Trp.

4. The method of claim 1, wherein the compstatin analog is administered by inhalation.

5. The method of claim 1, wherein said compstatin analog is administered in an amount sufficient to inhibit complement activity attributable to at least one complement activation pathway in the respiratory tract by at least 25%.

6. The method of claim 1, wherein said compstatin analog is administered in an amount sufficient to reduce complement activity attributable to at least one complement pathway in the respiratory tract to a level no more than twice the average level found in the respiratory tract in the absence of the inflammatory condition.

7. The method of claim 1, wherein the inflammatory condition is mediated at least in part by a locally produced soluble complement protein, wherein the compstatin analog is administered in an amount sufficient to reduce complement activity attributable to said locally produced complement protein to a level no more than twice the average level found in the respiratory tract in the absence of the inflammatory condition.

8. The method of claim 1, wherein said compstatin analog inhibits local activation of C3.

9. The method of claim 1, wherein said compstatin analog inhibits cleavage of complement component C3.

10. The method of claim 1, wherein said compstatin analog binds to complement component C3.

11. The method of claim 1, wherein said inflammatory condition of the respiratory system is selected from the group consisting of: asthma and chronic obstructive pulmonary disease (COPD).

12. The method of claim 1, wherein said effective amount has essentially no effect on systemic complement activation when administered to the respiratory system.

13. The method of claim 1, wherein said compstatin analog is released from a sustained release formulation or device that releases the compstatin analog over time.

14. The method of claim 13, wherein said sustained release formulation comprises a plurality of microparticles or nanoparticles.

15. The method of claim 13, wherein said sustained release formulation comprises a biodegradable polymeric matrix.

16. The method of claim 1, further comprising the step of administering a second agent effective against the inflammatory condition of the respiratory system.

17. The method of claim 1, further comprising the step of: determining whether complement activity is aberrantly high in the respiratory tract in the subject's body.

18. A method of treating an inflammatory condition of the respiratory system comprising administering a compstatin analog comprising a cyclic peptide having a core sequence of X'aa-Gln-Asp-Xaa-Gly (SEQ ID NO: 3) wherein X'aa and Xaa are each independently selected from Trp and analogs of Trp directly to the respiratory tract, wherein said compstatin analog binds to a locally produced soluble complement protein.

19. The method of claim 18, wherein said inflammatory condition of the respiratory system is selected from the group consisting of: asthma, COPD, allergic rhinitis, and infection-associated inflammation.

20. The method of claim 18, wherein said compstatin analog is administered as a component of an inhalable dry powder.

21. The method of claim 18, wherein said compstatin analog is administered as a component of an inhalable liquid aerosol.

* * * * *

UNITED STATES PATENT AND TRADEMARK OFFICE
CERTIFICATE OF CORRECTION

PATENT NO. : 8,580,735 B2
APPLICATION NO. : 12/525799
DATED : November 12, 2013
INVENTOR(S) : Francois et al.

It is certified that error appears in the above-identified patent and that said Letters Patent is hereby corrected as shown below:

In the Claims:

Col. 127, Lines 22-27

On the last page of the patent, please correct claim 3 from:

"The method of claim 1, wherein the compstatin analog is a compound that comprises a cyclic peptide having a core sequence of X'aa – Gln – Asp – Xaa – Gly – X"aa (SEQ ID NO: 4), where X'aa and Xaa are each independently selected from Trp and analogs of Trp and X"aa is selected from His, Ala, single methyl unbranched amino acids, Phe, Tip, and analogs of Trp."

to read:

--The method of claim 1, wherein the compstatin analog is a compound that comprises a cyclic peptide having a core sequence of X'aa – Gln – Asp – Xaa – Gly – X"aa (SEQ ID NO: 4), where X'aa and Xaa are each independently selected from Trp and analogs of Trp and X"aa is selected from His, Ala, single methyl unbranched amino acids, Phe, Trp, and analogs of Trp.--

Signed and Sealed this
Seventh Day of January, 2014

Margaret A. Focarino
*Commissioner for Patents of the United States Patent and Trademark Office*

UNITED STATES PATENT AND TRADEMARK OFFICE
CERTIFICATE OF CORRECTION

PATENT NO. : 8,580,735 B2  Page 1 of 1
APPLICATION NO. : 12/525799
DATED : November 12, 2013
INVENTOR(S) : Francois et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 864 days.

Signed and Sealed this
Twenty-second Day of September, 2015

Michelle K. Lee
*Director of the United States Patent and Trademark Office*

SEQUENCE LISTING

```
<160> NUMBER OF SEQ ID NOS: 43

<210> SEQ ID NO 1
<211> LENGTH: 6
<212> TYPE: PRT
<213> ORGANISM: Artificial Sequence
<220> FEATURE:
<223> OTHER INFORMATION: Synthetic (sequence used for exemplary
      purposes to define "identity")
```

```
<400> SEQUENCE: 1

Ala Lys Leu Ser Ile Gly
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: Variant
<222> LOCATION: (1)..(1)
<223> OTHER INFORMATION: Xaa = Ala, Cys, Asp, Glu, Phe, Gly, His,
      Ile, Lys, Leu, Met, Asn, Pro, Gln, Arg, Ser, Thr, Val, Trp, Tyr.
      Xaa can be repeated n times. Xaa at position 6 can be repated m
      times, wherein n + m is between 5 and 21.
<220> FEATURE:
<221> NAME/KEY: Variant
<222> LOCATION: (4)..(4)
<223> OTHER INFORMATION: Xaa = Trp or Trp analog
<220> FEATURE:
<221> NAME/KEY: Variant
<222> LOCATION: (6)..(6)
<223> OTHER INFORMATION: Xaa = Ala, Cys, Asp, Glu, Phe, Gly, His,
      Ile, Lys, Leu, Met, Asn, Pro, Gln, Arg, Ser, Thr, Val, Trp, Tyr.
      Xaa can be repeated m times.  Xaa at position 6 can be repeated n
      times, wherein n + m is between 5 and 21.

<400> SEQUENCE: 2

Xaa Gln Asp Xaa Gly Xaa
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic; core sequence of peptide
<220> FEATURE:
<221> NAME/KEY: Variant
<222> LOCATION: (1)..(1)
<223> OTHER INFORMATION: Xaa = Trp or Trp analog
<220> FEATURE:
<221> NAME/KEY: Variant
<222> LOCATION: (4)..(4)
<223> OTHER INFORMATION: Xaa = Trp or Trp analog

<400> SEQUENCE: 3

Xaa Gln Asp Xaa Gly
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: Variant
<222> LOCATION: (1)..(1)
<223> OTHER INFORMATION: Xaa = Trp or Trp analog
<220> FEATURE:
<221> NAME/KEY: Variant
<222> LOCATION: (4)..(4)
<223> OTHER INFORMATION: Xaa = Trp or Trp analog
<220> FEATURE:
<221> NAME/KEY: Variant
<222> LOCATION: (6)..(6)
<223> OTHER INFORMATION: Xaa = His, Ala, analog of Ala, analog of Phe,
      or analog of Trp

<400> SEQUENCE: 4
```

```
Xaa Gln Asp Xaa Gly Xaa
1               5

<210> SEQ ID NO 5
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: Variant
<222> LOCATION: (1)..(4)
<223> OTHER INFORMATION: Xaa = Ala, Cys, Asp, Glu, Phe, Gly, His,
      Ile, Lys, Leu, Met, Asn, Pro, Gln, Arg, Ser, Thr, Val, Trp,
      Tyr, or analog of Lys, Leu, Met, Asn, Pro, Gln, Arg, Ser, Thr, Val, Trp, or Tyr <220> FEATURE:
<221> NAME/KEY: Variant
<222> LOCATION: (7)..(7)
<223> OTHER INFORMATION: Xaa = Ala, Cys, Asp, Glu, Phe, Gly, His,
      Ile, Lys, Leu, Met, Asn, Pro, Gln, Arg, Ser, Thr, Val, Trp,
      Tyr, or analog of Lys, Leu, Met, Asn, Pro, Gln, Arg, Ser, Thr, Val, Trp, or Tyr <220> FEATURE:
<221> NAME/KEY: Variant
<222> LOCATION: (9)..(13)
<223> OTHER INFORMATION: Xaa = Ala, Cys, Asp, Glu, Phe, Gly, His,
      Ile, Lys, Leu, Met, Asn, Pro, Gln, Arg, Ser, Thr, Val, Trp,
      Tyr, or analog of Lys, Leu, Met, Asn, Pro, Gln, Arg, Ser, Thr, Val, Trp, or Tyr

<400> SEQUENCE: 5

Xaa Xaa Xaa Xaa Gln Asp Xaa Gly Xaa Xaa Xaa Xaa Xaa
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: Variant
<222> LOCATION: (1)..(1)
<223> OTHER INFORMATION: Xaa = Ile, Val, Leu, B1-Ile, B1-Leu, or
      dipeptide comprising Gly-Ile or B1-Glu-Ile, wherein B1 is a
      blocking moiety
<220> FEATURE:
<221> NAME/KEY: DISULFID
<222> LOCATION: (2)..(2)
<223> OTHER INFORMATION: Joined by disulfide bond to other Cys residue
<220> FEATURE:
<221> NAME/KEY: Variant
<222> LOCATION: (4)..(4)
<223> OTHER INFORMATION: Xaa = Trp or Trp analog
<220> FEATURE:
<221> NAME/KEY: Variant
<222> LOCATION: (7)..(7)
<223> OTHER INFORMATION: Xaa = Trp or Trp analog
<220> FEATURE:
<221> NAME/KEY: Variant
<222> LOCATION: (9)..(9)
<223> OTHER INFORMATION: Xaa = His, Ala, analog of Ala, Phe, Trp, or
      analog of Trp
<220> FEATURE:
<221> NAME/KEY: DISULFID
<222> LOCATION: (12)..(12)
<223> OTHER INFORMATION: Joined by disulfide bond to other Cys residue
<220> FEATURE:
<221> NAME/KEY: Variant
<222> LOCATION: (13)..(13)
```

```
<223> OTHER INFORMATION: Xaa = L-Thr, D-Thr, Ile, Val, or Gly;
      dipeptide Thr-Ala or Thr-Asn; or tripeptide Thr-Ala-Asn;
      wherein the carboxy terminal -OH of any of the L-Thr, D-Thr,
      Ile, Val, Gly, Ala, Asn optionally is replaced by blocking
      moiety B2

<400> SEQUENCE: 6

Xaa Cys Val Xaa Gln Asp Xaa Gly Xaa His Arg Cys Xaa
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: Variant
<222> LOCATION: (1)..(1)
<223> OTHER INFORMATION: Xaa = Ile, Val, Leu, Ac-Ile, Ac-Leu, or
      dipeptide comprising Gly-Ile or Ac-Glu-Ile, wherein 'Ac'
      signifies acetylated
<220> FEATURE:
<221> NAME/KEY: DISULFID
<222> LOCATION: (2)..(2)
<223> OTHER INFORMATION: Joined by disulfide bond to other Cys residue
<220> FEATURE:
<221> NAME/KEY: Variant
<222> LOCATION: (4)..(4)
<223> OTHER INFORMATION: Xaa = Trp and Trp analogs
<220> FEATURE:
<221> NAME/KEY: Variant
<222> LOCATION: (7)..(7)
<223> OTHER INFORMATION: Xaa = Trp and Trp analogs
<220> FEATURE:
<221> NAME/KEY: Variant
<222> LOCATION: (9)..(9)
<223> OTHER INFORMATION: Xaa = His, Ala, analog of Ala, Phe, Trp, or
      analog of Trp
<220> FEATURE:
<221> NAME/KEY: DISULFID
<222> LOCATION: (12)..(12)
<223> OTHER INFORMATION: Joined by disulfide bond to other Cys residue
<220> FEATURE:
<221> NAME/KEY: Variant
<222> LOCATION: (13)..(13)
<223> OTHER INFORMATION: Xaa = L-Thr, D-Thr, Ile, Val, or Gly;
      dipeptide Thr-Ala or Thr-Asn; or tripeptide Thr-Ala-Asn;
      wherein the carboxy terminal -Oh of any of the L-Thr, D-Thr,
      Ile, Val, Gly, Ala, or Asn optionally is replaced by -NH2

<400> SEQUENCE: 7

Xaa Cys Val Xaa Gln Asp Xaa Gly Xaa His Arg Cys Xaa
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic; compstatin
<220> FEATURE:
<221> NAME/KEY: DISULFIDE
<222> LOCATION: (2)..(2)
<223> OTHER INFORMATION: Optionally joined to other cysteine via
      disulfide bridge
<220> FEATURE:
<221> NAME/KEY: DISULFIDE
<222> LOCATION: (12)..(12)
<223> OTHER INFORMATION: Optionally joined to other cysteine via
      disulfide bridge
<220> FEATURE:
<221> NAME/KEY: MOD_RES
<222> LOCATION: (13)..(13)
<223> OTHER INFORMATION: AMIDATION
```

```
-continued

<400> SEQUENCE: 8

Ile Cys Val Val Gln Asp Trp Gly His His Arg Cys Thr
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synethetic; compstatin analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(2)
<223> OTHER INFORMATION: Optionally joined to other cysteine via
      disulfide bridge
<220> FEATURE:
<221> NAME/KEY: DISULFID
<222> LOCATION: (12)..(12)
<223> OTHER INFORMATION: Optionally joined to other cysteine via
      disulfide bridge
<220> FEATURE:
<221> NAME/KEY: MOD_RES
<222> LOCATION: (13)..(13)
<223> OTHER INFORMATION: AMIDATION

<400> SEQUENCE: 9

Ile Cys Val Val Gln Asp Trp Gly His His Arg Cys Thr
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Synthetic; compstatin analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(2)
<223> OTHER INFORMATION: Optionally joined to other cysteine via
      disulfide bridge
<220> FEATURE:
<221> NAME/KEY: DISULFID
<222> LOCATION: (12)..(12)
<223> OTHER INFORMATION: Optionally joined to other cysteine via
      disulfide bridge
<220> FEATURE:
<221> NAME/KEY: MOD_RES
<222> LOCATION: (13)..(13)
<223> OTHER INFORMATION: AMIDATION

<400> SEQUENCE: 10

Ile Cys Val Tyr Gln Asp Trp Gly Ala His Arg Cys Thr
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Synthetic; compstatin analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
```

-continued

```
<222> LOCATION: (2)..(2)
<223> OTHER INFORMATION: Optionally joined to other cysteine via
      disulfide bridge
<220> FEATURE:
<221> NAME/KEY: DISULFID
<222> LOCATION: (12)..(12)
<223> OTHER INFORMATION: Optionally joined to other cysteine via
      disulfide bridge

<400> SEQUENCE: 11

Ile Cys Val Trp Gln Asp Trp Gly Ala His Arg Cys Thr
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetic; compstatin analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(2)
<223> OTHER INFORMATION: Optionally joined to other cysteine via
      disulfide bridge
<220> FEATURE:
<221> NAME/KEY: DISULFID
<222> LOCATION: (12)..(12)
<223> OTHER INFORMATION: Optionally joined to other cysteine via
      disulfide bridge
<220> FEATURE:
<221> NAME/KEY: MOD_RES
<222> LOCATION: (13)..(13)
<223> OTHER INFORMATION: AMIDATION

<400> SEQUENCE: 12

Ile Cys Val Trp Gln Asp Trp Gly Ala His Arg Cys Thr
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Synthetic; compstatin analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(2)
<223> OTHER INFORMATION: Optionally joined to other cysteine via
      disulfide bridge
<220> FEATURE:
<221> NAME/KEY: DISULFID
<222> LOCATION: (12)..(12)
<223> OTHER INFORMATION: Optionally joined to other cysteine via
      disulfide bridge
<220> FEATURE:
<221> NAME/KEY: MISC_FEATURE
<222> LOCATION: (13)..(13)
<223> OTHER INFORMATION: D-Threonine

<400> SEQUENCE: 13

Ile Cys Val Trp Gln Asp Trp Gly Ala His Arg Cys Thr
1               5                   10

<210> SEQ ID NO 14
<211> LENGTH: 13
<212> TYPE: PRT
```

```
<213> ORGANISM: Artificial Sequence
<220> FEATURE:
<223> OTHER INFORMATION: Synthetic; compstatin analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(2)
<223> OTHER INFORMATION: Optionally joined to other cysteine via
      disulfide bridge
<220> FEATURE:
<221> NAME/KEY: DISULFID
<222> LOCATION: (12)..(12)
<223> OTHER INFORMATION: Optionally joined to other cysteine via
      disulfide bridge
<220> FEATURE:
<221> NAME/KEY: MOD_RES
<222> LOCATION: (12)..(12)
<223> OTHER INFORMATION: 2-Naphthylalanine
<220> FEATURE:
<221> NAME/KEY: MOD_RES
<222> LOCATION: (13)..(13)
<223> OTHER INFORMATION: AMIDATION

<400> SEQUENCE: 14

Ile Cys Val Ala Gln Asp Trp Gly Ala His Arg Cys Thr
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Synthetic; compstatin analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(2)
<223> OTHER INFORMATION: Optionally joined to other cysteine via
      disulfide bridge
<220> FEATURE:
<221> NAME/KEY: MOD_RES
<222> LOCATION: (4)..(4)
<223> OTHER INFORMATION: 2-Naphthylalanine
<220> FEATURE:
<221> NAME/KEY: DISULFID
<222> LOCATION: (12)..(12)
<223> OTHER INFORMATION: Optionally joined to other cysteine via
      disulfide bridge

<400> SEQUENCE: 15

Ile Cys Val Ala Gln Asp Trp Gly Ala His Arg Cys Thr
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Synthetic; compstatin analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(2)
<223> OTHER INFORMATION: Optionally joined to other cysteine via
      disulfide bridge
<220> FEATURE:
<221> NAME/KEY: MOD_RES
```

```
<222> LOCATION: (4)..(4)
<223> OTHER INFORMATION: 1-Naphthylalanine
<220> FEATURE:
<221> NAME/KEY: DISULFID
<222> LOCATION: (12)..(12)
<223> OTHER INFORMATION: Optionally joined to other cysteine via
      disulfide bridge

<400> SEQUENCE: 16

Ile Cys Val Ala Gln Asp Trp Gly Ala His Arg Cys Thr
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Synthetic; compstatin analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(2)
<223> OTHER INFORMATION: Optionally joined to other cysteine via
      disulfide bridge
<220> FEATURE:
<221> NAME/KEY: MOD_RES
<222> LOCATION: (4)..(4)
<223> OTHER INFORMATION: 2-indanylglycine carboxylic acid
<220> FEATURE:
<221> NAME/KEY: DISULFID
<222> LOCATION: (12)..(12)
<223> OTHER INFORMATION: Optionally joined to other cysteine via
      disulfide bridge
<220> FEATURE:
<221> NAME/KEY: MOD_RES
<222> LOCATION: (13)..(13)
<223> OTHER INFORMATION: AMIDATION

<400> SEQUENCE: 17

Ile Cys Val Gly Gln Asp Trp Gly Ala His Arg Cys Thr
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Synthetic; compstatin analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(2)
<223> OTHER INFORMATION: Optionally joined to other cysteine via
      disulfide bridge
<220> FEATURE:
<221> NAME/KEY: MOD_RES
<222> LOCATION: (4)..(4)
<223> OTHER INFORMATION: 2-indanylglycine carboxylic acid
<220> FEATURE:
<221> NAME/KEY: DISULFID
<222> LOCATION: (12)..(12)
<223> OTHER INFORMATION: Optionally joined to other cysteine via
      disulfide bridge

<400> SEQUENCE: 18

Ile Cys Val Gly Gln Asp Trp Gly Ala His Arg Cys Thr
1               5                   10
```

```
<210> SEQ ID NO 19
<211> LENGTH: 13
<212> TYPE: PRT
<213> ORGANISM: Artificial Sequence
<220> FEATURE:
<223> OTHER INFORMATION: Synthetic; compstatin analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(2)
<223> OTHER INFORMATION: Optionally joined to other cysteine via
      disulfide bridge
<220> FEATURE:
<221> NAME/KEY: MOD_RES
<222> LOCATION: (4)..(4)
<223> OTHER INFORMATION: dihydrotryptophan
<220> FEATURE:
<221> NAME/KEY: DISULFID
<222> LOCATION: (12)..(12)
<223> OTHER INFORMATION: Optionally joined to other cysteine via
      disulfide bridge

<400> SEQUENCE: 19

Ile Cys Val Trp Gln Asp Trp Gly Ala His Arg Cys Thr
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Synthetic; compstatin analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(2)
<223> OTHER INFORMATION: Optionally joined to other cysteine by
      disulfide bridge
<220> FEATURE:
<221> NAME/KEY: MOD_RES
<222> LOCATION: (4)..(4)
<223> OTHER INFORMATION: 4-benzoyl-L-phenylalanine
<220> FEATURE:
<221> NAME/KEY: DISULFID
<222> LOCATION: (12)..(12)
<223> OTHER INFORMATION: Optionally joined to other cysteine by
      disulfide bridge

<400> SEQUENCE: 20

Ile Cys Val Ala Gln Asp Trp Gly Ala His Arg Cys Thr
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Synthetic; compstatin analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(2)
<223> OTHER INFORMATION: Optionally joined to other cysteine via
      disulfide bridge
<220> FEATURE:
<221> NAME/KEY: MOD_RES
<222> LOCATION: (4)..(4)
```

-continued

```
<223> OTHER INFORMATION: 4-benzoyl-L-phenylalanine
<220> FEATURE:
<221> NAME/KEY: DISULFID
<222> LOCATION: (12)..(12)
<223> OTHER INFORMATION: Optionally joined to other cysteine via
      disulfide bridge
<220> FEATURE:
<221> NAME/KEY: MOD_RES
<222> LOCATION: (13)..(13)
<223> OTHER INFORMATION: AMIDATION

<400> SEQUENCE: 21

Ile Cys Val Ala Gln Asp Trp Gly Ala His Arg Cys Thr
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Synthetic; compstatin analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(2)
<223> OTHER INFORMATION: Optionally joined to other cysteine via
      disulfide bridge
<220> FEATURE:
<221> NAME/KEY: MOD_RES
<222> LOCATION: (4)..(4)
<223> OTHER INFORMATION: benzothiazolealanine
<220> FEATURE:
<221> NAME/KEY: DISULFID
<222> LOCATION: (12)..(12)
<223> OTHER INFORMATION: Optionally joined to other cysteine via
      disulfide bridge

<400> SEQUENCE: 22

Ile Cys Val Ala Gln Asp Trp Gly Ala His Arg Cys Thr
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Synthetic; compstatin analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(2)
<223> OTHER INFORMATION: Optionally joined to other cysteine via
      disulfide bridge
<220> FEATURE:
<221> NAME/KEY: MOD_RES
<222> LOCATION: (4)..(4)
<223> OTHER INFORMATION: benzothiazolealanine
<220> FEATURE:
<221> NAME/KEY: DISULFID
<222> LOCATION: (12)..(12)
<223> OTHER INFORMATION: Optionally joined to other cysteine via
      disulfide bridge
<220> FEATURE:
<221> NAME/KEY: MOD_RES
<222> LOCATION: (13)..(13)
<223> OTHER INFORMATION: AMIDATION

<400> SEQUENCE: 23

Ile Cys Val Ala Gln Asp Trp Gly Ala His Arg Cys Thr
```

<210> SEQ ID NO 24
<211> LENGTH: 13
<212> TYPE: PRT
<213> ORGANISM: Artificial Sequence
<220> FEATURE:
<223> OTHER INFORMATION: Synthetic; compstatin analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(2)
<223> OTHER INFORMATION: Optionally joined to other cysteine via
      disulfide bridge
<220> FEATURE:
<221> NAME/KEY: MISC_FEATURE
<222> LOCATION: (9)..(9)
<223> OTHER INFORMATION: 2-alpha-aminobutyric acid
<220> FEATURE:
<221> NAME/KEY: DISULFID
<222> LOCATION: (12)..(12)
<223> OTHER INFORMATION: Optionally joined to other cysteine via
      disulfide bridge
<220> FEATURE:
<221> NAME/KEY: MOD_RES
<222> LOCATION: (13)..(13)
<223> OTHER INFORMATION: AMIDATION

<400> SEQUENCE: 24

Ile Cys Val Trp Gln Asp Trp Gly Xaa His Arg Cys Thr
1               5                   10

<210> SEQ ID NO 25
<211> LENGTH: 16
<212> TYPE: PRT
<213> ORGANISM: Artificial Sequence
<220> FEATURE:
<223> OTHER INFORMATION: Synthetic; compstatin analog
<220> FEATURE:
<221> NAME/KEY: MOD_RES
<222> LOCATION: (1)..(1)
<223> OTHER INFORMATION: DEAMINATED
<220> FEATURE:
<221> NAME/KEY: DISULFID
<222> LOCATION: (3)..(3)
<223> OTHER INFORMATION: Optionally joined to other cysteine via
      disulfide bridge
<220> FEATURE:
<221> NAME/KEY: DISULFID
<222> LOCATION: (13)..(13)
<223> OTHER INFORMATION: Optionally joined to other cysteine via
      disulfide bridge

<400> SEQUENCE: 25

Gly Ile Cys Val Trp Gln Asp Trp Gly Ala His Arg Cys Thr Ala Asn
1               5                   10                  15

<210> SEQ ID NO 26
<211> LENGTH: 13
<212> TYPE: PRT
<213> ORGANISM: Artificial Sequence
<220> FEATURE:
<223> OTHER INFORMATION: Synthetic; compstatin analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(2)
<223> OTHER INFORMATION: Optionally joined to other cysteine via
      disulfide bridge

```
<220> FEATURE:
<221> NAME/KEY: MOD_RES
<222> LOCATION: (4)..(4)
<223> OTHER INFORMATION: 5-fluoro-L-tryptophan
<220> FEATURE:
<221> NAME/KEY: DISULFID
<222> LOCATION: (12)..(12)
<223> OTHER INFORMATION: Optionally joined to other cysteine via
      disulfide bridge
<220> FEATURE:
<221> NAME/KEY: MOD_RES
<222> LOCATION: (13)..(13)
<223> OTHER INFORMATION: AMIDATION

<400> SEQUENCE: 26

Ile Cys Val Trp Gln Asp Trp Gly Ala His Arg Cys Thr
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Synthetic; compstatin analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(2)
<223> OTHER INFORMATION: Optionally joined to other cysteine via
      disulfide bridge
<220> FEATURE:
<221> NAME/KEY: MOD_RES
<222> LOCATION: (4)..(4)
<223> OTHER INFORMATION: 5-methyl-tryptophan
<220> FEATURE:
<221> NAME/KEY: DISULFID
<222> LOCATION: (12)..(12)
<223> OTHER INFORMATION: Optionally joined to other cysteine via
      disulfide bridge
<220> FEATURE:
<221> NAME/KEY: MOD_RES
<222> LOCATION: (13)..(13)
<223> OTHER INFORMATION: AMIDATION

<400> SEQUENCE: 27

Ile Cys Val Trp Gln Asp Trp Gly Ala His Arg Cys Thr
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Synthetic; compstatin analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(2)
<223> OTHER INFORMATION: Optionally joined to other cysteine via
      disulfide bridge
<220> FEATURE:
<221> NAME/KEY: MOD_RES
<222> LOCATION: (4)..(4)
<223> OTHER INFORMATION: 1-methyl-tryptophan
<220> FEATURE:
<221> NAME/KEY: DISULFID
<222> LOCATION: (12)..(12)
<223> OTHER INFORMATION: Optionally joined to other cysteine via
      disulfide bridge
<220> FEATURE:
```

```
<221> NAME/KEY: MOD_RES
<222> LOCATION: (13)..(13)
<223> OTHER INFORMATION: AMIDATION

<400> SEQUENCE: 28

Ile Cys Val Trp Gln Asp Trp Gly Ala His Arg Cys Thr
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Synthetic; compstatin analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(2)
<223> OTHER INFORMATION: Optionally joined to other cysteine via
      disulfide bridge
<220> FEATURE:
<221> NAME/KEY: MOD_RES
<222> LOCATION: (7)..(7)
<223> OTHER INFORMATION: 5-fluoro-L-tryptophan
<220> FEATURE:
<221> NAME/KEY: DISULFID
<222> LOCATION: (12)..(12)
<223> OTHER INFORMATION: Optionally joined to other cysteine via
      disulfide bridge
<220> FEATURE:
<221> NAME/KEY: MOD_RES
<222> LOCATION: (13)..(13)
<223> OTHER INFORMATION: AMIDATION

<400> SEQUENCE: 29

Ile Cys Val Trp Gln Asp Trp Gly Ala His Arg Cys Thr
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Synthetic; compstatin analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(2)
<223> OTHER INFORMATION: Optionally joined to other cysteine via
      disulfide bridge
<220> FEATURE:
<221> NAME/KEY: MOD_RES
<222> LOCATION: (4)..(4)
<223> OTHER INFORMATION: 5-fluoro-L-tryptophan
<220> FEATURE:
<221> NAME/KEY: MOD_RES
<222> LOCATION: (7)..(7)
<223> OTHER INFORMATION: 5-fluoro-L-tryptophan
<220> FEATURE:
<221> NAME/KEY: DISULFID
<222> LOCATION: (12)..(12)
<223> OTHER INFORMATION: Optionally joined to other cysteine via
      disulfide bridge
<220> FEATURE:
<221> NAME/KEY: MOD_RES
<222> LOCATION: (13)..(13)
<223> OTHER INFORMATION: AMIDATION

<400> SEQUENCE: 30
```

```
Ile Cys Val Trp Gln Asp Trp Gly Ala His Arg Cys Thr
1               5                   10
```

```
<210> SEQ ID NO 31
<211> LENGTH: 13
<212> TYPE: PRT
<213> ORGANISM: Artificial Sequence
<220> FEATURE:
<223> OTHER INFORMATION: Synthetic; compstatin analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(2)
<223> OTHER INFORMATION: Optionally joined to other cysteine via
      disulfide bridge
<220> FEATURE:
<221> NAME/KEY: MOD_RES
<222> LOCATION: (4)..(4)
<223> OTHER INFORMATION: 5-methyl-tryptophan
<220> FEATURE:
<221> NAME/KEY: MOD_RES
<222> LOCATION: (7)..(7)
<223> OTHER INFORMATION: 5-fluoro-L-tryptophan
<220> FEATURE:
<221> NAME/KEY: DISULFID
<222> LOCATION: (12)..(12)
<223> OTHER INFORMATION: Optionally joined to other cysteine via
      disulfide bridge
<220> FEATURE:
<221> NAME/KEY: MOD_RES
<222> LOCATION: (13)..(13)
<223> OTHER INFORMATION: AMIDATION

<400> SEQUENCE: 31

Ile Cys Val Trp Gln Asp Trp Gly Ala His Arg Cys Thr
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Synthetic; compstatin analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: 1-methyl-tryptophan
<220> FEATURE:
<221> NAME/KEY: MOD_RES
<222> LOCATION: (7)..(7)
<223> OTHER INFORMATION: 5-fluoro-L-tryptophan
<220> FEATURE:
<221> NAME/KEY: MOD_RES
<222> LOCATION: (13)..(13)
<223> OTHER INFORMATION: AMIDATION

<400> SEQUENCE: 32

Ile Cys Val Trp Gln Asp Trp Gly Ala His Arg Cys Thr
1               5                   10

<210> SEQ ID NO 33
<211> LENGTH: 10
<212> TYPE: PRT
<213> ORGANISM: Artificial sequence
<220> FEATURE:
<223> OTHER INFORMATION: Synthetic; inhibitor of C1

<400> SEQUENCE: 33
```

Trp Glu Ser Asn Gly Gln Pro Glu Asn Asn
1               5                   10

<210> SEQ ID NO 34
<211> LENGTH: 17
<212> TYPE: PRT
<213> ORGANISM: Artificial sequence
<220> FEATURE:
<223> OTHER INFORMATION: Synthetic; inhibitor of C1

<400> SEQUENCE: 34

Lys Thr Ile Ser Lys Ala Lys Gly Gln Pro Arg Glu Pro Gln Val Tyr
1               5                   10                  15

Thr

<210> SEQ ID NO 35
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = Ornithine
<220> FEATURE:
<221> NAME/KEY: MISC_FEATURE
<222> LOCATION: (1)..(5)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-cyclohexylalanine

<400> SEQUENCE: 35

Xaa Pro Xaa Trp Arg
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(5)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-cyclohexylalanine

<400> SEQUENCE: 36

Lys Pro Xaa Trp Arg
1               5

<210> SEQ ID NO 37
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = Ala, Arg, Asn, Asp, Cys, Gln, Glu, Gly,
      His, Ile, Lys, Leu, Met, Phe, Pro, Ser, Thr, Val, Trp, Tyr
<220> FEATURE:
<221> NAME/KEY: MISC_FEATURE
<222> LOCATION: (2)..(2)

```
<223> OTHER INFORMATION: Xaa = Ornithine
<220> FEATURE:
<221> NAME/KEY: MISC_FEATURE
<222> LOCATION: (2)..(6)
<223> OTHER INFORMATION: cyclic portion
<220> FEATURE:
<221> NAME/KEY: MISC_FEATURE
<222> LOCATION: (4)..(4)
<223> OTHER INFORMATION: Xaa = D-cyclohexylalanine

<400> SEQUENCE: 37

Xaa Xaa Pro Xaa Trp Arg
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = Ala, Arg, Asn, Asp, Cys, Gln, Glu, Gly,
      His, Ile, Lys, Leu, Met, Phe, Pro, Ser, Thr, Val, Trp, Tyr
<220> FEATURE:
<221> NAME/KEY: MISC_FEATURE
<222> LOCATION: (2)..(6)
<223> OTHER INFORMATION: cyclic portion
<220> FEATURE:
<221> NAME/KEY: MISC_FEATURE
<222> LOCATION: (4)..(4)
<223> OTHER INFORMATION: Xaa = D-cyclohexylalanine

<400> SEQUENCE: 38

Xaa Lys Pro Xaa Trp Arg
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa = Ornithine
<220> FEATURE:
<221> NAME/KEY: MISC_FEATURE
<222> LOCATION: (2)..(6)
<223> OTHER INFORMATION: cyclic portion
<220> FEATURE:
<221> NAME/KEY: MISC_FEATURE
<222> LOCATION: (4)..(4)
<223> OTHER INFORMATION: Xaa = D-cyclohexylalanine

<400> SEQUENCE: 39

Phe Xaa Pro Xaa Trp Arg
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(6)
<223> OTHER INFORMATION: cyclic portion
<220> FEATURE:
<221> NAME/KEY: MISC_FEATURE
<222> LOCATION: (4)..(4)
```

<223> OTHER INFORMATION: Xaa = D-cyclohexylalanine

<400> SEQUENCE: 40

Phe Lys Pro Xaa Trp Arg
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: cinnamoylation
<220> FEATURE:
<221> NAME/KEY: MISC_FEATURE
<222> LOCATION: (1)..(1)
<223> OTHER INFORMATION: Xaa = Ornithine
<220> FEATURE:
<221> NAME/KEY: MISC_FEATURE
<222> LOCATION: (1)..(5)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-cyclohexylalanine

<400> SEQUENCE: 41

Xaa Pro Xaa Trp Arg
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: hydrocinnamoylation
<220> FEATURE:
<221> NAME/KEY: MISC_FEATURE
<222> LOCATION: (1)..(1)
<223> OTHER INFORMATION: Xaa = Ornithine
<220> FEATURE:
<221> NAME/KEY: MISC_FEATURE
<222> LOCATION: (1)..(5)
<223> OTHER INFORMATION: cyclic
<220> FEATURE:
<221> NAME/KEY: MISC_FEATURE
<222> LOCATION: (3)..(3)
<223> OTHER INFORMATION: Xaa = D-cyclohexylalanine

<400> SEQUENCE: 42

Xaa Pro Xaa Trp Arg
1               5

<210> SEQ ID NO 43
<211> LENGTH: 13
<212> TYPE: PRT
<213> ORGANISM: Artificial Sequence
<220> FEATURE:
<223> OTHER INFORMATION: Synthetic; compstatin
<220> FEATURE:
<221> NAME/KEY: DISULFIDE
<222> LOCATION: (2)..(2)
<223> OTHER INFORMATION: Optionally joined to other cysteine via
      disulfide bridge
<220> FEATURE:
<221> NAME/KEY: DISULFIDE
<222> LOCATION: (12)..(12)

-continued

```
<223> OTHER INFORMATION: Optionally joined to other cysteine via
      disulfide bridge

<400> SEQUENCE: 43

Ile Cys Val Val Gln Asp Trp Gly His His Arg Cys Thr
1               5                   10
```